United States Patent
Igawa et al.

(10) Patent No.: US 9,334,331 B2
(45) Date of Patent: May 10, 2016

(54) BISPECIFIC ANTIBODIES

(75) Inventors: Tomoyuki Igawa, Shizuoka (JP);
Zenjiro Sampei, Shizuoka (JP); Tetsuo Kojima, Shizuoka (JP); Tetsuhiro Soeda, Shizuoka (JP); Atsushi Muto, Shizuoka (JP); Takehisa Kitazawa, Shizuoka (JP); Yukiko Nishida, Shizuoka (JP); Chifumi Imai, Shizuoka (JP); Tsukasa Suzuki, Shizuoka (JP); Kazutaka Yoshihashi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 376 days.

(21) Appl. No.: 13/885,421

(22) PCT Filed: Nov. 17, 2011

(86) PCT No.: PCT/JP2011/076486
§ 371 (c)(1),
(2), (4) Date: Aug. 30, 2013

(87) PCT Pub. No.: WO2012/067176
PCT Pub. Date: May 24, 2012

(65) Prior Publication Data
US 2013/0330345 A1    Dec. 12, 2013

(30) Foreign Application Priority Data
Nov. 17, 2010 (JP) ................................. 2010-257022

(51) Int. Cl.
*C07K 16/40* (2006.01)
*C07K 16/36* (2006.01)

(52) U.S. Cl.
CPC ................ *C07K 16/40* (2013.01); *C07K 16/36* (2013.01); *C07K 2317/31* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,208,479 A | 6/1980 | Zuk et al. | |
| 4,444,878 A | 4/1984 | Paulus | |
| 4,474,893 A | 10/1984 | Reading | |
| 5,322,678 A | 6/1994 | Morgan et al. | |
| 5,496,549 A | 3/1996 | Yamazaki et al. | |
| 5,591,828 A | 1/1997 | Bosslet et al. | |
| 5,639,641 A | 6/1997 | Pedersen et al. | |
| 5,744,446 A | 4/1998 | Lollar et al. | |
| 5,795,965 A | 8/1998 | Tsuchiya et al. | |
| 5,859,205 A | 1/1999 | Adair et al. | |
| 5,945,311 A | 8/1999 | Lindhofer et al. | |
| 6,005,091 A | 12/1999 | Blackburn et al. | |
| 6,010,902 A | 1/2000 | Ledbetter et al. | |
| 6,329,511 B1 | 12/2001 | Vasquez et al. | |
| 6,485,943 B2 | 11/2002 | Stevens et al. | |
| 6,677,436 B1 | 1/2004 | Sato et al. | |
| 6,884,879 B1 | 4/2005 | Baca et al. | |
| 6,913,747 B1 | 7/2005 | Co et al. | |
| 7,033,590 B1 | 4/2006 | Scheiflinger et al. | |
| 7,052,873 B2 | 5/2006 | Tsuchiya | |
| 7,276,585 B2 | 10/2007 | Lazar et al. | |
| 8,062,635 B2 * | 11/2011 | Hattori ............... | C07K 16/2866 424/133.1 |
| 8,592,562 B2 | 11/2013 | Kannan et al. | |
| 8,597,911 B2 | 12/2013 | Miyazaki et al. | |
| 9,096,651 B2 | 8/2015 | Igawa et al. | |
| 2002/0009430 A1 | 1/2002 | Lindhofer et al. | |
| 2002/0062010 A1 | 5/2002 | Arathoon et al. | |
| 2002/0142374 A1 | 10/2002 | Gallo et al. | |
| 2002/0164668 A1 | 11/2002 | Durham et al. | |
| 2003/0190311 A1 | 10/2003 | Dall'Aqua et al. | |
| 2003/0207346 A1 | 11/2003 | Arathoon et al. | |
| 2003/0219441 A1 | 11/2003 | Thorpe et al. | |
| 2003/0224397 A1 | 12/2003 | Lowman et al. | |
| 2004/0081651 A1 | 4/2004 | Karpusas et al. | |
| 2004/0236080 A1 | 11/2004 | Aburatani et al. | |
| 2005/0130224 A1 | 6/2005 | Saito et al. | |
| 2005/0164307 A1 | 7/2005 | Kojima et al. | |
| 2005/0191293 A1 | 9/2005 | Deshpande et al. | |
| 2005/0196397 A1 | 9/2005 | Scheiflinger et al. | |
| 2005/0244416 A1 | 11/2005 | Jung | |
| 2005/0261229 A1 | 11/2005 | Gillies | |
| 2005/0266425 A1 | 12/2005 | Zauderer et al. | |
| 2006/0019342 A1 | 1/2006 | Dall Acqua et al. | |
| 2006/0134709 A1 | 6/2006 | Stavenhagen et al. | |
| 2006/0141456 A1 | 6/2006 | Edwards et al. | |

(Continued)

FOREIGN PATENT DOCUMENTS

AU    2009290162    4/2010
CA    2 019 559     12/1990

(Continued)

OTHER PUBLICATIONS

Carter P., J Immunol Methods. Feb. 1, 2001;248(1-2):7-15.*
Rudikoff et al., Proc Natl Acad Sci U S A. Mar. 1982;79(6):1979-83.*
Jain et al., "Engineering antibodies for clinical applications," *Trends Biotechnol.*, 25(7):307-16 (2007).
Kufer et al., "A revival of bispecific antibodies," *Trends Biotechnol.*, 22(5):238-44 (2004).
U.S. Appl. No. 14/019,117, filed Sep. 5, 2013, Igawa et al.
U.S. Appl. No. 14/019,712, filed Sep. 5, 2013, Igawa et al.

(Continued)

*Primary Examiner* — Michael Szperka
(74) *Attorney, Agent, or Firm* — Fish & Richardson P.C.

(57) ABSTRACT

Various bispecific antibodies that specifically bind to both blood coagulation factor IX/activated blood coagulation factor IX and blood coagulation factor X and functionally substitute for the cofactor function of blood coagulation factor VIII, that is, the function to promote activation of blood coagulation factor X by activated blood coagulation factor IX, were produced. From these antibodies, multispecific antigen-binding molecules having a high activity of functionally substituting for blood coagulation factor VIII were successfully discovered.

33 Claims, 9 Drawing Sheets

(56) References Cited

U.S. PATENT DOCUMENTS

| | | | |
|---|---|---|---|
| 2006/0159673 A1 | 7/2006 | Kojima | |
| 2006/0160184 A1 | 7/2006 | Hoogenboom et al. | |
| 2006/0204493 A1 | 9/2006 | Huang et al. | |
| 2006/0269989 A1 | 11/2006 | Miyazaki et al. | |
| 2007/0036785 A1 | 2/2007 | Kishimoto et al. | |
| 2007/0041978 A1 | 2/2007 | Hattori et al. | |
| 2007/0054354 A1 | 3/2007 | Humphreys et al. | |
| 2007/0059312 A1 | 3/2007 | Baca et al. | |
| 2007/0087381 A1 | 4/2007 | Kojima | |
| 2007/0110757 A1 | 5/2007 | Wei et al. | |
| 2008/0075712 A1 | 3/2008 | Hattori et al. | |
| 2008/0166756 A1 | 7/2008 | Tsuchiya et al. | |
| 2009/0117097 A1 | 5/2009 | Igawa et al. | |
| 2009/0263392 A1 | 10/2009 | Igawa et al. | |
| 2009/0324589 A1 | 12/2009 | Igawa et al. | |
| 2010/0003254 A1* | 1/2010 | Hattori ............... C07K 16/40 424/136.1 | |
| 2010/0015133 A1 | 1/2010 | Igawa et al. | |
| 2010/0055092 A1 | 3/2010 | Hasegawa et al. | |
| 2010/0239577 A1 | 9/2010 | Igawa et al. | |
| 2010/0291072 A1 | 11/2010 | Lowman et al. | |
| 2010/0298542 A1 | 11/2010 | Igawa et al. | |
| 2011/0076275 A1 | 3/2011 | Igawa et al. | |
| 2011/0111406 A1 | 5/2011 | Igawa et al. | |
| 2011/0236374 A1 | 9/2011 | Shitara et al. | |
| 2011/0245473 A1 | 10/2011 | Igawa et al. | |
| 2012/0237517 A1 | 9/2012 | Hattori et al. | |
| 2013/0011866 A1 | 1/2013 | Igawa et al. | |
| 2013/0018174 A1* | 1/2013 | Igawa et al. ............... 530/387.3 | |
| 2013/0195849 A1 | 8/2013 | Spreter et al. | |
| 2014/0037632 A1 | 2/2014 | Igawa et al. | |
| 2014/0370018 A1 | 12/2014 | Igawa et al. | |
| 2014/0377253 A1 | 12/2014 | Harding et al. | |
| 2015/0284465 A1 | 10/2015 | Igawa et al. | |

FOREIGN PATENT DOCUMENTS

| | | |
|---|---|---|
| CA | 2 331 641 | 11/1999 |
| CA | 2 603 264 | 10/2006 |
| CA | 2 700 986 | 4/2009 |
| CN | 101198698 | 6/2008 |
| CN | 102471378 | 5/2012 |
| EP | 0 369 566 | 5/1990 |
| EP | 0 404 097 | 12/1990 |
| EP | 0 783 893 | 7/1997 |
| EP | 0 811 691 | 12/1997 |
| EP | 1 069 185 | 1/2001 |
| EP | 1 327 681 | 7/2003 |
| EP | 1 505 148 | 2/2005 |
| EP | 1 510 943 | 3/2005 |
| EP | 0 979 281 | 7/2005 |
| EP | 1 605 058 | 12/2005 |
| EP | 1 688 488 | 8/2006 |
| EP | 1 693 448 | 8/2006 |
| EP | 1 220 923 | 6/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 2 006 381 | 12/2008 |
| EP | 2 107 115 | 10/2009 |
| EP | 2 275 443 | 1/2011 |
| JP | S63-52890 | 3/1988 |
| JP | 2-028200 | 1/1990 |
| JP | 2-145187 | 6/1990 |
| JP | 5-501543 | 3/1993 |
| JP | 5-184383 | 7/1993 |
| JP | 5-199894 | 8/1993 |
| JP | 5-203652 | 8/1993 |
| JP | 5-213775 | 8/1993 |
| JP | 5-304992 | 11/1993 |
| JP | 07-67688 | 3/1995 |
| JP | H08-500979 | 2/1996 |
| JP | 8-510555 | 11/1996 |
| JP | 09-506001 | 6/1997 |
| JP | 10-165184 | 6/1998 |
| JP | 10-511085 | 10/1998 |
| JP | 11-500915 | 1/1999 |
| JP | H11-500916 | 1/1999 |
| JP | 11-71288 | 3/1999 |
| JP | 11-506310 | 6/1999 |
| JP | 2001-523971 | 11/2001 |
| JP | 2002-518041 | 6/2002 |
| JP | 2003-055398 | 2/2003 |
| JP | 2003-509049 | 3/2003 |
| JP | 2004-086862 | 3/2004 |
| JP | 2004-511426 | 4/2004 |
| JP | 2005-535341 | 11/2005 |
| JP | 2005-537009 | 12/2005 |
| JP | 2013-165716 | 8/2013 |
| JP | 5334319 | 11/2013 |
| RU | 2266298 | 12/2005 |
| RU | 2339696 | 11/2008 |
| TW | 2007/14313 | 4/2007 |
| WO | WO 91/08770 | 6/1991 |
| WO | WO 92/19759 | 11/1992 |
| WO | WO 93/11161 | 6/1993 |
| WO | WO 94/13804 | 6/1994 |
| WO | WO 95/01571 | 1/1995 |
| WO | WO 95/14710 | 6/1995 |
| WO | WO 95/33844 | 12/1995 |
| WO | WO 96/01653 | 1/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 97/10354 | 3/1997 |
| WO | WO 98/03546 | 1/1998 |
| WO | WO 98/50431 | 11/1998 |
| WO | WO 99/03495 | 1/1999 |
| WO | WO 99/10494 | 3/1999 |
| WO | WO 99/18212 | 4/1999 |
| WO | WO 99/51743 | 10/1999 |
| WO | WO 99/58572 | 11/1999 |
| WO | WO 99/67359 | 12/1999 |
| WO | WO 01/19992 | 3/2001 |
| WO | WO 01/30854 | 5/2001 |
| WO | WO 01/82899 | 11/2001 |
| WO | WO 01/90192 | 11/2001 |
| WO | WO 02/06838 | 1/2002 |
| WO | WO 02/33073 | 4/2002 |
| WO | WO 03/000883 | 1/2003 |
| WO | WO 03/091424 | 1/2003 |
| WO | WO 03/035835 | 5/2003 |
| WO | WO 03/042231 | 5/2003 |
| WO | WO 03/087163 | 10/2003 |
| WO | WO 03/105757 | 12/2003 |
| WO | WO 2004/009618 | 1/2004 |
| WO | WO 2004/016740 | 2/2004 |
| WO | WO 2004/020579 | 3/2004 |
| WO | WO 2004/060919 | 7/2004 |
| WO | WO 04/068931 | 8/2004 |
| WO | WO 2004/065611 | 8/2004 |
| WO | WO 2004/096273 | 11/2004 |
| WO | WO 2004/097041 | 11/2004 |
| WO | WO 2004/111233 | 12/2004 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005035756 A1 * | 4/2005 ......... C07K 16/2866 |
| WO | WO 2005/047327 | 5/2005 |
| WO | WO 2005/067620 | 7/2005 |
| WO | WO 2005/123126 | 12/2005 |
| WO | WO 2006/004663 | 1/2006 |
| WO | WO 2006/030200 | 3/2006 |
| WO | WO 2006/030220 | 3/2006 |
| WO | WO 2006/067913 | 6/2006 |
| WO | WO 2006/106903 | 10/2006 |
| WO | WO 2006/106905 | 10/2006 |
| WO | WO 2006/109592 | 10/2006 |

(56) References Cited

FOREIGN PATENT DOCUMENTS

| WO | WO 2006109592 A1 * | 10/2006 | ............ C07K 16/40 |
|---|---|---|---|
| WO | WO 2007/114319 | 10/2007 | |
| WO | WO 2007/114325 | 10/2007 | |
| WO | WO 2007/142325 | 12/2007 | |
| WO | WO 2008/043822 | 4/2008 | |
| WO | WO 2008/090960 | 7/2008 | |
| WO | WO 2009/041621 | 4/2009 | |
| WO | WO 2009/041643 | 4/2009 | |
| WO | WO 2009/125825 | 10/2009 | |
| WO | WO 2009/139822 | 11/2009 | |
| WO | WO 2010/035769 | 4/2010 | |
| WO | WO 2010/151792 | 12/2010 | |
| WO | WO 2011/078332 | 6/2011 | |
| WO | WO 2011078332 A1 * | 6/2011 | |
| WO | WO 2011/111007 | 9/2011 | |

OTHER PUBLICATIONS

Fay et al., "The size of human factor VIII heterodimers and the effects produced by thrombin," *Biochim Biophys Acta.*, 871(3):268-78 (1986).

Helfrich et al., "A rapid and versatile method for harnessing scFv antibody fragments with various biological effector functions," *J. Immunol. Methods*, 237(1-2):131-45 (2000).

Hoyer, L.W., "The factor VIII complex: structure and function," *Blood*, 58(1):1-13 (1981).

Kerschbaumer et al., "An antibody specific for coagulation factor IX enhances the activity of the intrinsic factor X-activating complex," *J. Biol. Chem.*, 279(39):40445-50 (2004).

Miyazaki et al., "Generation of bispecific IgG, which mimics the cofactor function of blood coagulation factor VIII," *Poster sessions*, (2P-B-161) (2006).

Saito et al., "Factor VIII Mimetic Antibody: (1) Establishment and Characterization of Anti-factor IX/anti-factor X Bispecific Antibodies," *2005 International Society of Thrombosis and Haemostatis*.

Saito et al., "Establishment of Factor VIII Mimetic Antibodies and Their In Vitro Activities in Hemophilia A," *2006 National Hemophilia Foundation Symposia*.

Shima et al., "Factor VIII Mimetic Antibody: (2) In Vitro Assessment of Cofactor Activity in Hemophilia A," *2005 International Society of Thrombosis and Haemostatis*.

Shima, M., "Bispecific antibodies to coagulation factors IXa and X mimic the function of factor VIII," *2006 World Federation of Haemophilia* (Haemophilia 2006:12(Suppl. 2)).

Shirahata, Minna ni yakudatsu ketsuyubyo no kiso to rinsho. Iyaku (Medicine and Drug) Journal Co., Ltd., 280-9 (2009) (English translation).

Vehar et al., "Structure of human factor VIII," *Nature*, 312(5992):337-42 (1984).

Wood et al., "Expression of active human factor VIII from recombinant DNA clones," *Nature*, 312(5992):330-7 (1984).

International Search Report for App. Ser. No. PCT/JP2011/076486, mailed Dec. 27, 2011, 4 pages.

U.S. Appl. No. 10/560,098, filed Apr. 28, 2006, Miyazaki et al.
U.S. Appl. No. 10/575,193, filed Oct. 24, 2006, Hattori et al.
U.S. Appl. No. 10/575,905, filed Apr. 30, 2007, Hattori et al.
U.S. Appl. No. 11/910,128, filed Oct. 7, 2008, Igawa et al.
U.S. Appl. No. 11/910,836, filed Jan. 12, 2009, Hattori et al.
U.S. Appl. No. 12/295,039, filed Jan. 20, 2009, Igawa et al.
U.S. Appl. No. 12/295,075, filed Apr. 20, 2009, Igawa et al.
U.S. Appl. No. 12/679,922, filed Oct. 1, 2010, Igawa et al.
U.S. Appl. No. 13/434,643, filed Mar. 29, 2012, Hattori et al.
U.S. Appl. No. 13/518,861, filed Jun. 22, 2012, Igawa et al.

Hombach et al., "A CD16/CD30 bispecific monoclonal antibody induces lysis of Hodgkin's cells by unstimulated natural killer cells in vitro and in vivo," *Int J Cancer*, 55:830-6 (1993).

Roguska et al., "Humanization of murine monoclonal antibodies through variable domain resurfacing," *Proc Natl Acad Sci U.S.A.*, 91:969-73 (1994).

Staerz et al., "Hybrid hybridoma producing a bispecific monoclonal antibody that can focus effector T-cell activity," *Proc Natl Acad Sci U.S.A.*, 83:1453-7 (1986).

Dahlback, "Blood coagulation," *Lancet*, 355(9215):1627-32 (2000).

Fay et al., "Chapter 2B Nonenzymatic cofactors: factor VIII," *Comprehensive Biochemistry*, 13:35-37 (1986).

Hu et al., "Development and characterization of a novel fusion protein composed of a human IgG1 heavy chain constant region and a single-chain fragment variable antibody against Venezuelan equine encephalitis virus," *J Biochem.*, 133(1):59-66 (2003).

Sampei et al., "Identification and multidimensional optimization of an asymmetric bispecific IgG antibody mimicking the function of factor VIII cofactor activity," *PLoS One*, 2013; 8(2):e57479. Epub: Feb. 28, 2013.

Zuo et al., "An efficient route to the production of an IgG-like bispecific antibody," *Protein Eng.*, 13(5):361-7 (2000).

Bowie et al., "Deciphering the Message in Protein Sequences: Tolerance to Amino Acid Substitutions," *Science*, Mar. 16, 1990;247:1306-1310.

Burgess, "Possible dissociation of the heparin-binding and mitogenic activities of heparin-binding (acidic fibroblast) growth factor-1 from its receptor-binding activities by site-directed mutagenesis of a single lysine residue," *J. Cell. Biol.*, 1990;111:2129-2138.

Kabat et al., Sequence of Proteins of Immunological Interest, 5$^{th}$ Edition 1991, p. 690 and p. 693.

Lazar et al., "Transforming growth factor alpha: mutation of aspartic acid 47 and leucine 48 results in different biological activities," *Mol. Cell Biol.*, 1988;8:1247-1252.

Medesan et al., "Delineation of the amino acid residues involved in transcytosis and catabolism of mouse IgGl," *J Immunol.*, Mar. 1, 1997;158(5):2211-7.

Pan et al., "Blocking neuropilin-1 function has an additive effect with anti-VEGF to inhibit tumor growth," *Cancer Cell*, Jan. 2007;11(1):53-67.

Singer et al., Genes & Genomes, 1991; 67-69.

Singer et al., Genes & Genomes, 1998;1:63-64.

Lindsay, "Chapter 4: Determination of the Kinetics and Mechanism of tg-FIX Activation by Factor XIa," 49-75 (2004).

USPTO Restriction Requirement in U.S. Appl. No. 14/019,712, dated Nov. 18, 2013, 8 pages.

Fish & Richardson P.C., Response to Restriction Requirement dated Nov. 18, 2013 in U.S. Appl. No. 14/019,712, filed on Dec. 6, 2013, 2 pages.

USPTO Non-Final Office Action in U.S. Appl. No. 14/019,712, dated Jan. 17, 2014, 16 pages.

Fish & Richardson P.C., Response to Non-Final Office Action in U.S. Appl. No. 14/019,712, filed on Apr. 18, 2014, 9 pages.

USPTO Final Office Action in U.S. Appl. No. 14/019,712, dated May 27, 2014, 9 pages.

Bowen, Haemophilia A and haemophilia B: molecular insights, *Mol Pathol.*, Feb. 2002;55(1):1-18.

Brandstetter et al., "X-ray structure of clotting factor IXa: active site and module structure related to Xase activity and hemophilia B," *Proc Natl Acad Sci U S A*, Oct. 10, 1995;92(21):9796-800.

De Pascalis et al., "Grafting of 'abbreviated' complementary-determining regions containing specificity-determining residues essential for ligand contact to engineer a less immunogenic humanized monoclonal antibody," *Journal of Immunology*, Sep. 15, 2002;169(6):3076-3084.

Fay, "Activation of factor VIII and mechanisms of cofactor action," *Blood Rev.*, Mar. 2004;18(1):1-15.

Gonzales et al., "Minimizing the immunogenicity of antibodies for clinical application," *Tumour Biol.*, Jan.-Feb. 2005;26(1):31-43.

Iwahashi et al., "CDR substitutions of a humanized monoclonal antibody (CC49): contributions of individual CDRs to antigen binding and immunogenicity," *Mol Immunol.*, Oct.-Nov. 1999;36(15-16):1079-91.

Jirholt et al., "Exploiting sequence space: shuffling in vivo formed complementarity determining regions into a master framework," *Gene.*, Jul. 30, 1998;215(2):471-6.

Schmidt et al., "Structure-function relationships in factor IX and factor IXa," *Trends Cardiovasc Med.*, Jan. 2003;13(1):39-45.

(56) References Cited

OTHER PUBLICATIONS

Tamura et al., "Structural correlates of an anticarcinoma antibody: identification of specificity-determining residues (SDRs) and development of a minimally immunogenic antibody variant by retention of SDRs only," *J Immunol.*, Feb. 1, 2000;164(3):1432-41.

Notice of Opposition against EP 1 876 236, dated May 20, 2015, in the name of Chugai Seiyaku Kabushiki Kaisha brought by Novo Nordisk A/S, 23 pages.

Notice of Opposition against EP 1 876 236, dated May 22, 2015, in the name of Chugai Seiyaku Kabushiki Kaisha brought by Baxalta Innovations GmbH, 37 pages.

Chugai Seiyaku Kabushiki Kaisha's letter dated Jun. 12, 2013, regarding oral proceedings scheduled on Jun. 26, 2013, in App. Ser. No. EP 06 73 0769.4-1412.

Allard et al., "Antigen binding properties of highly purified bispecific antibodies," *Mol Immunol.*, Oct. 1992;29(10):1219-27.

Haagen et al., "Unprimed CD4+ and CD8+ T cells can be rapidly activated by a CD3×CD19 bispecific antibody to proliferate and become cytotoxic," *Cancer Immunol Immunother.*, Dec. 1994;39(6):391-6.

IMGT Scientific charts depicting the correspondence between Eu and Kabat numbering for the human IgG constant region, created May 17, 2001 and last updated Aug. 13, 2014.

Lloyd et al., "The production of a bispecific anti-CEA, anti-hapten (4-amino-phthalate) hybrid-bybridoma," *J Natl Med Assoc.*, Oct. 1991:83(10):901-4.

Jackman et al., "Development of a two-part strategy to identify a therapeutic human bispecific antibody that inhibits IgE receptor signaling," *J Biol Chem.*, Jul. 2, 2010;285(27): 20850-9. doi: 10.1074/jbc.M110.113910. Epub May 5, 2010.

Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).

Spiess et al., "Bispecific antibodies with natural architecture produced by co-culture of bacteria expressing two distinct half-antibodies," Nat Biotechnol., Aug. 2013; 31(8):753-8. doi: 10.1038/nbt. 2621. Epub Jul. 7, 2013.

U.S. Appl. No. 14/921,590, filed Oct. 23, 2015, Hattori et al.

Arndt et al., "Factors influencing the dimer to monomer transition of an antibody single-chain Fv fragment," *Biochemistry*, Sep. 15, 1998;37(37):12918-26.

Chatellier et al., "Functional mapping of conserved residues located at the VL and VH domain interface of a Fab," *J. Mol. Biol.*, Nov. 22, 1996;264(1):1-6.

Davies et al., "Antibody VH domains as small recognition units," *Biotechnology (N.Y.)*, May 1995;13(5):475-9.

Griffin et al., "Analysis of heavy and light chain sequences of conventional camelid antibodies from *Camelus dromedarius* and *Camelus bactrianus* species," *J Immunol Methods*, Mar. 2014;405:35-46. doi: 10.1016/j.jim.2014.01.003. Epub Jan. 18, 2014.

Hamers-Casterman et al., "Naturally occurring antibodies devoid of light chains," *Nature*, Jun. 3, 1993;363(6428):446-8.

Hozumi et al., "Evidence for somatic rearrangement of immunoglobulin genes coding for variable and constant regions," *Proc Natl Acad Sci U S A.*, Oct. 1976;73(10):3628-32.

Igawa et al., "VH/VL interface engineering to promote selective expression and inhibit conformational isomerization of thrombopoietin receptor agonist single-chain diabody," *Protein Eng Des Sel.*, Aug. 2010;23(8):667-77. doi: 10.1093/protein/gzq034. Epub Jun. 24, 2010.

Jung et al., "The importance of framework residues H6, H7 and H10 in antibody heavy chains: experimental evidence for a new structural subclassification of antibody V(H) domains," *J. Mol. Biol.*, Jun. 8, 2001;309(3):701-16.

Kabsch et al., "On the use of sequence homologies to predict protein structure: identical pentapeptides can have completely different conformations," *Proc Natl Acad Sci U S A.*, Feb. 1984;81(4):1075-8.

Kenanova et al., "Tailoring the pharmacokinetics and positron emission tomography imaging properties of anti-carcinoembryonic antigen single-chain Fv-Fc antibody fragments," *Cancer Res.*, Jan. 15, 2005;65(2):622-31.

Khalifa et al.; "Effects on interaction kinetics of mutations at the VH-VL interface of Fabs depend on the structural context," *J. Mol. Recognit.*, May-Jun. 2000;13(3):127-39.

Kipriyanov et al., "Bispecific tandem diabody for tumor therapy with imprived antigen binding and pharmacokinetics," *J Mol Biol.*, Oct. 15, 1999;293(1):41-56.

Kipriyanov et al., "Effect of Domain Order on the Activity of Bacterially Produced Bispecific Single-chain Fv Antibodies," *J Mol Biol.*, Jun. 27, 2003;330(1):99-111.

Kontermann, R., "Recombinant bispecific antibodies for cancer therapy," *Acta Pharmacol Sin.*, Jan. 2005;26(1):1-9.

Korn et al., "Recombinant bispecific antibodies for the targeting of adenoviruses to CEA-expressing tumour cells: a comparative analysis of bacterially expressed single-chain diabody and tandem scFv," *J Gene Med.*, Jun. 2004;6:642-51.

Kumar et al., "The second PDZ domain of INAD is a type I domain involved in binding to eye protein kinase C. Mutational analysis and naturally occuring variants," *J. Biol. Chem.*, Jul. 6, 2001;276(27):24971-7. Epub May 7, 2001.

Le Gall et al., "Effect of linker sequences between the antibody variable domains on the formation, stability and biological activity of a bispecific tandem diabody," *Protein Eng Des Sel.*, Apr. 2004;17(4):357-66. Epub May 4, 2004.

Lebégue et al., "Production and characterization of hybrid monoclonal antibodies with IgG1/IgG3 double isotype," *C R Acad Sci III.*, 1990;310(9):377-82.

Liu et al., "Functional interactions between arginine-133 and aspartate-88 in the human reduced folate carrier: evidence for a charge-pair association," *Biochem. J.*, Sep. 1, 2001;358(Pt 2):511-6.

Maity et al., "Equilibrium unfolding of dimeric and engineered monomeric forms of Cro (F58W) repressor and the effect of added salts: evidence for the formation of folded monomer induced by sodium perchlorate," *Arch Biochem Biophys.*, Feb. 1, 2005;434(1):93-107.

Male et al., "Antibodies" *Immunology*, 7th Edition (2006), published by Elsevier Ltd., pp. 59-86.

Michaelsen et al., "A mutant human IgG molecule with only one Clq binding site can activate complement and induce lysis of target cells," *Eur J Immunol.*, Jan. 2006;36(1):129-38.

Narhi et al., "Asn to Lys mutations at three sites which are N-glycosylated in the mammalian protein decrease the aggregation of *Escherichia coli*-derived erythropoietin," *Protein Eng.*, Feb. 2001;14(2):135-40.

Nieba et al., "Disrupting the hydrophobic patches at the antibody variable/constant domain interface: improved in vivo folding and physical characterization of an engineered scFv fragment," *Protein Eng.*, Apr. 1977;10(4):435-44.

Nohaile et al., "Altering dimerization specificity by changes in surface electrostatics," *Pro Natl Acad Sci U S A.*, Mar. 13, 2001;98(6):3109-14. Epub Feb. 27, 2001.

O'Shea et al., "Peptide 'Velcro': design of a heterodimeric coiled coil," *Curr Biol.*, Oct. 1, 1993;3(10):658-67.

Peipp et al., "Bispecific antibodies targeting cancer cells," *Biochem. Soc. Trans.*, Aug. 2002;30:507-511.

Pokkuluri et al., "A domain flip as a result of a single amino-acid substitution," *Structure*, Aug. 15, 1998;6(8):1067-73.

Roitt et al., *Immunology, M., Mir*, 5th Edition (2000), pp. 97-113.

Skerra, "Use of the tetracycline promoter for the tightly regulated production of a murine antibody fragment in *Escherichia coli*," *Gene*, Dec. 30, 1994;151(1-2):131-5.

Tan et al., "Contributions of a highly conserved $V_H/V_L$ hydrogen bonding interaction to scFv folding stability and refolding efficiency," *Biophys J.*, Sep. 1998; 75(3):1473-82.

Vargas-Madrazo et al., "An improved model of association for VH-VL immunoglobulin domains: asymmetries between VH and VL in the packing of some interface residues," *J. Mol. Recognit.*, May-Jun. 2003;16(3):113-20.

(56) References Cited

OTHER PUBLICATIONS

Wang et al., "Conserved amino acid networks involved in antibody variable domain interactions," *Proteins*, Jul. 2009;76(1):99-114. doi: 10.1002/prot.22319.
Worn et al., "Stability engineering of antibody single-chain Fv fragments," *J Mol Biol.*, Feb. 2, 2001;305(5):989-1010.
Wu et al., "Multimerization of a chimeric anti-CD20 single-chain Fv-Fc fusion protein is mediated through variable domain exchange," *Protein Eng.*, Dec. 2001;14(12):1025-33.
Yasukawa et al., "Structure and expression of human B cell stimulatory factor-2 (BSF-2/IL-6) gene," *EMBO J*, Oct. 1987;6(10):2939-45.
Zhu et al., "Remodeling domain interfaces to enhance heterodimer formation," *Protein Sci.*, Apr. 1997;6(4):781-8.
"National Haemophilia Foundation (NHF) Medical and Scientific Advisory Council (MASAC) Recommendations Concerning Prophylaxis," *MedicalBulletin*, No. 193, 1 page (1994).
Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).
Adams et al., "Humanization of a recombinant monoclonal antibody to produce a therapeutic HER dimerization inhibitor, pertuzumab," *Cancer Immunol. Immunother.*, 55:717-727 (2006).
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).
Almagro et al., "Humanization of antibodies," *Front Biosci.*, 13:1619-33 (2008).
Amersham Biosciences, "Protein Purification Handbook," Edition AC, 98 pages (2001).
Amersham Biosciences, "Affinity Chromatography: Principles and Methods," Edition AD, pp. 16-18, 137 (2002).
Angal et al., "A single amino acid substitution abolishes the heterogeneity of chimeric mouse/human (IgG4) antibody," *Mol. Immunol.*, 30:105-108 (1993).
Armour et al., "Recombinant human IgG molecules lacking Fcgamma receptor I binding and monocyte triggering activities," *Eur. J. Immunol.*, 29(8):2613-24 (1999).
Arndt et al., "Helix-stabilized Fv (hsFv) antibody fragments: substituting the constant domains of a Fab fragment for a heterodimeric coiled-coil domain," *J. Mol. Biol.*, 312:221-228 (2001).
Aslan et al., "Engineering a novel, stable dimeric streptavidin with lower isoelectric point," *J. Biotechnol.*, 128(2):213-25 (2007).
Asselta et al., "Factor V Deficiency," *Semin. Thromb. Hemost.*, 35:382-389 (2009).
Association of Hemophilia Clinic Directors of Canada, "Hemophilia and Von Willebrand's disease: 2. Management Association of Hemophilia Clinic Directors of Canada," *Canadian Medical Association Journal*, 153(2):147-157 (1995).
Atwell et al., "Stable heterodimers from remodeling the domain interface of a homodimer using a phage display library," *J. Mol. Biol.*, 270:26-35 (1997).
Baerga-Ortiz et al., "Two different proteins that compete for binding to thrombin have opposite kinetic and thermodynamic profiles," *Protein Sci.*, 13(1):166-76 (2004).
Bajaj et al., "A Monoclonal Antibody to Factor IX That Inhibits the Factor VIII:Ca Potentiation of Factor X Activation," *J. Biol. Chem.*, 260(21):11574-11580 (1985).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bayry et al., "Immuno affinity purification of foot and mouth disease virus type specific antibodies using recombinant protein adsorbed to polystyrene wells," *J. Virol. Methods*, 81:21-30 (1999).

Bebbington et al., "High-Level Expression of a Recombinant Antibody from Myeloma Cells Using a Glutamine Synthetase Gene as an Amplifiable Selectable Marker," *Biotechnology (N Y)*, 10:169-175 (1992).
Bender et al., "Immunogenicity, efficacy and adverse events of adalimumab in RA patients," *Rheumatol. Int.*, 27:269-274 (2007).
Bessos et al., "The characterization of a panel of monoclonal antibodies to human coagulation factor IX," *Thrombosis Research*, 40:863-867 (1985).
Binz et al., "Engineering novel binding proteins from nonimmunoglobulin domains," *Nat. Biotechnol.*, 23:1257-68 (2005).
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," *J. Immunol.*, 157:3250-59 (1996).
Bolton-Maggs et al., "Haemophilias A and B," *The Lancet*, 361:1801-1809 (2003).
Bos et al., "Enhanced Transfection of a Bacterial Plasmid into Hybridoma Cells by Electroporation: Application for the Selection of Hybrid Hybridoma (Quadroma) Cell Lines," *Hybridoma*, 11:41-51 (1992).
Branden and Tooze, "Recognition of Foreign Molecules by the Immune System," *Introduction to Protein Structure, 2d Ed.*, Garland Publishing, pp. 299-323 (1999).
Brennan et al., "Preparation of Bispecific Antibodies by Chemical Recombination of Monoclonal Immunoglobulin G1 Fragments," *Science*, 229:81-83 (1985).
Brinkman et al. "Phospholipid-binding domain of factor VIII is involved in endothelial cell-mediated activation of factor X by factor IXa," *Arterioscler. Thromb. Vasc. Biol.*, 22(3):511-516 (2002).
Brown et al., "Tolerance of single, but not multiple, amino acid replacements in antibody $V_H$CDR 2: a means of minimizing B cell wastage from somatic hypermutation?," *J. Immunol.*, 156(9):3285-91 (1996).
Burges et al., "Effective relief of malignant ascites in patients with advanced ovarian cancer by a trifunctional anti-EpCAM × anti-CD3 antibody: a phase I/II study," *Clin. Cancer Res.*, 13(13):3899-905 (2007).
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter, "Bispecific human IgG by design," *J. Immunol. Methods*, 248:7-15 (2001).
Chamow et al., "A humanized, bispecific immunoadhesin-antibody that retargets CD3+ effectors to kill HIV-1-infected cells," *J. Immunol.*, 153(9):4268-80 (1994).
Chau et al., "HuM291(Nuvion), a humanized Fc receptor-nonbinding antibody against CD3, anergizes peripheral blood T cells as partial agonist of the T cell receptor," *Transplantation.*, 71(7):941-50 (2001).
Chen et al., "Generation and analysis of random point mutations in an antibody CDR2 sequence: many mutated antibodies lose their ability to bind antigen," *J. Exp. Med.*, 176(3):855-66 (1992).
Chen et al., "Defective secretion of an immunoglobulin caused by mutations in the heavy chain complementarity determining region 2," *J. Exp. Med.*, 180(2):577-86 (1994).
Chirino et al., "Minimizing the immunogenicity of protein therapeutics," *Drug Discov. Today.*, 9:82-90 (2004).
Chu et al., "Accumulation of succinimide in a recombinant monoclonal antibody in mildly acidic buffers under elevated temperatures," *Pharm. Res.*, 24(6):1145-56 (2007).
Cole et al., "Human IgG2 variants of chimeric anti-CD3 are nonmitogenic to T cells," *J. Immunol.*, 159(7):3613-21 (1997).
Comper et al., "Charge selectivity in kidney ultrafiltration," *Kidney Int.*, 47:1242-51 (1995).
Cordoba et al., "Non-enzymatic hinge region fragmentation of antibodies in solution," *J. Chromatogr. B. Analyt. Technol. Biomed. Life Sci.*, 818(2):115-21 (2005).
Couto et al., "Anti-BA46 Monoclonal Antibody Mc3: Humanization Using a Novel Positional Consensus and in Vivo and in Vitro Characterization," *Cancer Res.*, 55:1717-22 (1995).

(56) References Cited

OTHER PUBLICATIONS

Dall'Acqua et al., "Antibody humanization by framework shuffling," *Methods*, 36(1):43-60 (2005).
Damschroder et al., "Framework shuffling of antibodies to reduce immunogenicity and manipulate functional and biophysical properties," *Mol. Immunol.*, 44(11):3049-60 (2007).
Davie et al., "The coagulation cascade: Initiation, maintenance, and regulation," *Biochemistry*, 30(43):10363-10370 (1991).
De Groot et al., "De-immunization of therapeutic proteins by T-cell epitope modification," *Dev. Biol. (Basel)*, 122:171-94 (2005).
Deen et al., "Structural determinants of glomerular permeability," *Am. J. Physiol. Renal. Physiol.*, 281:F579-F596 (2001).
Del Rio et al., "An Engineered Penicillin Acylase with Altered Surface Charge Is More Stable in Alkaline pH," *Ann. NY Acad. Sci.*, 799:61-64 (1996).
Deng et al., "An Agonist Murine Monoclonal Antibody to the Human c-Mpl Receptor Stimulates Megakaryocytopoiesis," *Blood*, 92:1981-88 (1998).
Dillon et al., "Structural and functional characterization of disulfide isoforms of the human IgG2 subclass," *J. Biol. Chem.*, 283:16206-15 (2008).
Dumont et al., "Monomeric Fc fusions: impact on pharmacokinetic and biological activity of protein therapeutics," *BioDrugs.*, 20(3):151-60 (2006).
Ewert et al., "Stability improvement of antibodies for extracellular and intracellular applications: CDR grafting to stable frameworks and structure-based framework engineering," *Methods*, 34:184-199 (2004).
Francois et al., "Construction of a Bispecific Antibody Reacting with the α- and β-Chains of the Human IL-2 Receptor," *J. Immunol.*, 150:4610-4619 (1993).
Fujii, "Antibody affinity maturation by random mutagenesis," *Methods Mol. Biol.*, 248:345-59 (2004).
GenPept Accession No. AAC26541, "anti BoNT/A Hc scFv antibody [synthetic construct]," 1 page (Aug. 1, 2001).
Gelderman et al., "The inhibitory effect of CD46, CD55, and CD59 on complement activation after immunotherapeutic treatment of cervical carcinoma cells with monoclonal antibodies or bispecific monoclonal antibodies," *Lab Invest.*, 82(4):483-93 (2002).
Gerstner et al., "Sequence plasticity in the antigen-binding site of a therapeutic anti-HER2 antibody," *J. Mol. Biol.*, 321(5):851-62 (2002).
Gessner et al., "The IgG Fc receptor family," *Ann. Hematol.*, 76:231-248 (1998).
Ghetie et al., "FcRn: the MHC class I-related receptor that is more than an IgG transporter," *Immunol. Today*, 18:592-598 (1997).
Ghetie et al., "Increasing the serum persistence of an IgG fragment by random mutagenesis," *Nat. Biotechnol.*, 15:637-640 (1997).
Ghetie et al., "Multiple roles for the major histocompatibility complex class I-related receptor FcRn," *Annu. Rev. Immunol.*, 18:739-766 (2000).
Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).
Goode et al., "The glomerular basement membrane charge-selectivity barrier: an oversimplified concept?" *Nephrol. Dial. Transplant.*, 11:1714-16 (1996).
Graves et al., "Molecular modeling and preclinical evaluation of the humanized NR-LU-13 antibody," *Clin. Cancer Res.*, 5:899-908 (1999).
Grosse-Hovest et al., "A recombinant bispecific single-chain antibody induces targeted, supra-agonistic CD28-stimulation and tumor cell killing", *European Journal of Immunology*, 33(5):1334-1340 (2003).
Gunasekaran et al., "Enhancing antibody Fc heterodimer formation through electrostatic steering effects: applications to bispecific molecules and monovalent IgG," *J. Biol. Chem.*, 285(25):19637-46 (2010).
Gupta et al., "Affinity chromatography and co-chromatography of bispecific monoclonal antibody immunoconjugates," *J. Biochem. Biophys. Methods*, 51:203-216 (2002).
Guyre et al., "Increased potency of Fc-receptor-targeted antigens," *Cancer Immunol. Immunother.*, 45(3-4):146-8 (1997).
Hämmerling et al., "Use of Hybrid Antibody with Anti-γG and Anti-Ferritin Specificities in Locating Cell Surface Antigens by Electron Microscopy," *J. Exp. Med.*, 128:1461-1473 (1968).
Hanson et al., "Catalytic antibodies and their applications," *Curr. Opin. Biotechnol.*, 16:631-636 (2005).
He et al., "Humanization and pharmacokinetics of a monoclonal antibody with specificity for both E- and P-selectin," *J. Immunol.*, 160:1029-35 (1998).
Hinton et al., "An engineered human IgG1 antibody with longer serum half-life," *J. Immunol.*, 176:346-356 (2006).
Hinton et al., "Engineered human IgG antibodies with longer serum half-lives in primates," *J. Biol. Chem.*, 279(8):6213-6 (2004).
Hoad et al. "Characterization of monoclonal antibodies to human factor X.Xa: Initial observations with a quantitative ELISA procedure," *J. Immunol. Methods*, 136(2):269-278 (1991).
Holliger et al., "'Diabodies': Small bivalent and bispecific antibody fragments," *Proc. Natl. Acad. Sci. USA*, 90:6444-6448 (1993).
Hsia et al., "Treatment of acquired factor X inhibitor by plasma exchange with concomitant intravenous immunoglobulin and corticosteroids," *Am. J Hematol.*, 83:318-320 (2008).
Huse et al., "Generation of a Large Combinatorial Library of the Immunoglobulin Repertoire in Phage Lambda," *Science*, 246:1275-1281 (1989).
Hwang et al., "Use of human germline genes in a CDR homology-based approach to antibody humanization," *Methods*, 36:35-42 (2005).
Igawa et al., "Engineering the variable region of therapeutic IgG antibodies," *MAbs*, 3(3):243-52 (2011).
Igawa et al., "Reduced elimination of IgG antibodies by engineering the variable region," *Protein Eng. Des. Sel.*, 23(5):385-92 (2010).
Igawa et al., "Antibody recycling by engineered pH-dependent antigen binding improves the duration of antigen neutralization," *Nat. Biotechnol.*, 28(11):1203-7 (2010).
Ito et al., "The His-probe method: effects of histidine residues introduced into the complementarity-determining regions of antibodies on antigen-antibody interactions at different pH values," *FEBS Lett.*, 309:85-88 (1992).
Janeway et al., "Structure of the Antibody Molecule and Immunoglobulin Genes," *Immunobiology*, $3^{rd}$ Edition, Garland Press, 3:1-3:11 (1997).
Jendeberg et al., "Engineering of Fc(1) and Fc(3) from human immunoglobulin G to analyse subclass specificity for staphylococcal protein A," *J. Immunol. Methods*, 201(1):25-34 (1997).
Johnson et al., "Cation exchange-HPLC and mass spectrometry reveal C-terminal amidation of an IgG1 heavy chain," *Anal. Biochem.*, 360:75-83 (2007).
Jones et al., "Identification and removal of a promiscuous CD4+ T cell epitope from the C1 domain of factor VIII," *Thromb. Haemost.*, 3:991-1000 (2005).
Kang et al., "Linkage of recognition and replication functions by assembling combinatorial antibody Fab libraries along phage surfaces," *Proc. Natl. Acad. Sci. USA*, 88:4363-4366 (1991).
Karpovsky et al., "Production of Target-Specific Effector Cells Using Hetero—Cross-Linked Aggregates Containing Anti-Target Cell and Anti-Fcγ Receptor Antibodies," *J. Exp. Med.*, 160:1686-1701 (1984).
Kashmiri et al., "Generation, characterization, and in vivo studies of humanized anticarcinoma antibody CC49," *Hybridoma*, 14:461-473 (1995).
Katayose et al., "MUC1-specific targeting immunotherapy with bispecific antibodies: inhibition of xenografted human bile duct carcinoma growth," *Cancer Res.*, 56(18):4205-12 (1996).
Khawli et al., "Improved tumor localization and radioimaging with chemically modified monoclonal antibodies," *Cancer. Biother. Radiopharm.*, 11:203-215 (1996).
Kim et al., "Antibody Engineering for the Development of Therapeutic Antibodies," *Mol. Cells*, 20:17-29 (2005).

(56) References Cited

OTHER PUBLICATIONS

Kim et al., "Chemical modification to reduce renal uptake of disulfide-bonded variable region fragment of anti-tac monoclonal antibody labeled with 99mTc," *Bioconjugate Chem.*, 10:447-453 (1999).

Kim et al., "Lowering of pI by acylation improves the renal uptake of 99mTc-labeled anti-Tac dsFv: effect of different acylating reagents," *Nucl. Med. Biol.*, 29:795-801 (2002).

Kim et al., "Mapping the site on human IgG for binding of the MHC class I-related receptor, FcRn," *Eur. J. Immunol.*, 29(9):2819-25 (1999).

Kim et al., "Mammalian type I interferon receptors consists of two subunits: IFNaR1 and IFNaR2," *Gene*, 196:279-286 (1997).

Kobayashi et al., "A monoclonal antibody specific for a distinct region of hen egg-white lysozyme," *Mol. Immunol.*, 19:619-30 (1982).

Kobayashi et al., "The pharmacokinetic characteristics of glycolated humanized anti-Tac Fabs are determined by their isoelectric points," *Cancer Res.*, 59:422-430 (1999).

Komissarov et al., "Site-specific mutagenesis of a recombinant anti-single-stranded DNA Fab. Role of heavy chain complementarity-determining region 3 residues in antigen interaction," *J. Biol. Chem.*, 272(43):26864-70 (1997).

Kranenborg et al., "Development and characterization of anti-renal cell carcinoma x antichelate bispecific monoclonal antibodies for two-phase targeting of renal cell carcinoma," *Cancer Res.*, 55:5864s-5867s (1995).

Kreutz et al., "Efficient bispecific monoclonal antibody purification using gradient thiophilic affinity chromatography," *J. Chromatogr. B*, 714:161-170 (1998).

Kroesen et al., "Phase I study of intravenously applied bispecific antibody in renal cell cancer patients receiving subcutaneous interleukin 2," *Br. J Cancer*, 70:652-661 (1994).

Kurfis et al., "Role of Arg182 in the second extracellular loop of angiotensin II receptor AT2 in ligand binding," *Biochem. Biophys. Res. Commun.*, 263:816-819 (1999).

Kurokawa et al., "Enhanced Fibrinolysis by a Bispecific Monoclonal Antibody Reactive to Fibrin and Tissue Plasminogen Activator," *Bio/Technology*, 7:1163-1167 (1989).

Lansdorp et al., "Purification and analysis of bispecific tetrameric antibody complexes," *Mol. Immunol.*, 27:659-666 (1990).

Lapan et al., "Interaction of the A1 Subunit of Factor VIIIa and the Serine Protease Domain of Factor X Identified by Zero-length Cross-linking," *Thromb. Haemost.*, 80:418-422 (1998).

Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," *J. Nucl. Med.*, 34:1662-1671 (1993).

Lenting et al., "The life cycle of coagulation factor VIII in view of its structure and function", Blood 92(11):3983-3996 (1998).

Leong et al., "Adapting pharmacokinetic properties of a humanized anti-interleukin-8 antibody for therapeutic applications using site-specific pegylation," *Cytokine*, 16(3):106-19 (2001).

Life Technologies (Invitrogen: "ecdysone analogue" and pIND plasmid), Aug. 10, 2012, 2 pages.

Lindhofer et al., "Preferential Species-Restricted Heavy/Light Chain Pairing in Rat/Mouse Quadromas," *J. Immunol.*, 155:219-225 (1995).

Link et al., "Production and Characterization of a Bispecific IgG Capable of Inducing T-Cell-Mediated Lysis of Malignant B Cells," *Blood*, 81:3343-3349 (1993).

Liu et al., "Heterogeneity of monoclonal antibodies," *J. Pharm. Sci.*, 97(7):2426-47 (2008).

Lobo et al., "Antibody pharmacokinetics and pharmacodynamics," *J. Pharm. Sci.*, 93:2645-68 (2004).

Löfqvist et al., "Haemophilia prophylaxis in young patients—a long-term follow-up," *J. Intern. Med.*, 241:395-400 (1997).

Lu et al., "Di-diabody: a novel tetravalent bispecific antibody molecule by design," *J. Immunol. Methods*, 279:219-232 (2003).

Lu et al., "Fab-scFv fusion protein: an efficient approach to production of bispecific antibody fragments," *J. Immunol. Methods*, 267:213-226 (2002).

MacCallum et al., "Antibody-antigen interactions: contact analysis and binding site topography," *J. Mol. Biol.*, 262:732-45 (1996).

Maeda et al., "pH-dependent receptor/ligand dissociation as a determining factor for intracellular sorting of ligands for epidermal growth factor receptors in rat hepatocytes," *J. Control Release*, 82(1):71-82 (2002).

Maini et al., "Double-blind randomized controlled clinical trial of the interleukin-6 receptor antagonist, tocilizumab, in European patients with rheumatoid arthritis who had an incomplete response to methotrexate," *Arthritis Rheum.*, 54:2817-29 (2006).

Manz et al., Bioanalytical Chemistry, World Scientific Publishing Co. (2003).

Manzke et al., "Single-step purification of bispecific monoclonal antibodies for immunotherapeutic use by hydrophobic interaction chromatography," *J. Immunol. Methods*, 208:6573 (1997).

Marti et al., "Inverse electrostatic effect: electrostatic repulsion in the unfolded state stabilizes a leucine zipper," *Biochemistry*, 43(39):12436-47 (2004).

Martin et al., "Crystal structure at 2.8 A of an FcRn/heterodimeric Fc complex: mechanism of pH-dependent binding," *Mol. Cell*, 7:867-877 (2001).

Marvin et al., "Recombinant approaches to IgG-like bispecific antibodies," *Acta. Pharmacol. Sin.*, 26:649-658 (2005).

Marvin et al., "Redesigning an antibody fragment for faster association with its antigen," Biochemistry, 42:7077-83 (2003).

Massino et al., "Quantitative analysis of the products of IgG chain recombination in hybrid hybridomas based on affinity chromatography and radioimmunoassay," *J. Immunol. Methods*, 201:57-66 (1997).

Maxfield et al., "Endocytic recycling," *Nat. Rev. Mol. Cell Biol.*, 5(2):121-32 (2004).

McCafferty et al., "Phage antibodies: filamentous phage displaying antibody variable domains," *Nature*, 348:552-554 (1990).

Menegatti et al., "Factor X Deficiency," *Semin. Thromb. Hemost.*, 35:407-415 (2009).

Merchant et al., "An efficient route to human bispecific IgG," *Nat. Biotechnol.*, 16:677-681 (1998).

Mertens et al., "Factor VIII-Factor IX Interactions: Molecular Sites Involved in Enzyme-Cofactor Complex Assembly," *Thromb. Haemost.*, 82:209-217 (1999).

Milstein et al., "Hybrid hybridomas and their use in immunohistochemistry," *Nature*, 305:537-540 (1983).

Morell et al., "Metabolic properties of IgG subclasses in man," *J. Clin. Invest.*, 49(4):673-80 (1970).

Morimoto et al., "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Methods*, 24:107-117 (1992).

Murtaugh et al., "A combinatorial histidine scanning library approach to engineer highly pH-dependent protein switches," *Protein Sci.*, 20(9):1619-31 doi:10.1002/pro 696 (2011).

Nesterova et al., "Glypican-3 as a novel target for an antibody-drug conjugate," AACR Abstract No. 656, Los Angeles, CA (Apr. 4-18, 2007).

Nilsson et al., "Induction of split tolerance and clinical cure in high-responding hemophiliacs with factor IX antibodies," *Proc. Natl. Acad. Sci. USA*, 83:9169-9173 (1986).

Nilsson et al., "Twenty-five years' experience of prophylactic treatment in severe haemophilia A and B," *J. Intern. Med.*, 232:25-32 (1992).

Nishimoto et al., "Humanized anti-interleukin-6 receptor antibody treatment of multicentric Castleman disease," *Blood*, 106:2627-32 (2005).

Nishimoto et al., "Interleukin 6: from bench to bedside," *Nat. Clin. Pract. Rheumatol.*, 2:619-626 (2006).

Nitta et al., "Preliminary trial of specific targeting therapy against malignant glioma," *Lancet*, 335:368-371 (1990).

(56) References Cited

OTHER PUBLICATIONS

Okubo et al. "The production and characterization of four monoclonal antibodies to human factor X," *Nara Med Assoc.*, 38(1):20-28 (1987).

Onda et al., "Lowering the Isoelectric Point of the Fv Portion of Recombinant Immunotoxins Leads to Decreased Nonspecific Animal Toxicity without Affecting Antitumor Activity," *Cancer Res.*, 61:5070-77 (2001).

Ono et al., "The humanized anti-HM1.24 antibody effectively kills multiple myeloma cells by human effector cell-mediated cytotoxicity," *Mol. Immunol.*, 36(6):387-95 (1999).

Ozhegov et al., Tolkovyi Slovar Russkogo iazyka: 2004, p. 292 (with an English translation of the relevant passage defining "control").

Pakula et al., "Genetic Analysis of Protein Stability and Function," *Annu. Rev. Genet.*, 23:289-310 (1989).

Panka et al., "Variable region framework differences result in decreased or increased affinity of variant anti-digoxin antibodies," *Proc. Natl. Acad. Sci. USA*, 85(9):3080-84 (1988).

Pardridge et al., "Enhanced endocytosis in cultured human breast carcinoma cells and in vivo biodistribution in rats of a humanized monoclonal antibody after cationization of the protein," *J. Pharmacol. Exp. Ther.*, 286(1):548-54 (1998).

Paul, William ed., *Fundamental Immunology*, $3^{rd}$ *edition*, p. 242 (1993).

Pavlinkova et al., "Charge-modified single chain antibody constructs of monoclonal antibody CC49: Generation, characterization, pharmacokinetics, and biodistribution analysis," *Nucl. Med. Biol.*, 26:27-34 (1999).

Pavlou et al., "The therapeutic antibodies market to 2008," *Eur. J. Pharm. Biopharm.*, 59:389-396 (2005).

Piper et al., "Interferon therapy in primary care," *Primary Care Update for Ob/Gyns*, 8(4):163-169 (2001).

Poduslo et al., "Polyamine modification increases the permeability of proteins at the blood—nerve and blood-brain barriers," *J. Neurochem.*, 66:1599-1609 (1996).

Pons et al., "Energetic analysis of an antigen/antibody interface: alanine scanning mutagenesis and double mutant cycles on the HyHEL-10/lysozyme interaction," *Protein Sci.*, 8(5):958-68 (1999).

Portolano et al., "Lack of Promiscuity in Autoantigen-Specific H and L Chain Combinations as Revealed by Human H and L Chain "Roulette"," *J. Immunol.*, 150(3):880-887 (1993).

Presta, "Engineering of therapeutic antibodies to minimize immunogenicity and optimize function," *Adv. Drug Deliv. Rev.*, 58(5-6):640-56 (2006).

Price et al., "Tissue factor and tissue factor pathway inhibitor," *Anaesthesia*, 59:483-492 (2004).

Queen et al., "A humanized antibody that binds to the interleukin 2 receptor," *Proc. Natl. Acad. Sci. U.S.A.*, 86(24):10029-10033 (1989).

Raffen et al., "Reengineering immunoglobulin domain interactions by introduction of charged residues," *Protein Eng.*, 11:303-309 (1998).

Rajpal et al., "A general method for greatly improving the affinity of antibodies by using combinatorial libraries," *Proc. Natl. Acad. Sci. USA*, 102:8466-71 (2005).

Rathanaswami et al., "Demonstration of an in vivo generated sub-picomolar affinity fully human monoclonal antibody to interleukin-8," *Biochem. Biophys. Res. Commun.*, 334:1004-13 (2005).

Reddy et al., "Elimination of Fc receptor-dependent effector functions of a modified IgG4 monoclonal antibody to human CD4," *J. Immunol.*, 164(4):1925-33 (2000).

Reichert et al., "Development trends for monoclonal antibody cancer therapeutics," *Nat. Rev. Drug Discov.*, 6(5):349-56 (2007).

Reichert et al., "Monoclonal antibody successes in the clinic," *Nat. Biotechnol.*, 23:1073-78 (2005).

Ridgway et al., "'Knobs-into-holes' engineering of antibody $C_H3$ domains for heavy chain heterodimerization," *Protein Eng.*, 9:617-621 (1996).

Roitt et al., Immunology, M., Mir, (2000), pp. 110-111 (in Russian, with what is believed to be a published English equivalent of those pages taken from ROITT et al., "Antibody Structure and Function," Immunology, Fifth Ed., (1998), pp. 80-81).

Rothe et al., "Ribosome display for improved biotherapeutic molecules," *Expert Opin. Biol. Ther.*, 6:177-187 (2006).

Rudikoff et al., "Single amino acid substitution altering antigen-binding specificity," *Proc. Natl. Acad. Sci. USA*, 79:1979-1983 (1982).

Ruef et al., "A bispecific antifibrin-antiplatelet urokinase conjugate (BAAUC) induces enhanced clot lysis and inhibits platelet aggregation," *Thromb. Haemost.*, 82(1):109-114 (1999).

Ruf et al., "Pharmacokinetics and in vivo stability of intraperitoneally administered therapeutic antibody catumaxomab," *J. Clin. Oncol.*, 26 (May 20 suppl) (2008), abstr 14006.

Salfeld et al., "Isotype selection in antibody engineering," *Nat. Biotechnol.*, 25:1369-72 (2007).

Sal-Man et al., "Arginine mutations within a transmembrane domain of Tar, an *Escherichia coli* aspartate receptor, can drive homodimer dissociation and heterodimer association in vivo," *Biochem. J.*, 385:29-36 (2005).

Sato et al., "Properties of Two VEGF Receptors, Flt-1 and KDR, in Signal Transduction," *Ann N.Y. Acad. Sci*, 902:201-207, discussion 205-7 (May 2000).

Sato et al., "Reshaping a human antibody to inhibit the interleukin 6-dependent tumor cell growth," *Cancer Res.*, 53:851-856 (1993).

Schaeffer et al., "The Rat Glomerular Filtration Barrier Does Not Show Negative Charge Selectivity," *Microcirculation*, 9:329-342 (2002).

Schmidt et al., *Human Physiology*, Moscow, 2:431-436 (1996), and English translation: Schmidt et al., "Hemostatis and Coagulation," *Human Physiology*, R.F. Schmidt, G. Thews (Eds.), Second, Completely Revised Edition, 418-423 [translated by Marguerite A. Biederman-Thorson], Springer-Verlag (1989).

Schmidt et al., *Human Physiology*, Moscow, 3:764 (1996), and English translation: Schmidt et al., "Enzymes of the pancreatic juice," *Human Physiology*, R.F. Schmidt, G. Thews (Eds.), Second, Completely Revised Edition, 716 [translated by Marguerite A. Biederman-Thorson], Springer-Verlag (1989).

Schmitz et al., "Phage display: a molecular tool for the generation of antibodies—a review," *Placenta.*, 21 Suppl A:S106-12 (2000).

Segal et al., "Bispecific antibodies in cancer therapy," *Curr. Opin. Immunol.*, 11:558-562 (1999).

Segal et al., "Introduction: bispecific antibodies," *J. Immunol. Methods*, 248:1-6 (2001).

Shalaby et al., "Development of Humanized Bispecific Antibodies Reactive with Cytotoxic Lymphocytes and Tumor Cells Overexpressing the *HER2* Protooncogene," *J. Exp. Med.*, 175:217-225 (1992).

Shire et al., "Challenges in the development of high protein concentration formulations," *J. Pharm. Sci.*, 93:1390-1402 (2004).

Shaul, "Exploring the charge space of protein-protein association: a proteomic study," *Proteins*, 60:341-352 (2005).

Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.*, 276:6591-6604 (2001) (Epub Nov. 28, 2000).

Shima et al., "Factor VIII Taitei Kotai (2), Ketsuyubyo A Kanja Katsueki ni okeru in vitro Gyoko Kassei no Kento", Rinsho Ketsueki 46(8):777, 2005.

Sinha et al., "Electrostatics in protein binding and function," *Curr. Protein Pept. Sci.*, 3(6):601-14 (2002).

Sinha et al., "Molecular dynamics simulation of a high-affinity antibody-protein complex: the binding site is a mosaic of locally flexible and preorganized rigid regions," *Cell Biochem Biophys.*, 43:253-273 (2005).

Smans et al., "Bispecific antibody-mediated lysis of primary cultures of ovarian carcinoma cells using multiple target antigens," *Int. J. Cancer*, 83:270-277 (1999).

Smith, "Creative Expression: Mammalian Expression Vectors and Systems," *The Scientist Magazine*, Feb. 2, 1998, 3 pages.

Soeda et al., "Factor VIII Taitei Kotai (1) Ko FIXa/FX bispecific Kotai no Sakusei oyobi characterization", *Rinsho Ketsueki*, 46(8):728 (2005).

(56) References Cited

OTHER PUBLICATIONS

Soeda et al., "Phage library-ho ni yori Sakusei shita Ko-FIXa/Ko-FX bispecific Kotai no FVIII Taitei Sayo," *Japanese Journal of Thrombosis and Hemstasis*, 16(5):526 (2005).
Stickney et al., "Bifunctional Antibody: A Binary Radiopharmaceutical Delivery System for Imaging Colorectal Carcinoma," *Cancer Res.*, 51:6650-6655 (1991).
Strand et al., "Biologic therapies in rheumatology: lessons learned, future directions," *Nat. Rev. Drug Discov.*, 6:75-92 (2007).
Sun et al., "Coexpression of Gas6/Axl in human ovarian cancers," *Oncology*, 66(6):450-7 (2004).
Suresh et al., "Advantages of bispecific hybridomas in one-step immunocytochemistry and immunoassays," *Proc. Natl. Acad. Sci. USA*, 83:7989-7993 (1986).
Suresh et al., "Bispecific Monoclonal Antibodies from Hybrid Hybridomas," *Methods Enzymol.*, 121:210-228 (1986).
Taki, *The Journal of Japanese Society on Thrombosis and Hemostasis*, 13:109-113 (2002) (see reference AXX for concise English explanation).
Tan et al., "Engineering the isoelectric point of a renal cell carcinoma targeting antibody greatly enhances scFv solubility," *Immunotechnology*, 4(2):107-114 (1998).
Tarditi et al., "Selective high-performance liquid chromatographic purification of bispecific monoclonal antibodies," *J. Chromatogr.*, 599:13-20 (1992).
Teeling et al., "The biological activity of human CD20 monoclonal antibodies is linked to unique epitopes on CD20," *J. Immunol.*, 177(1):362-71 (2006).
Ten Kate et al., "Effect of isoelectric point on biodistribution and inflammation: imaging with indium-111-labelled IgG," *Eur. J. Nucl. Med.*, 17:305-309 (1990).
Tsuchiya, Credit Suisse Seminar, "Therapeutic Antibody," at Fuji-Gotemba Laboratories, p. 21 (2006) (with English Translation).
Tsurushita et al., "Design of humanized antibodies: From anti-Tac to Zenapax," *Methods*, 36:69-83 (2005).
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J. Mol. Biol.*, 320(2):415-28 (2002).
Van et al., "Immunogenicity screening in protein drug development," *Expert Opin. Biol. Ther.*, 7(3):405-18 (2007).
Van Loghem et al., "Staphylococcal protein A and human IgG subclasses and allotypes," *Scand. J. Immunol.*, 15(3):275-8 (1982).
Warnaar et al., "Purification of bispecific F(ab')2 from murine trinoma OC/TR with specificity for CD3 and ovarian cancer," *Hybridoma*, 13:519-526 (1994).
Weiner et al., "A Human Tumor Xenograft Model of Therapy with a Bispecific Monoclonal Antibody Targeting c-*erb*B-2 and CD16," *Cancer Res.*, 53:94-100 (1993).
Weiner et al., "The Role of T Cell Activation in Anti-CD3 × Antitumor Bispecific Antibody Therapy," *J. Immunol.*, 152:2385-2392 (1994).
Wiens et al., "Somatic mutation in VH complementarity-determining region 2 and framework region 2: differential effects on antigen binding and Ig secretion," *J. Immunol.*, 159(3):1293-302 (1997).
Wiens et al., "Mutation of a single conserved residue in VH complementarity-determining region 2 results in a severe Ig secretion defect," *J. Immunol.*, 167(4):2179-86 (2001).
Wu et al., "Development of motavizumab, an ultra-potent antibody for the prevention of respiratory syncytial virus infection in the upper and lower respiratory tract," *J. Mol. Biol.*, 368:652-65 (2007).
Xiang et al., "Study of B72.3 combining sites by molecular modeling and site-directed mutagenesis," *Protein Eng.*, 13(5):339-44 (2000).
Xiang et al., "Production of Murine V-Human Crl Chimeric Anti-TAG72 Antibody Using V Region cDNA Amplified by PCR," *Mol. Immunol.*, 27:809-817 (1990).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," *J. Pharmacol. Exp. Ther.*, 301:467-477 (2002).
Yang et al., "Tailoring structure-function and pharmacokinetic properties of single-chain Fv proteins by site-specific PEGylation," *Protein Eng.*, 16:761-770 (2003).
Zhu et al., "MHC class I-related neonatal Fc receptor for IgG is functionally expressed in monocytes, intestinal macrophages, and dendritic cells," *J. Immunol.*, 166(5):3266-76 (2001).
Zuckier et al., "Chimeric human-mouse IgG antibodies with shuffled constant region exons demonstrate that multiple domains contribute to in vivo half-life," *Cancer Res.*, 58:3905-08 (1998).
Zwick et al., "The long third complementarity-determining region of the heavy chain is important in the activity of the broadly neutralizing anti-human immunodeficiency virus type 1 antibody 2F5," *J. Virol.*, 78(6):3155-61 (2004).
USPTO Restriction Requirement in U.S. Appl. No. 10/575,193, mailed Mar. 24, 2009, 7 pages.
Fish & Richardson P.C., Response to Restriction Requirement dated Mar. 24, 2009 in U.S. Appl. No. 10/575,193, filed Jun. 23, 2009, 1 page.
USPTO Non-Final Office Action in U.S. Appl. No. 10/575,193, mailed Sep. 24, 2009, 38 pages.
Fish & Richardson P.C., Amendment in Reply to Action dated Sep. 24, 2009 in U.S. Appl. No. 10/575,193, filed Mar. 24, 2010, 19 pages.
USPTO Final Office Action in U.S. Appl. No. 10/575,193, mailed Jun. 23, 2010, 18 pages.
Fish & Richardson P.C., Amendment in Reply to Action dated Jun. 23, 2010 in U.S. Appl. No. 10/575,193, filed Dec. 22, 2010, 13 pages.
USPTO Notice of Allowance in U.S. Appl. No. 10/575,193, mailed Mar. 18, 2011, 11 pages.
Fish & Richardson P.C., Amendment in U.S. Appl. No. 10/575,193, filed Jun. 17, 2011, 15 pages.
USPTO Notice of Allowance in U.S. Appl. No. 10/575,193, mailed Jul. 13, 2011, 8 pages.
International Search Report for App. Ser. No. PCT/JP2004/014911, mailed Jan. 25, 2005, 3 pages.
International Preliminary Report on Patentability for App. Ser. No. PCT/JP2004/014911, dated Sep. 27, 2005, 12 pages.
European Search Report for App. Ser. No. EP 04 79 2180, dated Jan. 17, 2008, 3 pages.
International Search Report for App. Ser. No. PCT/JP2003/013123, mailed Nov. 25, 2003, 4 pages.
International Preliminary Report on Patentability for App. Ser. No. PCT/JP2003/013123, dated Oct. 20, 2005, 7 pages.
European Search Report for App. Ser. No. EP 03 75 1478, dated Jan. 11, 2008, 3 pages.
USPTO Restriction Requirement in U.S. Appl. No. 10/575,905, mailed Jun. 25, 2009, 10 pages.
Fish & Richardson P.C., Amendment and Response to Restriction Requirement dated Jun. 25, 2009 in U.S. Appl. No. 10/575,905, filed Sep. 25, 2009, 14 pages.
USPTO Restriction Requirement in U.S. Appl. No. 10/575,905, mailed Nov. 18, 2009, 14 pages.
Fish & Richardson P.C., Amendment and Response to Restriction Requirement dated Nov. 18, 2009 in U.S. Appl. No. 10/575,905, filed Apr. 16, 2010, 12 pages.
USPTO Non-Final Office Action in U.S. Appl. No. 10/575,905, mailed Jun. 23, 2010, 10 pages.
Fish & Richardson P.C., Amendment in Reply to Action dated Jun. 23, 2010 in U.S. Appl. No. 10/575,905, filed Dec. 22, 2010, 10 pages.
USPTO Final Office Action in U.S. Appl. No. 10/575,905, mailed Feb. 24, 2011, 7 pages.
USPTO Restriction Requirement in U.S. Appl. No. 11/910,836, dated Mar. 18, 2011, 7 pages.
Fish & Richardson P.C., Response to Restriction Requirement dated Mar. 18, 2011 in U.S. Appl. No. 11/910,836, filed Sep. 6, 2011, 1 page.
USPTO Non-Final Office Action in U.S. Appl. No. 11/910,836, dated Sep. 30, 2011, 21 pages.
International Preliminary Report on Patentability for App. Ser. No. JP2006/306821, dated Oct. 9, 2007, 7 pages.

(56) References Cited

OTHER PUBLICATIONS

International Search Report for App. Ser. No. JP2006/306821, mailed Jul. 11, 2006, 6 pages.
European Search Report for App. Ser. No. 06 73 0769, dated Jun. 18, 2009 (8 pages).
USPTO Restriction Requirement in U.S. Appl. No. 13/434,643, dated Jul. 27, 2012, 6 pages.
Fish & Richardson P.C., Response to Restriction Requirement dated Jul. 27, 2012 and Preliminary Amendment in U.S. Appl. No. 13/434,643, filed on Jan. 24, 2013, 10 pages.
USPTO Non-Final Office Action in U.S. Appl. No. 13/434,643, dated Feb. 12, 2013, 17 pages.
Fish & Richardson P.C., Amendment in Reply to Office Action dated Feb. 12, 2013 in U.S. Appl. No. 13/434,643, filed on May 13, 2013, 18 pages.
USPTO Final Office Action in U.S. Appl. No. 13/434,643, dated Jul. 11, 2013, 19 pages.
International Preliminary Report on Patentability for App. Ser. No. PCT/JP2011/076486, dated Jun. 12, 2013, 9 pages.
International Search Report for App. Ser. No. PCT/JP2009/057309, mailed Jul. 7, 2009, 8 pages.
International Preliminary Report on Patentability for App. Ser. No. PCT/JP2009/057309, mailed Nov. 30, 2010, 7 pages.
European Search Report for App. Ser. No. EP 09 72 9337, dated Nov. 3, 2011, 3 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed on Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed on Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed on Sep. 11, 2012, 12 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Preliminary Report on Patentability for App. Ser. No. PCT/JP2007/057058, dated Oct. 21, 2008, 11 pages.
International Search Report App. Ser. No. PCT/JP2007/057058, mailed May 7, 2001, 2 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
USPTO Non-Final Office Action in U.S. Appl. No. 12/295,075, dated Jun. 7, 2013, 17 pages.
USPTO Restriction Requirement in U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.
USPTO Non-Final Office Action in U.S. Appl. No. 11/910,128, dated Apr. 25, 2012, 21 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
USPTO Final Office Action in U.S. Appl. No. 11/910,128, dated Sep. 10, 2013, 12 pages.
Fish & Richardson P.C., Amendment in Reply to Final Office Action dated Jun. 3, 2010 in U.S. Appl. No. 10/560,098, filed Jul. 5, 2011, 17 pages.
USPTO Non-Final Office Action in U.S. Appl. No. 10/560,098, mailed Dec. 8, 2011, 11 pages.
Fish & Richardson P.C., Amendment in Reply to Non-Final Office Action dated Dec. 8, 2011 in U.S. Appl. No. 10/560,098, filed Jun. 5, 2012, 11 pages.
USPTO Final Office Action in U.S. Appl. No. 10/560,098, dated Aug. 15, 2012, 10 pages.
Fish & Richardson P.C., Amendment in Reply to Final Office Action dated Aug. 15, 2012 in U.S. Appl. No. 10/560,098, filed Sep. 5, 2012, 8 pages.
USPTO Interview Summary in U.S. Appl. No. 10/560,098, dated Sep. 7, 2012, 3 pages.
USPTO Notice of Allowance in U.S. Appl. No. 10/560,098, dated Apr. 25, 2013, 12 pages.
USPTO Notice of Allowance in U.S. Appl. No. 10/560,098, dated Jul. 9, 2013, 6 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed on Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed on Jul. 25, 2012, 1 page.
USPTO Non-Final Office Action in U.S. Appl. No. 12/936,587, dated Nov. 7, 2012, 13 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed on Nov. 1, 2012, 2 pages.
USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed on Jul. 2, 2013, 18 pages.
USPTO Final Office Action in U.S. Appl. No. 12/679,922, dated Aug. 2, 2013, 12 pages.
International Preliminary Report on Patentability for App. Ser. No. PCT/JP2010/073361, dated Aug. 14, 2012, 7 pages.
USPTO Non-Final Office Action in U.S. Appl. No. 13/595,139, dated Nov. 14, 2012, 10 pages.
Figini et al., "In vitro assembly of repertoires of antibody chains on the surface of phage by renaturation,". *J. Mol Biol.*, May 27, 1994;239(1):68-78.
Vaughan et al., "Human antibodies with sub-nanomolar affinities isolated from a large non-immunized phage display library," *Nat Biotechnol.*, Mar. 1996;14(3):309-14.

* cited by examiner

SEQUENCE LISTING

<160> NUMBER OF SEQ ID NOS: 179

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Ser Thr Tyr Tyr Arg His Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Leu Gly Ala Gly Trp Tyr Phe Asp Phe
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Met Thr Lys Asn Gln Val Ser Leu
            355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

<210> SEQ ID NO 2
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
            35                  40                  45

Ala Ser Ile Ser Pro Ser Gly Gly Ser Thr Tyr Tyr Arg Arg Ser Val
50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Arg Ala Gly His Asn Leu Gly Ala Gly Trp Tyr Phe Asp Phe
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

```
Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

<210> SEQ ID NO 3
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Phe Gly Ala Gly Trp Tyr Phe Asp Phe
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
            180                 185                 190
Thr Val Pro Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Ser Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Lys Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445

<210> SEQ ID NO 4
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Asn
            20                  25                  30
Asn Met Asp Trp Val Arg Gln Ala Pro Gly Gln Gly Leu Glu Trp Met
        35                  40                  45
Gly Asp Ile Asn Thr Arg Ser Gly Gly Ser Ile Tyr Asn Glu Glu Phe
    50                  55                  60
Gln Asp Arg Val Ile Met Thr Val Asp Lys Ser Thr Gly Thr Ala Tyr
65                  70                  75                  80
Met Glu Leu Ser Ser Leu Arg Ser Glu Asp Thr Ala Val Tyr His Cys
                85                  90                  95
```

```
Ala Arg Arg Lys Ser Arg Gly Tyr His Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 5
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ser Glu Leu Lys Lys Pro Gly Ala
1               5                   10                  15
```

-continued

```
Ser Val Lys Val Ser Cys Lys Ala Ser Gly Tyr Thr Phe Thr Asp Asn
            20                  25                  30
Asn Met His Trp Val Arg Gln Ala Pro Gly Gln Gly Leu Glu Trp Met
        35                  40                  45
Gly Asp Ile Asn Thr Arg Ser Gly Ser Ile Tyr Asn Glu Glu Phe
 50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Val Tyr His Cys
                85                  90                  95
Ala Arg Arg Lys Ser Tyr Gly Tyr His Leu Asp Glu Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Cys Glu Met Thr Lys Asn Gln Val Ser Leu Ser Cys Ala Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Val Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
```

```
Asn His Tyr Thr Gln Lys Ser Leu Ser Leu Ser Leu
            435                 440
```

<210> SEQ ID NO 6
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Val Tyr His Cys
                85                  90                  95

Ala Arg Arg Lys Ser Tyr Gly Asn His Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350
```

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn Arg Tyr Thr Gln Ser Leu Ser Leu Ser Pro
        435                 440

<210> SEQ ID NO 7
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Lys Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Gln Ser Tyr Gly Tyr His Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val

```
                    260                 265                 270
Gln Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn Arg Tyr Thr Gln Glu Ser Leu Ser Leu Ser Pro
        435                 440

<210> SEQ ID NO 8
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Tyr Lys Asn
            20                  25                  30

Leu Ala Trp Tyr Gln Gln Lys Pro Gly Gln Ala Pro Lys Leu Leu Ile
        35                  40                  45

Tyr Ser Ala Ser Tyr Arg Tyr Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Tyr Ser Gly Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

```
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
        210
```

<210> SEQ ID NO 9
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Gln Met Thr Gln Ser Pro Ser Ser Leu Ser Ala Ser Val Gly
 1               5                  10                  15
Asp Arg Val Thr Ile Thr Cys Lys Ala Ser Gln Asn Ile Tyr Lys Asn
             20                  25                  30
Leu Ala Trp Tyr Gln Gln Lys Pro Gly Gln Ala Pro Lys Leu Leu Ile
         35                  40                  45
Tyr Ser Ala Ser Tyr Arg Tyr Ser Gly Val Pro Asp Arg Phe Ser Gly
 50                  55                  60
Ser Arg Tyr Gly Thr Asp Phe Thr Leu Thr Ile Ser Ser Leu Gln Pro
 65                  70                  75                  80
Glu Asp Leu Ala Thr Tyr Tyr Cys Gln Gln Tyr Tyr Ser Pro Pro Leu
                 85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 10
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Tyr Tyr
             20                  25                  30
```

-continued

```
Asp Met Ala Trp Val Arg Gln Ala Pro Gly Lys Gly Leu Glu Trp Val
         35                  40                  45
Ala Ser Ile Ser Pro Ser Gly Ser Thr Tyr Tyr Arg Arg Ser Val
 50                  55                  60
Lys Gly Arg Phe Thr Val Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Arg Ala Gly His Asn Phe Gly Ala Gly Trp Tyr Phe Asp Phe
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Lys Thr Tyr Thr Cys Asn Val
        195                 200                 205
Asp His Lys Pro Ser Asn Thr Lys Val Asp Lys Arg Val Glu Ser Lys
    210                 215                 220
Tyr Gly Pro Pro Cys Pro Pro Cys Pro Ala Pro Glu Phe Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser Gln Glu
            260                 265                 270
Asp Pro Glu Val Gln Phe Asn Trp Tyr Val Asp Gly Val Glu Val His
        275                 280                 285
Asn Ala Lys Thr Lys Pro Arg Glu Glu Gln Phe Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Lys Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
        435                 440                 445
```

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Tyr Gly Ala Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365
```

```
Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
                435                 440                 445

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Asn Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Arg Ala Gly His Asn Tyr Gly Ala Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285
```

Asn Ala Lys Thr Lys Pro Arg Glu Glu Gln Phe Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

<210> SEQ ID NO 13
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Asn Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly His Asn Tyr Gly Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val

```
            195                 200                 205
Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Lys Glu Met Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

<210> SEQ ID NO 14
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
                20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly His Asn Tyr Gly Gly Trp Tyr Phe Asp Tyr
                100                 105                 110
```

```
Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

<210> SEQ ID NO 15
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30
```

-continued

Asp Ile Gln Trp Val Arg Gln Ala Pro Gly Lys Gly Leu Glu Trp Val
         35                  40                  45

Ser Ser Ile Ser Pro Ser Gly Gln Ser Thr Tyr Tyr Arg Arg Glu Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Arg Ser Gly His Asn Tyr Gly Gly Trp Tyr Phe Asp Tyr
             100                 105                 110

Trp Gly Gln Gly Thr Leu Val Thr Val Ser Ser Ala Ser Thr Lys Gly
             115                 120                 125

Pro Ser Val Phe Pro Leu Ala Pro Cys Ser Arg Ser Thr Ser Glu Ser
         130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Thr Cys Asn Val
         195                 200                 205

Asp His Lys Pro Ser Asn Thr Lys Val Asp Lys Arg Val Glu Ser Lys
     210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Gln Lys Glu Met Thr Lys Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Glu Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

<210> SEQ ID NO 16
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Ser Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly His Asn Phe Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Glu Met Thr Lys Asn Gln Val Ser Leu
        355                 360                 365
```

```
Trp Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

<210> SEQ ID NO 17
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly Lys Ser Tyr Gly Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
```

```
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Gln Lys Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Glu Gly Asn Val Phe Ser Cys Ser Val Met His
            420                 425                 430
Glu Ala Leu His Asn His Tyr Thr Gln Lys Ser Leu Ser Leu Ser Leu
            435                 440                 445
```

<210> SEQ ID NO 18
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Tyr Tyr
            20                  25                  30
Asp Ile Gln Trp Val Arg Gln Ala Pro Gly Lys Gly Leu Glu Trp Val
        35                  40                  45
Ser Ser Ile Ser Pro Ser Gly Gln Ser Thr Tyr Tyr Arg Arg Glu Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Ser Gly Arg Glu Tyr Gly Gly Gly Trp Tyr Phe Asp Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Cys Ser Arg Ser Thr Ser Glu Ser
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
```

```
Thr Val Pro Ser Ser Ser Leu Gly Thr Gln Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser Gln Glu
            260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
            420                 425                 430

Glu Ala Leu His Asn Arg Tyr Thr Gln Lys Ser Leu Ser Leu Ser Pro
        435                 440                 445

<210> SEQ ID NO 19
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110
```

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 20
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr

-continued

```
                 20                  25                  30
Asp Ile Gln Trp Val Arg Gln Ala Pro Gly Lys Gly Leu Glu Trp Val
             35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Gly Arg Glu Tyr Gly Gly Gly Trp Tyr Phe Asp Tyr
             100                 105                 110

Trp Gly Gln Gly Thr Leu Val Thr Val Ser Ser Ala Ser Thr Lys Gly
             115                 120                 125

Pro Ser Val Phe Pro Leu Ala Pro Cys Ser Arg Ser Thr Ser Glu Ser
             130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Thr Cys Asn Val
             195                 200                 205

Asp His Lys Pro Ser Asn Thr Lys Val Asp Lys Arg Val Glu Ser Lys
         210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Gln Lys Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Glu Gly Asn Val Phe Ser Cys Ser Val Met His
             420                 425                 430

Glu Ala Leu His Asn Arg Tyr Thr Gln Lys Ser Leu Ser Leu Ser Pro
         435                 440                 445
```

<210> SEQ ID NO 21
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Lys Ser Tyr Gly Tyr His Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Ser Cys Ala Val
```

```
                 355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
            435                 440

<210> SEQ ID NO 22
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Gly Thr Ala Tyr
65                  70                  75                  80

Met Glu Leu Ser Ser Leu Arg Ser Glu Asp Thr Ala Val Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Met His Glu Ala Leu His
            420                 425                 430

Asn Arg Tyr Thr Gln Glu Ser Leu Ser Leu Ser Pro
            435                 440

<210> SEQ ID NO 23
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Val Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
            210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Met His Glu Ala Leu His
            420                 425                 430

Asn Arg Tyr Thr Gln Glu Ser Leu Ser Leu Ser Pro
            435                 440

<210> SEQ ID NO 24
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
        50                  55                  60

Gln Asp Arg Val Ile Met Thr Val Asp Lys Ser Thr Thr Ala Tyr
65                  70                  75                  80

Met Glu Leu Ser Ser Leu Arg Ser Glu Asp Thr Ala Thr Tyr His Cys
            85                  90                  95

Ala Arg Arg Lys Ser Tyr Gly Tyr Tyr Leu Asp Glu Trp Gly Glu Gly

```
            100                 105                 110
Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn Arg Tyr Thr Gln Glu Ser Leu Ser Leu Ser Pro
            435                 440

<210> SEQ ID NO 25
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
 50                  55                  60

Gln Asp Arg Val Ile Met Thr Val Asp Lys Ser Thr Asp Thr Ala Tyr
 65                  70                  75                  80

Met Glu Leu Ser Ser Leu Arg Ser Glu Asp Thr Ala Thr Tyr His Cys
            85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Thr Cys Asn Val Asp His Lys Pro
            195                 200                 205

Ser Asn Thr Lys Val Asp Lys Arg Val Glu Ser Lys Tyr Gly Pro Pro
 210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
 290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
```

435              440

<210> SEQ ID NO 26
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Thr Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr His Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
            435                 440
```

<210> SEQ ID NO 27
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr His Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn Arg Tyr Thr Gln Glu Ser Leu Ser Leu Ser Pro
                435                 440

<210> SEQ ID NO 28
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Lys Asn Ile Glu Arg Asn
            20                  25                  30

Leu Ala Trp Tyr Gln Gln Lys Pro Gly Gln Ala Pro Arg Leu Leu Ile
        35                  40                  45

Tyr Arg Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                        180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 29
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Arg Ala Asp Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
```

```
            35                  40                  45
Tyr Gln Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
 65                  70                  75                  80

Glu Asp Ile Ala Thr Tyr Tyr Cys Gln Gln Tyr Ser Ser Pro Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 31
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
 1               5                  10                  15

Asp Arg Val Thr Ile Thr Cys Lys Ala Ser Arg Asn Ile Glu Arg Gln
                 20                  25                  30

Leu Ala Trp Tyr Gln Gln Lys Pro Gly Gln Ala Pro Glu Leu Leu Ile
            35                  40                  45

Tyr Gln Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
 65                  70                  75                  80

Glu Asp Ile Ala Thr Tyr Tyr Cys Gln Gln Tyr Ser Ser Pro Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30
```

```
Leu Ala Trp Tyr Gln Gln Lys Pro Gly Gln Ala Pro Glu Leu Leu Ile
        35                  40                  45

Tyr Arg Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Arg Ala Asp Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Gly Ser Thr Tyr Tyr Arg His Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Leu Gly Ala Gly Trp Tyr Phe Asp Phe
            100                 105                 110

Trp Gly Gln Gly Thr Leu Val Thr Val Ser Ser
            115                 120

<210> SEQ ID NO 36
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Leu Gly Ala Gly Trp Tyr Phe Asp Phe
            100                 105                 110

Trp Gly Gln Gly Thr Leu Val Thr Val Ser Ser
            115                 120

<210> SEQ ID NO 37
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Phe Gly Ala Gly Trp Tyr Phe Asp Phe
            100                 105                 110

Trp Gly Gln Gly Thr Leu Val Thr Val Ser Ser
        115                 120
```

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 38

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met Ala Trp Val Arg Gln Ala Pro Gly Lys Gly Leu Glu Trp Val
        35                  40                  45

Ala Ser Ile Ser Pro Ser Gly Gly Ser Thr Tyr Tyr Arg Arg Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Ala Gly His Asn Tyr Gly Ala Gly Trp Tyr Phe Asp Tyr
            100                 105                 110

Trp Gly Gln Gly Thr Leu Val Thr Val Ser Ser
        115                 120
```

<210> SEQ ID NO 39
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Asn Trp Val Arg Gln Ala Pro Gly Lys Gly Leu Glu Trp Val
        35                  40                  45

Ala Ser Ile Ser Pro Ser Gly Ser Thr Tyr Tyr Arg Arg Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Arg Ala Gly His Asn Tyr Gly Ala Gly Trp Tyr Phe Asp Tyr
            100                 105                 110

Trp Gly Gln Gly Thr Leu Val Thr Val Ser Ser
            115                 120

<210> SEQ ID NO 40
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Asn Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly His Asn Tyr Gly Gly Gly Trp Tyr Phe Asp Tyr
            100                 105                 110

Trp Gly Gln Gly Thr Leu Val Thr Val Ser Ser
            115                 120

<210> SEQ ID NO 41
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

```
Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Ser Gly His Asn Tyr Gly Gly Trp Tyr Phe Asp Tyr
            100                 105                 110

Trp Gly Gln Gly Thr Leu Val Thr Val Ser Ser
            115                 120
```

<210> SEQ ID NO 42
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
            20                  25                  30

Asp Ile Ser Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Ser Gly His Asn Phe Gly Gly Trp Tyr Phe Asp Tyr
            100                 105                 110

Trp Gly Gln Gly Thr Leu Val Thr Val Ser Ser
            115                 120
```

<210> SEQ ID NO 43
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Arg Ser Gly Lys Ser Tyr Gly Gly Trp Tyr Phe Asp Tyr
            100                 105                 110

Trp Gly Gln Gly Thr Leu Val Thr Val Ser Ser
        115                 120
```

```
<210> SEQ ID NO 44
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Ser Gly Arg Glu Tyr Gly Gly Trp Tyr Phe Asp Tyr
            100                 105                 110

Trp Gly Gln Gly Thr Leu Val Thr Val Ser Ser
        115                 120
```

```
<210> SEQ ID NO 45
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser
        115                 120
```

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Lys Ser Tyr Gly Tyr His Leu Asp Glu Trp Gly Glu Gly
            100                 105                 110

Thr Leu Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Gly Thr Ala Tyr
65                  70                  75                  80

Met Glu Leu Ser Ser Leu Arg Ser Glu Asp Thr Ala Val Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Gly Thr Ala Tyr
65                  70                  75                  80

Met Glu Leu Ser Ser Leu Arg Ser Glu Asp Thr Ala Val Tyr His Cys
                85                  90                  95

Ala Arg Arg Lys Ser Arg Gly Tyr His Leu Asp Glu Trp Gly Glu Gly
            100                 105                 110

Thr Leu Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Val Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met His Trp Val Arg Gln Ala Pro Gly Gln Gly Leu Glu Trp Met

```
                35                  40                  45
Gly Asp Ile Asn Thr Arg Ser Gly Gly Ser Ile Tyr Asn Glu Glu Phe
        50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Val Tyr His Cys
                85                  90                  95
Ala Arg Arg Lys Ser Tyr Gly Tyr His Leu Asp Glu Trp Gly Glu Gly
                100                 105                 110
Thr Leu Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Asn
                20                  25                  30
Asn Met Asp Trp Val Arg Gln Ala Pro Gly Gln Gly Leu Glu Trp Met
            35                  40                  45
Gly Asp Ile Asn Thr Arg Ser Gly Gly Ser Ile Tyr Asn Glu Glu Phe
        50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Val Tyr His Cys
                85                  90                  95
Ala Arg Arg Lys Ser Tyr Gly Asn His Leu Asp Glu Trp Gly Glu Gly
                100                 105                 110
Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Asn
                20                  25                  30
Asn Met Asp Trp Val Arg Gln Ala Pro Gly Gln Gly Leu Glu Trp Met
            35                  40                  45
Gly Asp Ile Asn Thr Arg Ser Gly Gly Ser Ile Tyr Asn Glu Glu Phe
        50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Thr Tyr His Cys
```

```
                    85                  90                  95
Ala Arg Arg Lys Ser Tyr Gly Tyr Tyr Leu Asp Glu Trp Gly Glu Gly
                100                 105                 110
Thr Leu Val Thr Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
        50                  55                  60

Gln Asp Arg Val Ile Met Thr Val Asp Thr Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr His Leu Asp Glu Trp Gly Glu Gly
                100                 105                 110

Thr Leu Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Lys Ser Gly Gly Ser Ile Tyr Asn Glu Glu Phe
        50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Gln Ser Tyr Gly Tyr His Leu Asp Glu Trp Gly Glu Gly
                100                 105                 110

Thr Leu Val Thr Val Ser Ser
        115
```

```
<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr His Leu Asp Glu Trp Gly Glu Gly
            100                 105                 110

Thr Leu Val Thr Val Ser Ser
        115

<210> SEQ ID NO 56
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Tyr Lys Asn
            20                  25                  30

Leu Ala Trp Tyr Gln Gln Lys Pro Gly Gln Ala Pro Lys Leu Leu Ile
        35                  40                  45

Tyr Ser Ala Ser Tyr Arg Tyr Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Tyr Ser Gly Leu Thr
                85                  90                  95

Phe Gly Gly Gly Thr Lys Val Glu Ile Lys
            100                 105

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asn Ile Tyr Lys Asn
            20                  25                  30

Leu Ala Trp Tyr Gln Gln Lys Pro Gly Gln Ala Pro Lys Leu Leu Ile
        35                  40                  45

Tyr Ser Ala Ser Tyr Arg Tyr Ser Gly Val Pro Asp Arg Phe Ser Gly
 50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Tyr Ser Pro Pro Leu
                85                  90                  95

Thr Phe Gly Gly Gly Thr Lys Val Glu Ile Lys
            100                 105

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Lys Asn Ile Glu Arg Asn
            20                  25                  30

Leu Ala Trp Tyr Gln Gln Lys Pro Gly Gln Ala Pro Arg Leu Leu Ile
        35                  40                  45

Tyr Arg Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Arg Ala Asp Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95
```

Thr Phe Gly Gly Gly Thr Lys Val Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Arg Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys
            100                 105

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Arg Ala Asp Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80
```

```
Glu Asp Ile Ala Thr Tyr Tyr Cys Gln Gln Tyr Ser Asp Pro Pro Leu
                85                  90                  95
Thr Phe Gly Gly Gly Thr Lys Val Glu Ile Lys
            100                 105
```

<210> SEQ ID NO 65
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Cys Thr Leu Pro Pro Ser Gln Glu Glu Met Thr Lys
225                 230                 235                 240
Asn Gln Val Ser Leu Trp Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu
                325
```

<210> SEQ ID NO 66
<211> LENGTH: 325
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
                325
```

<210> SEQ ID NO 67
<211> LENGTH: 325
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 67

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu
                325
```

<210> SEQ ID NO 68
<211> LENGTH: 325
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
| | 50 | | | | | 55 | | | | | 60 | | | | |

| Leu | Ser | Ser | Val | Val | Thr | Val | Pro | Ser | Ser | Leu | Gly | Thr | Gln | Thr |
| 65 | | | | | 70 | | | | | 75 | | | | | 80 |

| Tyr | Thr | Cys | Asn | Val | Asp | His | Lys | Pro | Ser | Asn | Thr | Lys | Val | Asp | Lys |
| | | | | 85 | | | | | 90 | | | | | 95 | |

| Arg | Val | Glu | Ser | Lys | Tyr | Gly | Pro | Pro | Cys | Pro | Pro | Cys | Pro | Ala | Pro |
| | | | 100 | | | | | 105 | | | | | 110 | | |

| Glu | Phe | Leu | Gly | Gly | Pro | Ser | Val | Phe | Leu | Phe | Pro | Pro | Lys | Pro | Lys |
| | | | 115 | | | | | 120 | | | | | 125 | | |

| Asp | Thr | Leu | Met | Ile | Ser | Arg | Thr | Pro | Glu | Val | Thr | Cys | Val | Val | Val |
| 130 | | | | | 135 | | | | | 140 | | | | | |

| Asp | Val | Ser | Gln | Glu | Asp | Pro | Glu | Val | Gln | Phe | Asn | Trp | Tyr | Val | Asp |
| 145 | | | | | 150 | | | | | 155 | | | | | 160 |

| Gly | Val | Glu | Val | His | Asn | Ala | Lys | Thr | Lys | Pro | Arg | Glu | Glu | Gln | Tyr |
| | | | | 165 | | | | | 170 | | | | | 175 | |

| Asn | Ser | Thr | Tyr | Arg | Val | Val | Ser | Val | Leu | Thr | Val | Leu | His | Gln | Asp |
| | | | 180 | | | | | 185 | | | | | 190 | | |

| Trp | Leu | Asn | Gly | Lys | Glu | Tyr | Lys | Cys | Lys | Val | Ser | Asn | Lys | Gly | Leu |
| | | | 195 | | | | | 200 | | | | | 205 | | |

| Pro | Ser | Ser | Ile | Glu | Lys | Thr | Ile | Ser | Lys | Ala | Lys | Gly | Gln | Pro | Arg |
| | 210 | | | | | 215 | | | | | 220 | | | | |

| Glu | Pro | Gln | Val | Tyr | Thr | Leu | Pro | Pro | Ser | Gln | Lys | Glu | Met | Thr | Lys |
| 225 | | | | | 230 | | | | | 235 | | | | | 240 |

| Asn | Gln | Val | Ser | Leu | Thr | Cys | Leu | Val | Lys | Gly | Phe | Tyr | Pro | Ser | Asp |
| | | | | 245 | | | | | 250 | | | | | 255 | |

| Ile | Ala | Val | Glu | Trp | Glu | Ser | Asn | Gly | Gln | Pro | Glu | Asn | Asn | Tyr | Lys |
| | | | 260 | | | | | 265 | | | | | 270 | | |

| Thr | Thr | Pro | Pro | Val | Leu | Asp | Ser | Asp | Gly | Ser | Phe | Phe | Leu | Tyr | Ser |
| | | 275 | | | | | 280 | | | | | 285 | | | |

| Lys | Leu | Thr | Val | Asp | Lys | Ser | Arg | Trp | Gln | Glu | Gly | Asn | Val | Phe | Ser |
| | 290 | | | | | 295 | | | | | 300 | | | | |

| Cys | Ser | Val | Met | His | Glu | Ala | Leu | His | Asn | His | Tyr | Thr | Gln | Lys | Ser |
| 305 | | | | | 310 | | | | | 315 | | | | | 320 |

| Leu | Ser | Leu | Ser | Leu |
| | | | | 325 |

<210> SEQ ID NO 69
<211> LENGTH: 325
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 69

| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 70
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Lys Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn Arg Tyr Thr Gln Lys Ser
305                 310                 315                 320

Leu Ser Leu Ser Pro
                325

<210> SEQ ID NO 71
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
```

```
                65                  70                  75                  80
Tyr Thr Cys Asn Val Asp His Lys Pro Ser Asn Thr Lys Val Asp Lys
                    85                  90                  95

Arg Val Glu Ser Lys Tyr Gly Pro Pro Cys Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Cys Glu Met Thr Lys
225                 230                 235                 240

Asn Gln Val Ser Leu Ser Cys Ala Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Val Ser
            275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
                325

<210> SEQ ID NO 72
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95
```

```
Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Met His Glu Ala Leu His Asn Arg Tyr Thr Gln Glu Ser
305                 310                 315                 320

Leu Ser Leu Ser Pro
                325

<210> SEQ ID NO 73
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Glu Ser
305                 310                 315                 320

Leu Ser Leu Ser Pro
                325

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                           peptide

<400> SEQUENCE: 75

Tyr Tyr Asp Met Ala
1               5

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Ile Ser Pro Ser Gly Gly Ser Thr Tyr Tyr Arg His Ser Val Lys
1               5                   10                  15
Gly

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ala Gly His Asn Leu Gly Ala Gly Trp Tyr Phe Asp Phe
1               5                   10

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Tyr Asp Met Ala
1               5

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Ile Ser Pro Ser Gly Gly Ser Thr Tyr Tyr Arg Arg Ser Val Lys
1               5                   10                  15
Gly

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ala Gly His Asn Leu Gly Ala Gly Trp Tyr Phe Asp Phe
```

-continued

```
<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Tyr Asp Met Ala
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Ile Ser Pro Ser Gly Gly Ser Thr Tyr Tyr Arg Arg Ser Val Lys
1               5                   10                  15

Gly

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ala Gly His Asn Phe Gly Ala Gly Trp Tyr Phe Asp Phe
1               5                   10

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Tyr Asp Met Ala
1               5

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Ile Ser Pro Ser Gly Gly Ser Thr Tyr Tyr Arg Arg Ser Val Lys
1               5                   10                  15

Gly

<210> SEQ ID NO 86
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Gly His Asn Tyr Gly Ala Gly Trp Tyr Phe Asp Tyr
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Tyr Asp Ile Asn
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ile Ser Pro Ser Gly Gly Ser Thr Tyr Tyr Arg Arg Ser Val Lys
1               5                   10                  15

Gly

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ala Gly His Asn Tyr Gly Ala Gly Trp Tyr Phe Asp Tyr
1               5                   10

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Tyr Tyr Asp Ile Asn
1               5

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

```
Ser Ile Ser Pro Ser Gly Gln Ser Thr Tyr Tyr Arg Arg Glu Val Lys
1               5                   10                  15

Gly

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Ser Gly His Asn Tyr Gly Gly Gly Trp Tyr Phe Asp Tyr
1               5                   10

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Tyr Asp Ile Gln
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Ile Ser Pro Ser Gly Gln Ser Thr Tyr Tyr Arg Arg Glu Val Lys
1               5                   10                  15

Gly

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ser Gly His Asn Tyr Gly Gly Gly Trp Tyr Phe Asp Tyr
1               5                   10

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Tyr Asp Ile Ser
1               5
```

```
<210> SEQ ID NO 97
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Ile Ser Pro Ser Gly Gln Ser Thr Tyr Tyr Arg Arg Glu Val Lys
1               5                   10                  15

Gly

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ser Gly His Asn Phe Gly Gly Gly Trp Tyr Phe Asp Tyr
1               5                   10

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Tyr Asp Ile Gln
1               5

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Ile Ser Pro Ser Gly Gln Ser Thr Tyr Tyr Arg Arg Glu Val Lys
1               5                   10                  15

Gly

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ser Gly Lys Ser Tyr Gly Gly Gly Trp Tyr Phe Asp Tyr
1               5                   10

<210> SEQ ID NO 102
<211> LENGTH: 5
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 102

Tyr Tyr Asp Ile Gln
1               5

<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Ser Ile Ser Pro Ser Gly Gln Ser Thr Tyr Tyr Arg Arg Glu Val Lys
1               5                   10                  15

Gly

<210> SEQ ID NO 104
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Arg Ser Gly Arg Glu Tyr Gly Gly Gly Trp Tyr Phe Asp Tyr
1               5                   10

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Tyr Tyr Asp Ile Gln
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Ser Ile Ser Pro Ser Gly Gln Ser Thr Tyr Tyr Arg Arg Glu Val Lys
1               5                   10                  15

Gly

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

-continued

Arg Thr Gly Arg Glu Tyr Gly Gly Gly Trp Tyr Phe Asp Tyr
1               5                   10

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Asn Asn Met Asp
1               5

<210> SEQ ID NO 109
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Ile Asn Thr Arg Ser Gly Gly Ser Ile Tyr Asn Glu Glu Phe Gln
1               5                   10                  15
Asp

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Lys Ser Tyr Gly Tyr His Leu Asp Glu
1               5                   10

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Asn Asn Met Asp
1               5

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Ile Asn Thr Arg Ser Gly Gly Ser Ile Tyr Asn Glu Glu Phe Gln
1               5                   10                  15
Asp

<210> SEQ ID NO 113

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Lys Ser Tyr Gly Tyr Tyr Leu Asp Glu
1               5                   10

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Asn Asn Met Asp
1               5

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Asp Ile Asn Thr Arg Ser Gly Gly Ser Ile Tyr Asn Glu Glu Phe Gln
1               5                   10                  15

Asp

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Lys Ser Arg Gly Tyr His Leu Asp Glu
1               5                   10

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Asn Asn Met Asp
1               5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 118

Asp Ile Asn Thr Arg Ser Gly Gly Ser Ile Tyr Asn Glu Glu Phe Gln
1               5                   10                  15

Asp

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Lys Ser Tyr Gly Tyr Tyr Leu Asp Glu
1               5                   10

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Asn Asn Met His
1               5

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Ile Asn Thr Arg Ser Gly Gly Ser Ile Tyr Asn Glu Glu Phe Gln
1               5                   10                  15

Asp

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Lys Ser Tyr Gly Tyr His Leu Asp Glu
1               5                   10

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Asn Asn Met Asp
1               5
```

```
<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asp Ile Asn Thr Arg Ser Gly Gly Ser Ile Tyr Asn Glu Glu Phe Gln
1               5                   10                  15

Asp

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Lys Ser Tyr Gly Asn His Leu Asp Glu
1               5                   10

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Asn Asn Met Asp
1               5

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Asp Ile Asn Thr Arg Ser Gly Gly Ser Ile Tyr Asn Glu Glu Phe Gln
1               5                   10                  15

Asp

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Lys Ser Tyr Gly Tyr Tyr Leu Asp Glu
1               5                   10

<210> SEQ ID NO 129
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 129

Asp Asn Asn Met Asp
1               5

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Ile Asn Thr Arg Ser Gly Gly Ser Ile Tyr Asn Glu Glu Phe Gln
1               5                   10                  15

Asp

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Lys Ser Tyr Gly Tyr His Leu Asp Glu
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Asn Asn Met Asp
1               5

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Ile Asn Thr Lys Ser Gly Gly Ser Ile Tyr Asn Glu Glu Phe Gln
1               5                   10                  15

Asp

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134
```

```
Arg Gln Ser Tyr Gly Tyr His Leu Asp Glu
1               5                   10

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Asn Asn Met Asp
1               5

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Ile Asn Thr Arg Ser Gly Gly Ser Ile Tyr Asn Glu Glu Phe Gln
1               5                   10                  15

Asp

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Lys Ser Tyr Gly Tyr His Leu Asp Glu
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Ala Ser Gln Asn Ile Tyr Lys Asn Leu Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Ala Ser Tyr Arg Tyr Ser
1               5

<210> SEQ ID NO 140
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Gln Tyr Tyr Ser Gly Leu Thr
1               5

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Lys Ala Ser Gln Asn Ile Tyr Lys Asn Leu Ala
1               5                   10

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ser Ala Ser Tyr Arg Tyr Ser
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Gln Tyr Tyr Ser Pro Pro Leu Thr
1               5

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Ala Ser Lys Asn Ile Glu Arg Asn Leu Ala
1               5                   10

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Ala Ser Arg Lys Glu Ser
```

```
<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gln Gln Tyr Ser Ser Pro Pro Leu Thr
1               5

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Ala Ser Arg Asn Ile Glu Arg Asn Leu Ala
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ala Asp Arg Lys Glu Ser
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Gln Tyr Ser Ser Pro Pro Leu Thr
1               5

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Lys Ala Ser Arg Asn Ile Glu Arg Asn Leu Ala
1               5                   10

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 151

Gln Ala Ser Arg Lys Glu Ser
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Gln Tyr Ser Ser Pro Pro Leu Thr
1               5

<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Lys Ala Ser Arg Asn Ile Glu Arg Gln Leu Ala
1               5                   10

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Ala Ser Arg Lys Glu Ser
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Gln Tyr Ser Ser Pro Pro Leu Thr
1               5

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Lys Ala Ser Arg Asn Ile Glu Arg Gln Leu Ala
1               5                   10

<210> SEQ ID NO 157

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Ala Ser Arg Lys Glu Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Gln Tyr Ser Asp Pro Pro Leu Thr
1               5

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Ala Ser Arg Asn Ile Glu Arg Gln Leu Ala
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ala Ser Arg Lys Glu Ser
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Gln Tyr Ser Asp Pro Pro Leu Thr
1               5

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

```
Lys Ala Ser Arg Asn Ile Glu Arg Gln Leu Ala
1               5                   10
```

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Arg Ala Asp Arg Lys Glu Ser
1               5
```

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Gln Gln Tyr Ser Asp Pro Pro Leu Thr
1               5
```

<210> SEQ ID NO 165
<211> LENGTH: 118
<212> TYPE: PRT
<213> ORGANISM: Homo sapiens

<400> SEQUENCE: 165

```
Glu Val Gln Leu Val Gln Ser Gly Ala Glu Val Gln Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Tyr Ile Asn Pro Ser Ser Gly Tyr Thr Lys Tyr Asn Arg Lys Phe
        50                  55                  60

Arg Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gln Gly Tyr Tyr Leu Asp Tyr Trp Gly Glu Gly Thr
            100                 105                 110

Thr Val Thr Val Ser Ser
        115
```

<210> SEQ ID NO 166
<211> LENGTH: 119
<212> TYPE: PRT
<213> ORGANISM: Homo sapiens

<400> SEQUENCE: 166

```
Glu Val Gln Leu Val Gln Ser Gly Ala Gln Val Lys Lys Pro Gly Ala
1               5                   10                  15

Ser Val Lys Val Ser Cys Lys Ala Ser Gly Tyr Thr Phe Ser Asp Asn
                20                  25                  30

Asn Met Asp Trp Val Arg Gln Ala Pro Gly Lys Gly Leu Glu Trp Met
            35                  40                  45
```

```
Gly Asp Ile Asn Thr Lys Ser Gly Gly Ser Ile Tyr Asn Gln Lys Phe
        50                  55                  60

Lys Gly Arg Val Ile Met Thr Ile Asp Lys Ser Thr Gly Thr Ala Tyr
 65                  70                  75                  80

Met Glu Leu Arg Ser Leu Arg Ser Asp Asp Thr Ala Ile Tyr Tyr Cys
                85                  90                  95

Ala Arg Arg Arg Ser Tyr Gly Tyr Tyr Phe Asp Tyr Trp Gly Arg Gly
                100                 105                 110

Thr Leu Val Thr Val Ser Ser
            115

<210> SEQ ID NO 167
<211> LENGTH: 106
<212> TYPE: PRT
<213> ORGANISM: Homo sapiens

<400> SEQUENCE: 167

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Asn Val Gly Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Ala Ser Gly Val Pro Ser Arg Phe Ser Gly
    50                  55                  60

Ser Arg Tyr Gly Thr Asp Phe Thr Leu Thr Ile Ser Ser Leu Gln Pro
 65                  70                  75                  80

Glu Asp Leu Ala Thr Tyr Tyr Cys Gln Gln Tyr Ser Asn Tyr Ile Thr
                85                  90                  95

Phe Gly Gln Gly Thr Lys Val Glu Ile Lys
                100                 105

<210> SEQ ID NO 168
<211> LENGTH: 326
<212> TYPE: PRT
<213> ORGANISM: Homo sapiens

<400> SEQUENCE: 168

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140
```

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 169
<211> LENGTH: 107
<212> TYPE: PRT
<213> ORGANISM: Homo sapiens

<400> SEQUENCE: 169

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 170
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Val Gln Ser Gly Ser Glu Leu Lys Lys Pro Gly Ala
1               5                   10                  15

```
Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
50                  55                  60

Gln Asp Arg Val Thr Met Thr Ile Asp Lys Ser Thr Gly Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ser Tyr Gly Tyr Tyr His Asp Glu Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430
```

```
Asn His Tyr Thr Gln Lys Ser Leu Ser Leu Ser Leu
            435                 440
```

<210> SEQ ID NO 171
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Asn
            20                  25                  30

Leu Ala Trp Tyr Gln Gln Lys Pro Gly Gln Ala Pro Glu Leu Leu Ile
        35                  40                  45

Tyr Ser Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Leu Ala Thr Tyr Tyr Cys Gln Gln Tyr Tyr Ser Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 172
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
50                  55                  60
```

```
Gln Asp Arg Val Thr Met Thr Ile Asp Lys Ser Thr Gly Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Arg Ser Tyr Gly Tyr Tyr His Asp Glu Trp Gly Glu Gly
            100                 105                 110

Thr Leu Val Thr Val Ser Ser
            115

<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Ile Gln Met Thr Gln Ser Pro Ser Ser Leu Ser Ala Ser Val Gly
  1               5                  10                  15

Asp Arg Val Thr Ile Thr Cys Lys Ala Ser Arg Asn Ile Glu Arg Asn
                 20                  25                  30

Leu Ala Trp Tyr Gln Gln Lys Pro Gly Gln Ala Pro Glu Leu Leu Ile
             35                  40                  45

Tyr Ser Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
 65                  70                  75                  80

Glu Asp Leu Ala Thr Tyr Tyr Cys Gln Gln Tyr Tyr Ser Pro Pro Leu
                 85                  90                  95

Thr Phe Gly Gly Gly Thr Lys Val Glu Ile Lys
            100                 105

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Asn Asn Met Asp
  1               5

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Ile Asn Thr Arg Ser Gly Gly Ser Ile Tyr Asn Glu Glu Phe Gln
  1               5                  10                  15

Asp

<210> SEQ ID NO 176
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 176

Arg Arg Ser Tyr Gly Tyr Tyr His Asp Glu
1               5                   10

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Lys Ala Ser Arg Asn Ile Glu Arg Asn Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Ala Ser Arg Lys Glu Ser
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Gln Tyr Tyr Ser Pro Pro Leu Thr
1               5
```

BISPECIFIC ANTIBODIES

CROSS-REFERENCE TO RELATED APPLICATIONS

This application is the National Stage of International Patent Application No. PCT/JP2011/076486, filed on Nov. 17, 2011, which claims the benefit of Japanese Patent Application Serial No. 2010-257022, filed on Nov. 17, 2010.

TECHNICAL FIELD

The present invention relates to multispecific antigen-binding molecules that functionally substitute for blood coagulation factor VIII, a cofactor that enhances enzymatic reactions, and pharmaceutical compositions comprising such a molecule as an active ingredient.

BACKGROUND ART

Hemophilia A is a bleeding abnormality caused by a hereditary decrease or deficiency of blood coagulation factor VIII (F.VIII) function. Hemophilia A patients are generally administered with an F.VIII formulation for the bleeding (on-demand administration). In recent years, F.VIII formulations are also administered prophylactically to prevent bleeding events (preventive administration; Non-patent Documents 1 and 2). The half-life of F.VIII formulations in blood is approximately 12 to 16 hours. Therefore, for continuous prevention, F.VIII formulations are administered to patients three times a week (Non-patent Documents 3 and 4). In on-demand administrations, F.VIII formulations are also additionally administered when necessary at regular intervals to prevent rebleeding. In addition, the administration of F.VIII formulations is done intravenously. Therefore, there has been a strong need for pharmaceutical agents with a lesser burden than F.VIII formulations.

Occasionally, anti-F.VIII antibodies (inhibitors) develop in hemophilia patients. Such inhibitors cancel the effects of the F.VIII formulations. For bleeding in patients who have developed inhibitors (inhibitor patients), bypass formulations are administered. Their action mechanisms are not dependent on F.VIII function, that is, the function of catalyzing the activation of blood coagulation factor X (F.X) by activated blood coagulation factor IX (F.IXa). Therefore, in some cases, bypass formulations cannot sufficiently stop the bleeding. Accordingly, there has been a strong need for pharmaceutical agents that are not affected by the presence of inhibitors and which can functionally substitute for F.VIII.

Recently, as a means for solving the problem, antibodies that functionally substitute for F.VIII and their use were disclosed (Patent Documents 1, 2, and 3). The antibodies may be effective for acquired hemophilia in which anti-F.VIII autoantibodies are present and for von Willebrand disease caused by an abnormality or deficiency of function of von Willebrand factor (vWF), but the activity of functionally substituting for F.VIII was not always sufficient. Therefore, as pharmaceutical agents exhibiting a high hemostatic effect, antibodies with a higher activity of functionally substituting for F.VIII than the above-mentioned antibodies were desired.

PRIOR ART DOCUMENTS

Patent Document

[Patent Document 1] WO 2005/035754
[Patent Document 2] WO 2005/035756
[Patent Document 3] WO 2006/109592

Non-Patent Document

[Non-patent Document 1] Blood 58, 1-13 (1981)
[Non-patent Document 2] Nature 312, 330-337 (1984)
[Non-patent Document 3] Nature 312, 337-342 (1984)
[Non-patent Document 4] Biochim. Biophys. Acta 871, 268-278 (1986)

SUMMARY OF THE INVENTION

Problems to be Solved by the Invention

An objective of the present invention is to provide multispecific antigen-binding molecules that functionally substitute for F.VIII, a cofactor that enhances enzymatic reactions.

Means for Solving the Problems

As a result of dedicated research, the present inventors succeeded in discovering bispecific antibodies having a better F.Xa generation-promoting activity than known antibodies from among various bispecific antibodies that specifically bind to both F.IX/F.IXa and F.X, and substitute for the cofactor function of F.VIII, that is, the function to promote F.X activation by F.IXa (F.Xa generation-promoting function).

Furthermore, the present inventors succeeded in finding the positions in the amino acid sequences of bispecific antibodies having the activity of functionally substituting for F.VIII that are important for improving the F.Xa generation-promoting activity of these antibodies, and thus they successfully obtained bispecific antibodies in which the activity of functionally substituting for F.VIII is further increased by replacing these amino acids. They also succeeded in obtaining bispecific antibodies which not only have a high activity of functionally substituting for F.VIII, but also have a low F.Xase inhibitory action. Satisfying both of these properties is very difficult.

Specifically, the present invention relates to multispecific antigen-binding molecules that functionally substitute for F.VIII, a cofactor that enhances enzymatic reactions, and pharmaceutical compositions comprising such a molecule as an active ingredient, and specifically relates to the following:

[1] a multispecific antigen-binding molecule that functionally substitutes for blood coagulation factor VIII, which comprises a first antigen-binding site that recognizes blood coagulation factor IX and/or activated blood coagulation factor IX and a second antigen-binding site that recognizes blood coagulation factor X, wherein the functional substitution for blood coagulation factor VIII results from an activated blood coagulation factor X (F.Xa) generation-promoting activity higher than the activity of a bispecific antibody (hA69-KQ/hB26-PF/hAL-AQ) which comprises an H chain comprising SEQ ID NOs: 165 and 166, and a commonly shared L chain comprising SEQ ID NO: 167;

[2] the multispecific antigen-binding molecule of [1], which comprises a first polypeptide comprising a first antigen-binding site that recognizes blood coagulation factor IX and/or activated blood coagulation factor IX and a third polypeptide comprising a third antigen-binding site that recognizes blood coagulation factor IX and/or activated blood coagulation factor IX, as well as a second polypeptide comprising a second antigen-binding site that recognizes blood coagulation factor X and a fourth polypeptide comprising a fourth antigen-binding site that recognizes blood coagulation factor X;

[3] the multispecific antigen-binding molecule of [2], wherein the first polypeptide and the third polypeptide each comprises an antigen-binding site of an H chain or L chain of an antibody against blood coagulation factor IX or activated blood coagulation factor IX, respectively; and the second polypeptide and the fourth polypeptide each comprises an antigen-binding site of an H chain or L chain of an antibody against blood coagulation factor X, respectively;

[4] the multispecific antigen-binding molecule of [3], wherein the antigen-binding site of the first polypeptide comprises an antigen-binding site which comprises H chain CDRs consisting of any one of the amino acid sequences selected from the following (a1) to (a11), or an antigen-binding site functionally equivalent thereto, and the antigen-binding site of the second polypeptide comprises an antigen-binding site which comprises H chain CDRs consisting of any one of the amino acid sequences selected from the following (b1) to (b11), or an antigen-binding site functionally equivalent thereto:

- (a1) an antigen-binding site comprising an H chain CDR 1, 2, and 3 amino acid sequences of SEQ ID NOs: 75, 76, and 77 (H chain CDRs of Q1), respectively;
- (a2) an antigen-binding site comprising an H chain CDR 1, 2, and 3 amino acid sequences of SEQ ID NOs: 78, 79, and 80 (H chain CDRs of Q31), respectively;
- (a3) an antigen-binding site comprising an H chain CDR 1, 2, and 3 amino acid sequences of SEQ ID NOs: 81, 82, and 83 (H chain CDRs of Q64), respectively;
- (a4) an antigen-binding site comprising an H chain CDR 1, 2, and 3 amino acid sequences of SEQ ID NOs: 84, 85, and 86 (H chain CDRs of Q85), respectively;
- (a5) an antigen-binding site comprising the H chain CDR 1, 2, and 3 amino acid sequences of SEQ ID NOs: 87, 88, and 89 (H chain CDRs of Q153), respectively;
- (a6) an antigen-binding site comprising an H chain CDR 1, 2, and 3 amino acid sequences of SEQ ID NOs: 90, 91, and 92 (H chain CDRs of Q354), respectively;
- (a7) an antigen-binding site comprising the H chain CDR 1, 2, and 3 amino acid sequences of SEQ ID NOs: 93, 94, and 95 (H chain CDRs of Q360), respectively;
- (a8) an antigen-binding site comprising the of H chain CDR 1, 2, and 3 amino acid sequences of SEQ ID NOs: 96, 97, and 98 (H chain CDRs of Q405), respectively;
- (a9) an antigen-binding site comprising an H chain CDR 1, 2, and 3 amino acid sequences of SEQ ID NOs: 99, 100, and 101 (H chain CDRs of Q458), respectively;
- (a10) an antigen-binding site comprising an H chain CDR 1, 2, and 3 amino acid sequences of SEQ ID NOs: 102, 103, and 104 (H chain CDRs of Q460), respectively;
- (a11) an antigen-binding site comprising an H chain CDR 1, 2, and 3 amino acid sequences of SEQ ID NOs: 105, 106, and 107 (H chain CDRs of Q499), respectively;
- (b1) an antigen-binding site comprising an H chain CDR 1, 2, and 3 amino acid sequences of SEQ ID NOs: 108, 109, and 110 (H chain CDRs of J232), respectively;
- (b2) an antigen-binding site comprising an H chain CDR 1, 2, and 3 amino acid sequences of SEQ ID NOs: 111, 112, and 113 (H chain CDRs of J259), respectively;
- (b3) an antigen-binding site comprising an H chain CDR 1, 2, and 3 amino acid sequences of SEQ ID NOs: 114, 115, and 116 (H chain CDRs of J268), respectively;
- (b4) an antigen-binding site comprising an H chain CDR 1, 2, and 3 amino acid sequences of SEQ ID NOs: 117, 118, and 119 (H chain CDRs of J300), respectively;
- (b5) an antigen-binding site comprising an H chain CDR 1, 2, and 3 amino acid sequences of SEQ ID NOs: 120, 121, and 122 (H chain CDRs of J321), respectively;
- (b6) an antigen-binding site comprising the H chain CDR 1, 2, and 3 amino acid sequences of SEQ ID NOs: 123, 124, and 125 (H chain CDRs of J326), respectively;
- (b7) an antigen-binding site comprising an H chain CDR 1, 2, and 3 amino acid sequences of SEQ ID NOs: 126, 127, and 128 (H chain CDRs of J327), respectively;
- (b8) an antigen-binding site comprising an H chain CDR 1, 2, and 3 amino acid sequences of SEQ ID NOs: 129, 130, and 131 (H chain CDRs of J339), respectively;
- (b9) an antigen-binding site comprising an H chain CDR 1, 2, and 3 amino acid sequences of SEQ ID NOs: 132, 133, and 134 (H chain CDRs of J344), respectively;
- (b10) an antigen-binding site comprising an H chain CDR 1, 2, and 3 amino acid sequences of SEQ ID NOs: 135, 136, and 137 (H chain CDRs of J346), respectively; and
- (b11) an antigen-binding site comprising an H chain CDR 1, 2, and 3 amino acid sequences of SEQ ID NOs: 174, 175, and 176 (H chain CDRs of J142), respectively;

[5] the multispecific antigen-binding molecule of [3], wherein the antigen-binding site of the first polypeptide comprises an antigen-binding site which comprises an H chain variable region consisting of any one of the amino acid sequences selected from the following (a1) to (a11), or an antigen-binding site functionally equivalent thereto, and the antigen-binding site of the second polypeptide comprises an antigen-binding site which comprises an H chain variable region consisting of any one of the amino acid sequences selected from the following (b1) to (b11), or an antigen-binding site functionally equivalent thereto:

- (a1) an antigen-binding site comprising an H chain variable region amino acid sequence of SEQ ID NO: 35 (H chain variable region of Q1);
- (a2) an antigen-binding site comprising an H chain variable region amino acid sequence of SEQ ID NO: 36 (H chain variable region of Q31);
- (a3) an antigen-binding site comprising an H chain variable region amino acid sequence of SEQ ID NO: 37 (H chain variable region of Q64);
- (a4) an antigen-binding site comprising an H chain variable region amino acid sequence of SEQ ID NO: 38 (H chain variable region of Q85);
- (a5) an antigen-binding site comprising an H chain variable region amino acid sequence of SEQ ID NO: 39 (H chain variable region of Q153);
- (a6) an antigen-binding site comprising an H chain variable region amino acid sequence of SEQ ID NO: 40 (H chain variable region of Q354);
- (a7) an antigen-binding site comprising an H chain variable region amino acid sequence of SEQ ID NO: 41 (H chain variable region of Q360);
- (a8) an antigen-binding site comprising an H chain variable region amino acid sequence of SEQ ID NO: 42 (H chain variable region of Q405);
- (a9) an antigen-binding site comprising an H chain variable region amino acid sequence of SEQ ID NO: 43 (H chain variable region of Q458);
- (a10) an antigen-binding site comprising an H chain variable region amino acid sequence of SEQ ID NO: 44 (H chain variable region of Q460);
- (a11) an antigen-binding site comprising an H chain variable region amino acid sequence of SEQ ID NO: 45 (H chain variable region of Q499);
- (b1) an antigen-binding site comprising an H chain variable region amino acid sequence of SEQ ID NO: 46 (H chain variable region of J232);

(b2) an antigen-binding site comprising an H chain variable region amino acid sequence of SEQ ID NO: 47 (H chain variable region of J259);
(b3) an antigen-binding site comprising an H chain variable region amino acid sequence of SEQ ID NO: 48 (H chain variable region of J268);
(b4) an antigen-binding site comprising an H chain variable region amino acid sequence of SEQ ID NO: 49 (H chain variable region of J300);
(b5) an antigen-binding site comprising an H chain variable region amino acid sequence of SEQ ID NO: 50 (H chain variable region of J321);
(b6) an antigen-binding site comprising an H chain variable region amino acid sequence of SEQ ID NO: 51 (H chain variable region of J326);
(b7) an antigen-binding site comprising an H chain variable region amino acid sequence of SEQ ID NO: 52 (H chain variable region of J327);
(b8) an antigen-binding site comprising an H chain variable region amino acid sequence of SEQ ID NO: 53 (H chain variable region of J339);
(b9) an antigen-binding site comprising an H chain variable region amino acid sequence of SEQ ID NO: 54 (H chain variable region of J344);
(b10) an antigen-binding site comprising an H chain variable region amino acid sequence of SEQ ID NO: 55 (H chain variable region of J346); and
(b11) an antigen-binding site comprising an H chain variable region amino acid sequence of SEQ ID NO: 172 (H chain variable region of J142);

[6] the multispecific antigen-binding molecule of [3], wherein the antigen-binding sites included in the third polypeptide and the fourth polypeptide comprise an antigen-binding site which comprises L chain CDRs consisting of any one of the amino acid sequences selected from the following (c1) to (c10), or an antigen-binding site functionally equivalent thereto:
 (c1) an antigen-binding site comprising an L chain CDR1, 2, and 3 amino acid sequences of SEQ ID NOs: 138, 139, and 140 (L chain CDR of L2), respectively;
 (c2) an antigen-binding site comprising an L chain CDR1, 2, and 3 amino acid sequences of SEQ ID NOs: 141, 142, and 143 (L chain CDR of L45), respectively;
 (c3) an antigen-binding site comprising an L chain CDR1, 2, and 3 amino acid sequences of SEQ ID NOs: 144, 145, and 146 (L chain CDR of L248), respectively;
 (c4) an antigen-binding site comprising an L chain CDR1, 2, and 3 amino acid sequences of SEQ ID NOs: 147, 148, and 149 (L chain CDR of L324), respectively;
 (c5) an antigen-binding site comprising an L chain CDR1, 2, and 3 amino acid sequences of SEQ ID NOs: 150, 151, and 152 (L chain CDR of L334), respectively;
 (c6) an antigen-binding site comprising an L chain CDR1, 2, and 3 amino acid sequences of SEQ ID NOs: 153, 154, and 155 (L chain CDR of L377), respectively;
 (c7) an antigen-binding site comprising an L chain CDR1, 2, and 3 amino acid sequences of SEQ ID NOs: 156, 157, and 158 (L chain CDR of L404), respectively;
 (c8) an antigen-binding site comprising an L chain CDR1, 2, and 3 amino acid sequences of SEQ ID NOs: 159, 160, and 161 (L chain CDR of L406), respectively;
 (c9) an antigen-binding site comprising an L chain CDR1, 2, and 3 amino acid sequences of SEQ ID NOs: 137, 138, and 139 (L chain CDR of L408), respectively; and
 (c10) an antigen-binding site comprising an L chain CDR1, 2, and 3 amino acid sequences of SEQ ID NOs: 177, 178, and 179 (L chain CDR of L180), respectively;

[7] the multispecific antigen-binding molecule of [3], wherein the antigen-binding sites included in the third polypeptide and the fourth polypeptide comprise an antigen-binding site which comprises an L chain variable region consisting of any one of the amino acid sequences selected from the following (c1) to (c10), or an antigen-binding site functionally equivalent thereto:
 (c1) an antigen-binding site comprising an L chain variable region amino acid sequence of SEQ ID NO: 56 (L chain variable region of L2);
 (c2) an antigen-binding site comprising an L chain variable region amino acid sequence of SEQ ID NO: 57 (L chain variable region of L45);
 (c3) an antigen-binding site comprising an L chain variable region amino acid sequence of SEQ ID NO: 58 (L chain variable region of L248);
 (c4) an antigen-binding site comprising an L chain variable region amino acid sequence of SEQ ID NO: 59 (L chain variable region of L324);
 (c5) an antigen-binding site comprising an L chain variable region amino acid sequence of SEQ ID NO: 60 (L chain variable region of L334);
 (c6) an antigen-binding site comprising an L chain variable region amino acid sequence of SEQ ID NO: 61 (L chain variable region of L377);
 (c7) an antigen-binding site comprising an L chain variable region amino acid sequence of SEQ ID NO: 62 (L chain variable region of L404);
 (c8) an antigen-binding site comprising an L chain variable region amino acid sequence of SEQ ID NO: 63 (L chain variable region of L406);
 (c9) an antigen-binding site comprising an L chain variable region amino acid sequence of SEQ ID NO: 64 (L chain variable region of L408); and
 (c10) an antigen-binding site comprising an L chain variable region amino acid sequence of SEQ ID NO: 173 (L chain variable region of L180);

[8] the multispecific antigen-binding molecule of [3], wherein the first and second polypeptides further comprise an antibody H chain constant region, and the third and fourth polypeptides comprise an antibody L chain constant region;

[9] the multispecific antigen-binding molecule of [3], wherein the first and second polypeptides comprise an antibody H chain constant region, and the third and fourth polypeptides comprise an antibody L chain constant region, and wherein the third polypeptide and the fourth polypeptide are a commonly shared L chain;

[10] the multispecific antigen-binding molecule of [8] or [9], wherein the first polypeptide comprises an antibody H chain constant region consisting of any one of the amino acid sequences selected from the group consisting of the following (d1) to (d6) or the group consisting of the following (d7) to (d9), and the second polypeptide comprises an antibody H chain constant region consisting of any one of the amino acid sequences selected from a group different from that of the above-mentioned first polypeptide:
 (d1) an H chain constant region of SEQ ID NO: 65 (G4k);
 (d2) an H chain constant region of SEQ ID NO: 66 (z7);
 (d3) an H chain constant region of SEQ ID NO: 67 (z55);
 (d4) an H chain constant region of SEQ ID NO: 68 (z106);
 (d5) an H chain constant region of SEQ ID NO: 69 (z118);
 (d6) an H chain constant region of SEQ ID NO: 70 (z121);
 (d7) an H chain constant region of SEQ ID NO: 71 (G4h);
 (d8) an H chain constant region of SEQ ID NO: 72 (z107); and
 (d9) an H chain constant region of SEQ ID NO: 73 (z119);

[11] the multispecific antigen-binding molecule of [8] or [9], wherein the third and fourth polypeptides comprise the antibody L chain constant region consisting of the following amino acid sequence of:
(e) an L chain constant region of SEQ ID NO: 74 (k);
[12] the multispecific antigen-binding molecule of [8] or [9], wherein the first polypeptide comprises any one antibody H chain selected from the following (a1) to (a14), the second polypeptide comprises any one antibody H chain selected from the following (b1) to (b12), and the third polypeptide and the fourth polypeptide comprise any one antibody L chain selected from the following (c1) to (c10):
 (a1) an antibody H chain consisting of the amino acid sequence of SEQ ID NO: 1 (Q1-G4k);
 (a2) an antibody H chain consisting of the amino acid sequence of SEQ ID NO: 2 (Q31-z7);
 (a3) an antibody H chain consisting of the amino acid sequence of SEQ ID NO: 3 (Q64-z55);
 (a4) an antibody H chain consisting of the amino acid sequence of SEQ ID NO: 10 (Q64-z7);
 (a5) an antibody H chain consisting of the amino acid sequence of SEQ ID NO: 11 (Q85-G4k);
 (a6) an antibody H chain consisting of the amino acid sequence of SEQ ID NO: 12 (Q153-G4k);
 (a7) an antibody H chain consisting of the amino acid sequence of SEQ ID NO: 13 (Q354-z106);
 (a8) an antibody H chain consisting of the amino acid sequence of SEQ ID NO: 14 (Q360-G4k);
 (a9) an antibody H chain consisting of the amino acid sequence of SEQ ID NO: 15 (Q360-z118);
 (a10) an antibody H chain consisting of the amino acid sequence of SEQ ID NO: 16 (Q405-G4k);
 (a11) an antibody H chain consisting of the amino acid sequence of SEQ ID NO: 17 (Q458-z106);
 (a12) an antibody H chain consisting of the amino acid sequence of SEQ ID NO: 18 (Q460-z121);
 (a13) an antibody H chain consisting of the amino acid sequence of SEQ ID NO: 19 (Q499-z118);
 (a14) an antibody H chain consisting of the amino acid sequence of SEQ ID NO: 20 (Q499-z121);
 (b1) an antibody H chain consisting of the amino acid sequence of SEQ ID NO: 4 (J268-G4h);
 (b2) an antibody H chain consisting of the amino acid sequence of SEQ ID NO: 5 (J321-G4h);
 (b3) an antibody H chain consisting of the amino acid sequence of SEQ ID NO: 6 (J326-z107);
 (b4) an antibody H chain consisting of the amino acid sequence of SEQ ID NO: 7 (J344-z107);
 (b5) an antibody H chain consisting of the amino acid sequence of SEQ ID NO: 21 (J232-G4h);
 (b6) an antibody H chain consisting of the amino acid sequence of SEQ ID NO: 22 (J259-z107);
 (b7) an antibody H chain consisting of the amino acid sequence of SEQ ID NO: 23 (J300-z107);
 (b8) an antibody H chain consisting of the amino acid sequence of SEQ ID NO: 24 (J327-z107);
 (b9) an antibody H chain consisting of the amino acid sequence of SEQ ID NO: 25 (J327-z119);
 (b10) an antibody H chain consisting of the amino acid sequence of SEQ ID NO: 26 (J339-z119);
 (b11) an antibody H chain consisting of the amino acid sequence of SEQ ID NO: 27 (J346-z107);
 (b12) an antibody H chain consisting of the amino acid sequence of SEQ ID NO: 170 (J142-G4h);
 (c1) an antibody L chain consisting of the amino acid sequence of SEQ ID NO: 8 (L2-k);
 (c2) an antibody L chain consisting of the amino acid sequence of SEQ ID NO: 9 (L45-k);
 (c3) an antibody L chain consisting of the amino acid sequence of SEQ ID NO: 28 (L248-k);
 (c4) an antibody L chain consisting of the amino acid sequence of SEQ ID NO: 29 (L324-k);
 (c5) an antibody L chain consisting of the amino acid sequence of SEQ ID NO: 30 (L334-k);
 (c6) an antibody L chain consisting of the amino acid sequence of SEQ ID NO: 31 (L377-k);
 (c7) an antibody L chain consisting of the amino acid sequence of SEQ ID NO: 32 (L404-k);
 (c8) an antibody L chain consisting of the amino acid sequence of SEQ ID NO: 33 (L406-k);
 (c9) an antibody L chain consisting of the amino acid sequence of SEQ ID NO: 34 (L408-k); and
 (c10) an antibody L chain consisting of the amino acid sequence of SEQ ID NO: 171 (L180-k);
[13] the multispecific antigen-binding molecule of [1], wherein the first polypeptide comprises an antigen-binding site which binds to an epitope overlapping with an epitope that binds to an antibody consisting of the antibody H chain of any one of (a1) to (a14) and the antibody L chain of any one of (c1) to (c10) of [12], and the second polypeptide comprises an antigen-binding site which binds to an epitope overlapping with an epitope that binds to an antibody consisting of the antibody H chain of any one of (b1) to (b12) and the antibody L chain of any one of (c1) to (c10) of [12];
[14] the multispecific antigen-binding molecule of [8] or [9], wherein the first polypeptide comprises any one antibody H chain selected from the following (e1) to (e3), the second polypeptide comprises any one antibody H chain selected from the following (f1) to (f3), and the third polypeptide and the fourth polypeptide comprise any one antibody L chain selected from the following (g1) to (g4):
 (e1) an H chain of an antibody which binds to an epitope overlapping with an epitope bound by an antibody consisting of an antibody H chain of any one of (a1) to (a14) and an antibody L chain of any one of (c1) to (c10), of [12];
 (e2) an antibody H chain, wherein at least one amino acid residue selected from the amino acid residues at positions 34, 35, 49, 61, 62, 96, 98, 100, 100b, and 102 by Kabat numbering in any one antibody H chain selected from (e1) is substituted with another amino acid;
 (e3) an antibody H chain, wherein by Kabat numbering, the amino acid residue at position 34 is isoleucine, the amino acid residue at position 35 is asparagine, glutamine, or serine, the amino acid residue at position 49 is serine, the amino acid residue at position 61 is arginine, the amino acid residue at position 62 is glutamic acid, the amino acid residue at position 96 is serine or threonine, the amino acid residue at position 98 is lysine or arginine, the amino acid residue at position 100 is phenylalanine or tyrosine, the amino acid residue at position 100b is glycine, or the amino acid residue at position 102 is tyrosine in any antibody H chain selected from (e1);
 (f1) an H chain of an antibody which binds to an epitope overlapping with an epitope bound by an antibody consisting of an antibody H chain of any of (b1) to (b12) of [12] and an antibody L chain of any of (c1) to (c10) of [12];
 (f2) an antibody H chain, wherein at least one amino acid residue selected from the amino acid residues at positions 35, 53, 73, 76, 96, 98, 100, and 100a by Kabat numbering in any antibody H chain of (f1) is substituted with another amino acid;
(f3) an antibody H chain, wherein by Kabat numbering, the amino acid residue at position 35 is aspartic acid, the amino acid residue at position 53 is arginine, the amino acid residue at position 73 is lysine, the amino acid residue at position 76 is glycine, the amino acid residue at position 96 is lysine or arginine, the amino acid residue at position 98 is tyrosine, the amino acid residue at position 100 is tyrosine, or the amino acid residue at position 100a is histidine in any one antibody H chain selected from (f1);
(g1) an L chain of an antibody which binds to an epitope overlapping with an epitope bound by an antibody which consists of an antibody H chain of any one of (a1) to (a14) and an antibody L chain of any one of (c1) to (c10), of [12];
(g2) an L chain of an antibody which binds to an epitope overlapping with an epitope bound by an antibody which consists of an antibody H chain of any one of (b1) to (b12) and an antibody L chain of any one of (c1) to (c10), of [12];
(g3) an antibody L chain, wherein at least one amino acid residue selected from the amino acid residues at positions 27, 30, 31, 32, 50, 52, 53, 54, 55, 92, 93, 94, and 95 by Kabat numbering in the antibody L chain of either (g1) or (g2) is substituted with another amino acid; and
(g4) an antibody L chain, wherein by Kabat numbering, the amino acid residue at position 27 is lysine or arginine, the amino acid residue at position 30 is glutamic acid, the amino acid residue at position 31 is arginine, the amino acid residue at position 32 is glutamine, the amino acid residue at position 50 is arginine or glutamine, the amino acid residue at position 52 is serine, the amino acid residue at position 53 is arginine, the amino acid residue at position 54 is lysine, the amino acid residue at position 55 is glutamic acid, the amino acid residue at position 92 is serine, the amino acid residue at position 93 is serine, the amino acid residue at position 94 is proline, or the amino acid residue at position 95 is proline in the antibody L chain of either (g1) or (g2).
[15] the multispecific antigen-binding molecule of any one of [1] to [14], wherein the multispecific antigen-binding molecule is a multispecific antibody;
[16] a bispecific antibody of any one of the following (a) to (u):
  (a) a bispecific antibody (Q1-G4k/J268-G4h/L45-k), wherein the first polypeptide is an H chain consisting of the amino acid sequence of SEQ ID NO: 1, the second polypeptide is an H chain consisting of the amino acid sequence of SEQ ID NO: 4, and the third polypeptide and the fourth polypeptide are a commonly shared L chain of SEQ ID NO: 9;
  (b) a bispecific antibody (Q1-G4k/J321-G4h/L45-k), wherein the first polypeptide is an H chain consisting of the amino acid sequence of SEQ ID NO: 1, the second polypeptide is an H chain consisting of the amino acid sequence of SEQ ID NO: 5, and the third polypeptide and the fourth polypeptide are a commonly shared L chain of SEQ ID NO: 9;
  (c) a bispecific antibody (Q31-z7/J326-z107/L2-k), wherein the first polypeptide is an H chain consisting of the amino acid sequence of SEQ ID NO: 2, the second polypeptide is an H chain consisting of the amino acid sequence of SEQ ID NO: 6, and the third polypeptide and the fourth polypeptide are a commonly shared L chain of SEQ ID NO: 8;
  (d) a bispecific antibody (Q64-z55/J344-z107/L45-k), wherein the first polypeptide is an H chain consisting of the amino acid sequence of SEQ ID NO: 3, the second polypeptide is an H chain consisting of the amino acid sequence of SEQ ID NO: 7, and the third polypeptide and the fourth polypeptide are a commonly shared L chain of SEQ ID NO: 9;
  (e) a bispecific antibody (Q64-z7/J326-z107/L334-k), wherein the first polypeptide is an H chain consisting of the amino acid sequence of SEQ ID NO: 10, the second polypeptide is an H chain consisting of the amino acid sequence of SEQ ID NO: 6, and the third polypeptide and the fourth polypeptide are a commonly shared L chain of SEQ ID NO: 30;
  (f) a bispecific antibody (Q64-z7/J344-z107/L406-k), wherein the first polypeptide is an H chain consisting of the amino acid sequence of SEQ ID NO: 10, the second polypeptide is an H chain consisting of the amino acid sequence of SEQ ID NO: 7, and the third polypeptide and the fourth polypeptide are a commonly shared L chain of SEQ ID NO: 33;
  (g) a bispecific antibody (Q85-G4k/J268-G4h/L406-k), wherein the first polypeptide is an H chain consisting of the amino acid sequence of SEQ ID NO: 11, the second polypeptide is an H chain consisting of the amino acid sequence of SEQ ID NO: 4, and the third polypeptide and the fourth polypeptide are a commonly shared L chain of SEQ ID NO: 33;
  (h) a bispecific antibody (Q85-G4k/J321-G4h/L334-k), wherein the first polypeptide is an H chain consisting of the amino acid sequence of SEQ ID NO: 11, the second polypeptide is an H chain consisting of the amino acid sequence of SEQ ID NO: 5, and the third polypeptide and the fourth polypeptide are a commonly shared L chain of SEQ ID NO: 30;
  (i) a bispecific antibody (Q153-G4k/J232-G4h/L406-k), wherein the first polypeptide is an H chain consisting of the amino acid sequence of SEQ ID NO: 12, the second polypeptide is an H chain consisting of the amino acid sequence of SEQ ID NO: 21, and the third polypeptide and the fourth polypeptide are a commonly shared L chain of SEQ ID NO: 33;
  (j) a bispecific antibody (Q354-z106/J259-z107/L324-k), wherein the first polypeptide is an H chain consisting of the amino acid sequence of SEQ ID NO: 13, the second polypeptide is an H chain consisting of the amino acid sequence of SEQ ID NO: 22, and the third polypeptide and the fourth polypeptide are a commonly shared L chain of SEQ ID NO: 29;
  (k) a bispecific antibody (Q360-G4k/J232-G4h/L406-k), wherein the first polypeptide is an H chain consisting of the amino acid sequence of SEQ ID NO: 14, the second polypeptide is an H chain consisting of the amino acid sequence of SEQ ID NO: 21, and the third polypeptide and the fourth polypeptide are a commonly shared L chain of SEQ ID NO: 33;
  (l) a bispecific antibody (Q360-z118/J300-z107/L334-k), wherein the first polypeptide is an H chain consisting of the amino acid sequence of SEQ ID NO: 15, the second polypeptide is an H chain consisting of the amino acid sequence of SEQ ID NO: 23, and the third polypeptide and the fourth polypeptide are a commonly shared L chain of SEQ ID NO: 30;

(m) a bispecific antibody (Q405-G4k/J232-G4h/L248-k), wherein the first polypeptide is an H chain consisting of the amino acid sequence of SEQ ID NO: 16, the second polypeptide is an H chain consisting of the amino acid sequence of SEQ ID NO: 21, and the third polypeptide and the fourth polypeptide are a commonly shared L chain of SEQ ID NO: 28;

(n) a bispecific antibody (Q458-z106/J346-z107/L408-k), wherein the first polypeptide is an H chain consisting of the amino acid sequence of SEQ ID NO: 17, the second polypeptide is an H chain consisting of the amino acid sequence of SEQ ID NO: 27, and the third polypeptide and the fourth polypeptide are a commonly shared L chain of SEQ ID NO: 34;

(o) a bispecific antibody (Q460-z121/J327-z119/L334-k), wherein the first polypeptide is an H chain consisting of the amino acid sequence of SEQ ID NO: 18, the second polypeptide is an H chain consisting of the amino acid sequence of SEQ ID NO: 25, and the third polypeptide and the fourth polypeptide are a commonly shared L chain of SEQ ID NO: 30;

(p) a bispecific antibody (Q499-z118/J327-z107/L334-k), wherein the first polypeptide is an H chain consisting of the amino acid sequence of SEQ ID NO: 19, the second polypeptide is an H chain consisting of the amino acid sequence of SEQ ID NO: 24, and the third polypeptide and the fourth polypeptide are a commonly shared L chain of SEQ ID NO: 30;

(q) a bispecific antibody (Q499-z118/J327-z107/L377-k), wherein the first polypeptide is an H chain consisting of the amino acid sequence of SEQ ID NO: 19, the second polypeptide is an H chain consisting of the amino acid sequence of SEQ ID NO: 24, and the third polypeptide and the fourth polypeptide are a commonly shared L chain of SEQ ID NO: 31;

(r) a bispecific antibody (Q499-z118/J346-z107/L248-k), wherein the first polypeptide is an H chain consisting of the amino acid sequence of SEQ ID NO: 19, the second polypeptide is an H chain consisting of the amino acid sequence of SEQ ID NO: 27, and the third polypeptide and the fourth polypeptide are a commonly shared L chain of SEQ ID NO: 28;

(s) a bispecific antibody (Q499-z121/J327-z119/L404-k), wherein the first polypeptide is an H chain consisting of the amino acid sequence of SEQ ID NO: 20, the second polypeptide is an H chain consisting of the amino acid sequence of SEQ ID NO: 25, and the third polypeptide and the fourth polypeptide are a commonly shared L chain of SEQ ID NO: 32;

(t) a bispecific antibody (Q499-z121/J339-z119/L377-k), wherein the first polypeptide is an H chain consisting of the amino acid sequence of SEQ ID NO: 20, the second polypeptide is an H chain consisting of the amino acid sequence of SEQ ID NO: 26, and the third polypeptide and the fourth polypeptide are a commonly shared L chain of SEQ ID NO: 31; and (u) a bispecific antibody (Q153-G4k/J142-G4h/L180-k), wherein the first polypeptide is an H chain consisting of the amino acid sequence of SEQ ID NO: 12, the second polypeptide is an H chain consisting of the amino acid sequence of SEQ ID NO: 170, and the third polypeptide and the fourth polypeptide are a commonly shared L chain of SEQ ID NO: 171;

[17] a nucleic acid encoding the multispecific antigen-binding molecule of any one of [1] to [15] or the bispecific antibody of [16];

[18] a vector inserted with the nucleic acid of [17];

[19] a cell comprising the nucleic acid of [17] or the vector of [18];

[20] a method for producing the multispecific antigen-binding molecule of any one of [1] to [15] or the bispecific antibody of [16] by culturing the cell of [19];

[21] a pharmaceutical composition comprising the multispecific antigen-binding molecule of any one of [1] to [15] or the bispecific antibody of [16], and a pharmaceutically acceptable carrier;

[22] the composition of [21], which is a pharmaceutical composition used for prevention and/or treatment of bleeding, a disease accompanying bleeding, or a disease caused by bleeding;

[23] the composition of [22], wherein the bleeding, the disease accompanying bleeding, or the disease caused by bleeding is a disease that develops and/or progresses due to a decrease or deficiency in the activity of blood coagulation factor VIII and/or activated blood coagulation factor VIII;

[24] the composition of [23], wherein the disease that develops and/or progresses due to a decrease or deficiency in the activity of blood coagulation factor VIII and/or activated blood coagulation factor VIII is hemophilia A;

[25] the composition of [23], wherein the disease that develops and/or progresses due to a decrease or deficiency in the activity of blood coagulation factor VIII and/or activated blood coagulation factor VIII is a disease showing emergence of an inhibitor against blood coagulation factor VIII and/or activated blood coagulation factor VIII;

[26] the composition of [23], wherein the disease that develops and/or progresses due to a decrease or deficiency in the activity of blood coagulation factor VIII and/or activated blood coagulation factor VIII is acquired hemophilia;

[27] the composition of [23], wherein the disease that develops and/or progresses due to a decrease in the activity of blood coagulation factor VIII and/or activated blood coagulation factor VIII is von Willebrand disease;

[28] a method for preventing and/or treating bleeding, a disease accompanying bleeding, or a disease caused by bleeding, which comprises the step of administering the multispecific antigen-binding molecule of any one of [1] to [15] or the bispecific antibody of [16], or the composition of any one of [21] to [27]; and

[29] a kit for use in the prevention and/or treatment method of [28], which comprises at least the multispecific antigen-binding molecule of any one of [1] to [15] or the bispecific antibody of [16], or the composition of any one of [21] to [27].

Furthermore, the present invention relates to:

[30] use of the multispecific antigen-binding molecule of any one of [1] to [15], the bispecific antibody of [16], or the composition of any one of [21] to [27] in the manufacture of an agent for preventing and/or treating bleeding, a disease accompanying bleeding, or a disease caused by bleeding; and

[31] the multispecific antigen-binding molecule of any one of [1] to [15], the bispecific antibody of [16], or the composition of any one of [21] to [27] for preventing and/or treating bleeding, a disease accompanying bleeding, or a disease caused by bleeding.

The present invention also relates to bispecific antibodies that functionally substitute for F.VIII, a cofactor that enhances enzymatic reactions, and pharmaceutical compositions comprising the antibody as an active ingredient, and more specifically relates to:

[32] a bispecific antibody that functionally substitutes for blood coagulation factor VIII, which comprises a first antigen-binding site that recognizes blood coagulation factor IX and/or activated blood coagulation factor IX and a second antigen-binding site that recognizes blood coagulation factor X, wherein the bispecific antibody is any of the following (a) to (u):

(a) a bispecific antibody (Q1-G4k/J268-G4h/L45-k), wherein the first polypeptide is an H chain consisting of the amino acid sequence of SEQ ID NO: 1, the second polypeptide is an H chain consisting of the amino acid sequence of SEQ ID NO: 4, and the third polypeptide and the fourth polypeptide are a commonly shared L chain of SEQ ID NO: 9;

(b) a bispecific antibody (Q1-G4k/J321-G4h/L45-k), wherein the first polypeptide is an H chain consisting of the amino acid sequence of SEQ ID NO: 1, the second polypeptide is an H chain consisting of the amino acid sequence of SEQ ID NO: 5, and the third polypeptide and the fourth polypeptide are a commonly shared L chain of SEQ ID NO: 9;

(c) a bispecific antibody (Q31-z7/J326-z107/L2-k), wherein the first polypeptide is an H chain consisting of the amino acid sequence of SEQ ID NO: 2, the second polypeptide is an H chain consisting of the amino acid sequence of SEQ ID NO: 6, and the third polypeptide and the fourth polypeptide are a commonly shared L chain of SEQ ID NO: 8;

(d) a bispecific antibody (Q64-z55/J344-z107/L45-k), wherein the first polypeptide is an H chain consisting of the amino acid sequence of SEQ ID NO: 3, the second polypeptide is an H chain consisting of the amino acid sequence of SEQ ID NO: 7, and the third polypeptide and the fourth polypeptide are a commonly shared L chain of SEQ ID NO: 9;

(e) a bispecific antibody (Q64-z7/J326-z107/L334-k), wherein the first polypeptide is an H chain consisting of the amino acid sequence of SEQ ID NO: 10, the second polypeptide is an H chain consisting of the amino acid sequence of SEQ ID NO: 6, and the third polypeptide and the fourth polypeptide are a commonly shared L chain of SEQ ID NO: 30;

(f) a bispecific antibody (Q64-z7/J344-z107/L406-k), wherein the first polypeptide is an H chain consisting of the amino acid sequence of SEQ ID NO: 10, the second polypeptide is an H chain consisting of the amino acid sequence of SEQ ID NO: 7, and the third polypeptide and the fourth polypeptide are a commonly shared L chain of SEQ ID NO: 33;

(g) a bispecific antibody (Q85-G4k/J268-G4h/L406-k), wherein the first polypeptide is an H chain consisting of the amino acid sequence of SEQ ID NO: 11, the second polypeptide is an H chain consisting of the amino acid sequence of SEQ ID NO: 4, and the third polypeptide and the fourth polypeptide are a commonly shared L chain of SEQ ID NO: 33;

(h) a bispecific antibody (Q85-G4k/J321-G4h/L334-k), wherein the first polypeptide is an H chain consisting of the amino acid sequence of SEQ ID NO: 11, the second polypeptide is an H chain consisting of the amino acid sequence of SEQ ID NO: 5, and the third polypeptide and the fourth polypeptide are a commonly shared L chain of SEQ ID NO: 30;

(i) a bispecific antibody (Q153-G4k/J232-G4h/L406-k), wherein the first polypeptide is an H chain consisting of the amino acid sequence of SEQ ID NO: 12, the second polypeptide is an H chain consisting of the amino acid sequence of SEQ ID NO: 21, and the third polypeptide and the fourth polypeptide are a commonly shared L chain of SEQ ID NO: 33;

(j) a bispecific antibody (Q354-z106/J259-z107/L324-k), wherein the first polypeptide is an H chain consisting of the amino acid sequence of SEQ ID NO: 13, the second polypeptide is an H chain consisting of the amino acid sequence of SEQ ID NO: 22, and the third polypeptide and the fourth polypeptide are a commonly shared L chain of SEQ ID NO: 29;

(k) a bispecific antibody (Q360-G4k/J232-G4h/L406-k), wherein the first polypeptide is an H chain consisting of the amino acid sequence of SEQ ID NO: 14, the second polypeptide is an H chain consisting of the amino acid sequence of SEQ ID NO: 21, and the third polypeptide and the fourth polypeptide are a commonly shared L chain of SEQ ID NO: 33;

(l) a bispecific antibody (Q360-z118/J300-z107/L334-k), wherein the first polypeptide is an H chain consisting of the amino acid sequence of SEQ ID NO: 15, the second polypeptide is an H chain consisting of the amino acid sequence of SEQ ID NO: 23, and the third polypeptide and the fourth polypeptide are a commonly shared L chain of SEQ ID NO: 30;

(m) a bispecific antibody (Q405-G4k/J232-G4h/L248-k), wherein the first polypeptide is an H chain consisting of the amino acid sequence of SEQ ID NO: 16, the second polypeptide is an H chain consisting of the amino acid sequence of SEQ ID NO: 21, and the third polypeptide and the fourth polypeptide are a commonly shared L chain of SEQ ID NO: 28;

(n) a bispecific antibody (Q458-z106/J346-z107/L408-k), wherein the first polypeptide is an H chain consisting of the amino acid sequence of SEQ ID NO: 17, the second polypeptide is an H chain consisting of the amino acid sequence of SEQ ID NO: 27, and the third polypeptide and the fourth polypeptide are a commonly shared L chain of SEQ ID NO: 34;

(o) a bispecific antibody (Q460-z121/J327-z119/L334-k), wherein the first polypeptide is an H chain consisting of the amino acid sequence of SEQ ID NO: 18, the second polypeptide is an H chain consisting of the amino acid sequence of SEQ ID NO: 25, and the third polypeptide and the fourth polypeptide are a commonly shared L chain of SEQ ID NO: 30;

(p) a bispecific antibody (Q499-z118/J327-z107/L334-k), wherein the first polypeptide is an H chain consisting of the amino acid sequence of SEQ ID NO: 19, the second polypeptide is an H chain consisting of the amino acid sequence of SEQ ID NO: 24, and the third polypeptide and the fourth polypeptide are a commonly shared L chain of SEQ ID NO: 30;

(q) a bispecific antibody (Q499-z118/J327-z107/L377-k), wherein the first polypeptide is an H chain consisting of the amino acid sequence of SEQ ID NO: 19, the second polypeptide is an H chain consisting of the amino acid sequence of SEQ ID NO: 24, and the third polypeptide and the fourth polypeptide are a commonly shared L chain of SEQ ID NO: 31;

(r) a bispecific antibody (Q499-z118/J346-z107/L248-k), wherein the first polypeptide is an H chain consisting of the amino acid sequence of SEQ ID NO: 19, the second polypeptide is an H chain consisting of the amino acid sequence of SEQ ID NO: 27, and the third polypeptide and the fourth polypeptide are a commonly shared L chain of SEQ ID NO: 28;

(s) a bispecific antibody (Q499-z121/J327-z119/L404-k), wherein the first polypeptide is an H chain consisting of the amino acid sequence of SEQ ID NO: 20, the second polypeptide is an H chain consisting of the amino acid sequence of SEQ ID NO: 25, and the third polypeptide and the fourth polypeptide are a commonly shared L chain of SEQ ID NO: 32;

(t) a bispecific antibody (Q499-z121/J339-z119/L377-k), wherein the first polypeptide is an H chain consisting of the amino acid sequence of SEQ ID NO: 20, the second polypeptide is an H chain consisting of the amino acid sequence of SEQ ID NO: 26, and the third polypeptide and the fourth polypeptide are a commonly shared L chain of SEQ ID NO: 31; and (u) a bispecific antibody (Q153-G4k/J142-G4h/L180-k), wherein the first polypeptide is an H chain consisting of the amino acid sequence of SEQ ID NO: 12, the second polypeptide is an H chain consisting of the amino acid sequence of SEQ ID NO: 170, and the third polypeptide and the fourth polypeptide are a commonly shared L chain of SEQ ID NO: 171;

[33] a nucleic acid encoding the bispecific antibody of [32];
[34] a vector inserted with the nucleic acid of [33];
[35] a cell comprising the nucleic acid of [33] or the vector of [34];
[36] a method for producing the bispecific antibody of [32] by culturing the cell of [35];
[37] a pharmaceutical composition comprising the bispecific antibody of [32], and a pharmaceutically acceptable carrier;
[38] the composition of [37], which is a pharmaceutical composition used for prevention and/or treatment of bleeding, a disease accompanying bleeding, or a disease caused by bleeding;
[39] the composition of [38], wherein the bleeding, the disease accompanying bleeding, or the disease caused by bleeding is a disease that develops and/or progresses due to a decrease or deficiency in the activity of blood coagulation factor VIII and/or activated blood coagulation factor VIII;
[40] the composition of [39], wherein the disease that develops and/or progresses due to a decrease or deficiency in the activity of blood coagulation factor VIII and/or activated blood coagulation factor VIII is hemophilia A;
[41] the composition of [39], wherein the disease that develops and/or progresses due to a decrease or deficiency in the activity of blood coagulation factor VIII and/or activated blood coagulation factor VIII is a disease showing emergence of an inhibitor against blood coagulation factor VIII and/or activated blood coagulation factor VIII;
[42] the composition of [39], wherein the disease that develops and/or progresses due to a decrease or deficiency in the activity of blood coagulation factor VIII and/or activated blood coagulation factor VIII is acquired hemophilia;
[43] the composition of [39], wherein the disease that develops and/or progresses due to a decrease in the activity of blood coagulation factor VIII and/or activated blood coagulation factor VIII is von Willebrand disease;
[44] a method for preventing and/or treating bleeding, a disease accompanying bleeding, or a disease caused by bleeding, which comprises the step of administering the bispecific antibody of [32] or the composition of any one of [37] to [43];
[45] a kit for use in the prevention and/or treatment method of [44], which comprises the bispecific antibody of [32], or the composition of any one of [37] to [43];
[46] use of the bispecific antibody of [32] or the composition of any one of [37] to [43] in the manufacture of an agent for preventing and/or treating bleeding, a disease accompanying bleeding, or a disease caused by bleeding; and
[47] the bispecific antibody of [32] or the composition of any one of [37] to [43] for preventing and/or treating bleeding, a disease accompanying bleeding, or a disease caused by bleeding.

Effects of the Invention

The present invention provides antibodies that recognize both an enzyme and its substrate, which are multispecific antigen-binding molecules having a high activity of functionally substituting for F.VIII. Furthermore, the present invention provides antibodies that recognize both an enzyme and its substrate, which are multispecific antigen-binding molecules having a high activity of functionally substituting for F.VIII and a low F.Xase inhibitory action. Since humanized antibodies are generally thought to have high stability in blood and low immunogenicity, multispecific antibodies of the present invention may be very promising as pharmaceuticals.

Figure 1:
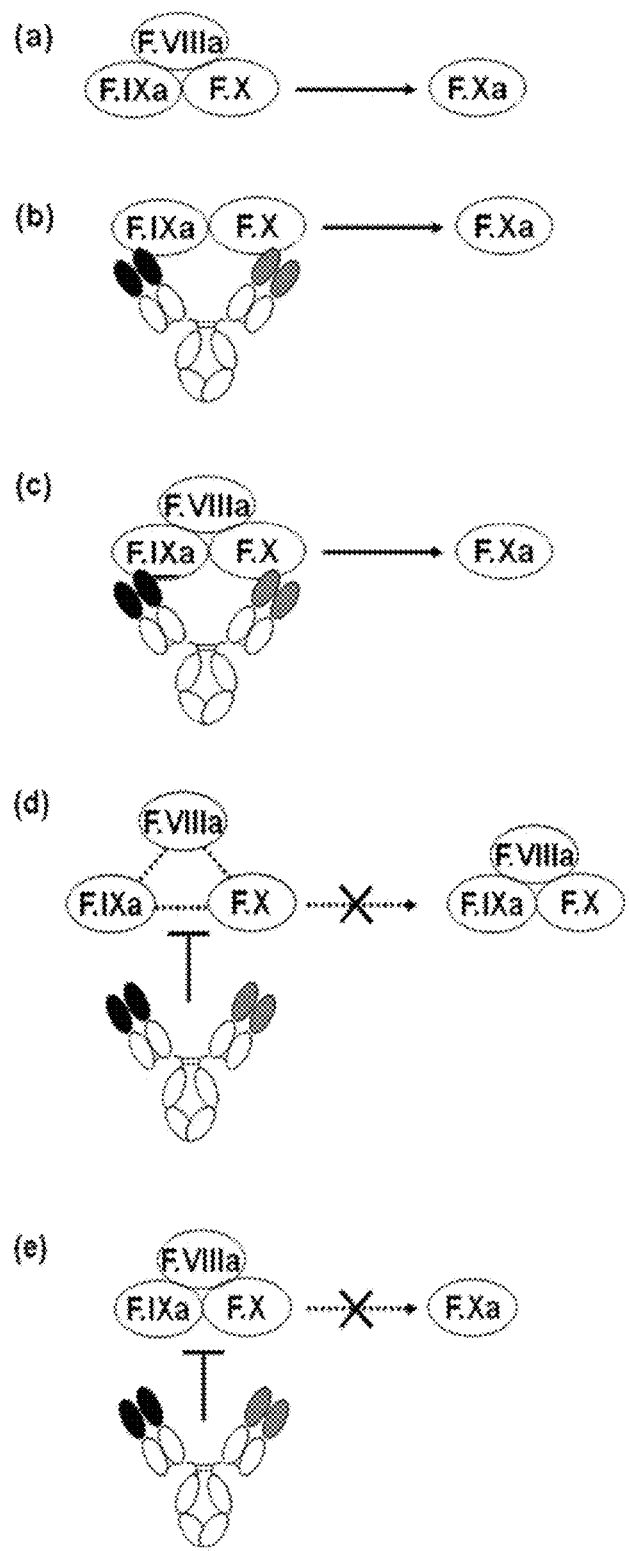
FIG. 1 describes the F.Xase inhibitory action.
(a) F.VIIIa forms a complex with F.IXa (F.Xase) and activates F.X.
(b) A bispecific antibody binds to F.IXa and F.X and activates F.X.
(c) Both F.VIIIa and the bispecific antibody activate F.X without competition.
(d) Binding of the bispecific antibody to F.IXa and/or F.X inhibits the formation of the complex formed between F.Xase and F.X.
(e) Binding of the bispecific antibody to F.IXa and/or F.X inhibits the activity of F.Xase.

The figure shows the effects of hA69-KQ/hB26-PF/hAL-AQ, Q1-G4k/J268-G4h/L45-k, Q31-z7/J326-z107/L2-k, Q1-G4k/J321-G4h/L45-k, Q64-z55/J344-z107/L45-k, Q85-G4k/J268-G4h/L406-k, Q85-G4k/J321-G4h/L334-k, Q64-z7/J344-z107/L406-k, Q64-z7/J326-z107/L334-k, Q153-G4k/J142-G4h/L180-k, Q405-G4k/J232-G4h/L248-k, Q360-G4k/J232-G4h/L406-k, Q153-G4k/J232-G4h/L406-k, Q458-z106/J346-z107/L408-k, Q360-z118/J300-z107/L334-k, Q499-z118/J327-z107/L377-k, Q499-z121/J327-z119/L404-k, Q499-z121/J339-z119/L377-k, Q499-z118/J346-z107/L248-k, Q354-z106/J259-z107/L324-k, Q460-z121/J327-z119/L334-k, and Q499-z118/J327-z107/L334-k on F.X activation by F.IXa in the presence of F.VIIIa. The F.Xase inhibitory actions of the antibodies are indicated as the value obtained by subtracting the absorbance of the antibody-free reaction solution from the absorbance of the antibody-supplemented reaction solution. The concentrations of the antibody solutions were 300 and 30 µg/mL (the concentrations after mixing Human Factor IXa, F.VIIIa, Human Factor X, and the antibody solution were 100 and 10 μg/mL), the enzyme reaction and color development were performed for six minutes and 14 minutes, respectively. The more positive the value of F.Xase inhibitory action shown on the horizontal axis, the weaker the F.Xase inhibitory action is. As a result, hA69-KQ/hB26-PF/hAL-AQ described in WO 2006/109592 showed strong F.Xase inhibitory action. All of the antibodies of the present invention showed weaker F.Xase inhibitory action compared to hA69-KQ/hB26-PF/hAL-AQ, or did not show inhibitory action.

Figure 6A:
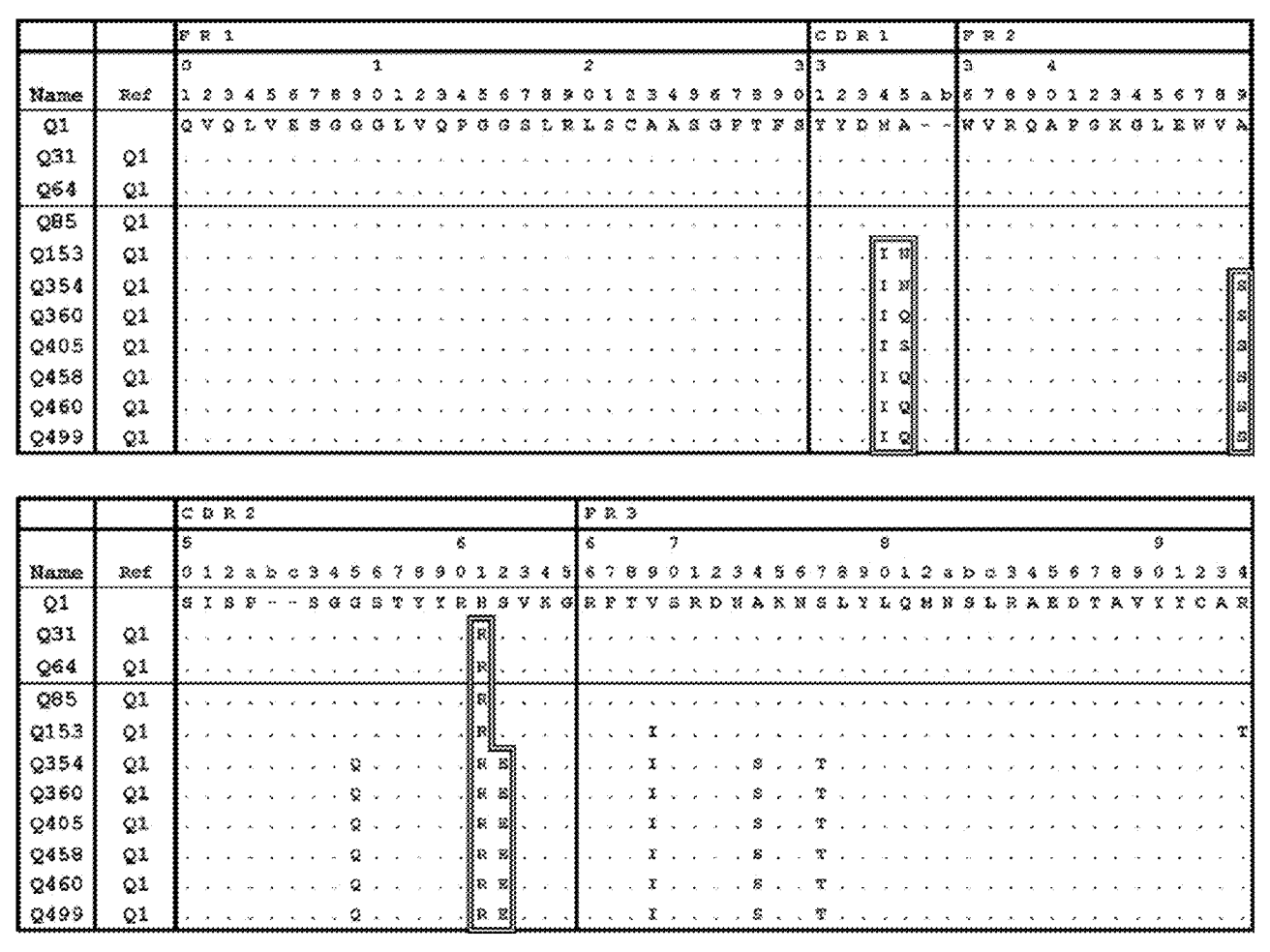
Figure 6B:
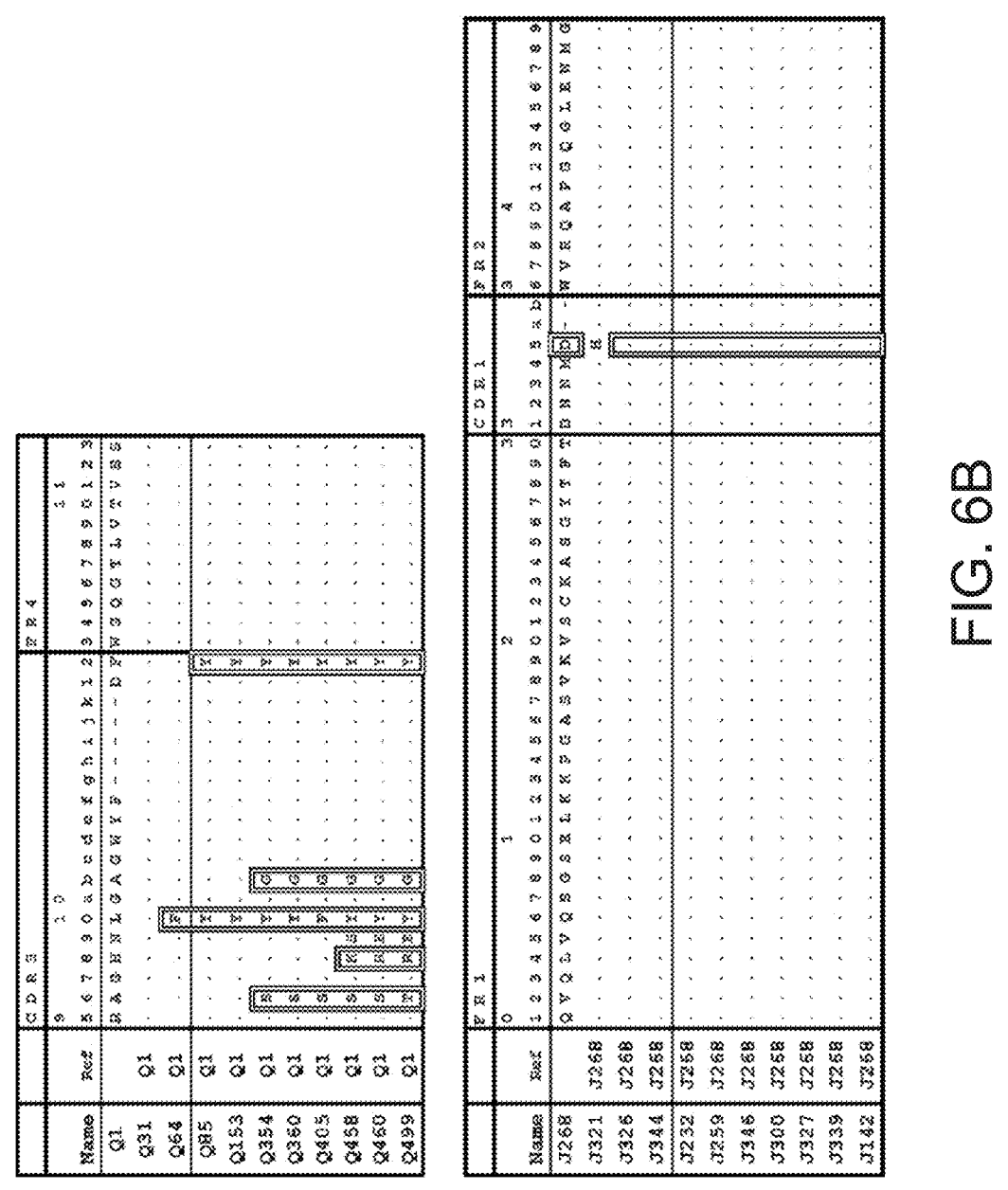
Figure 6C:
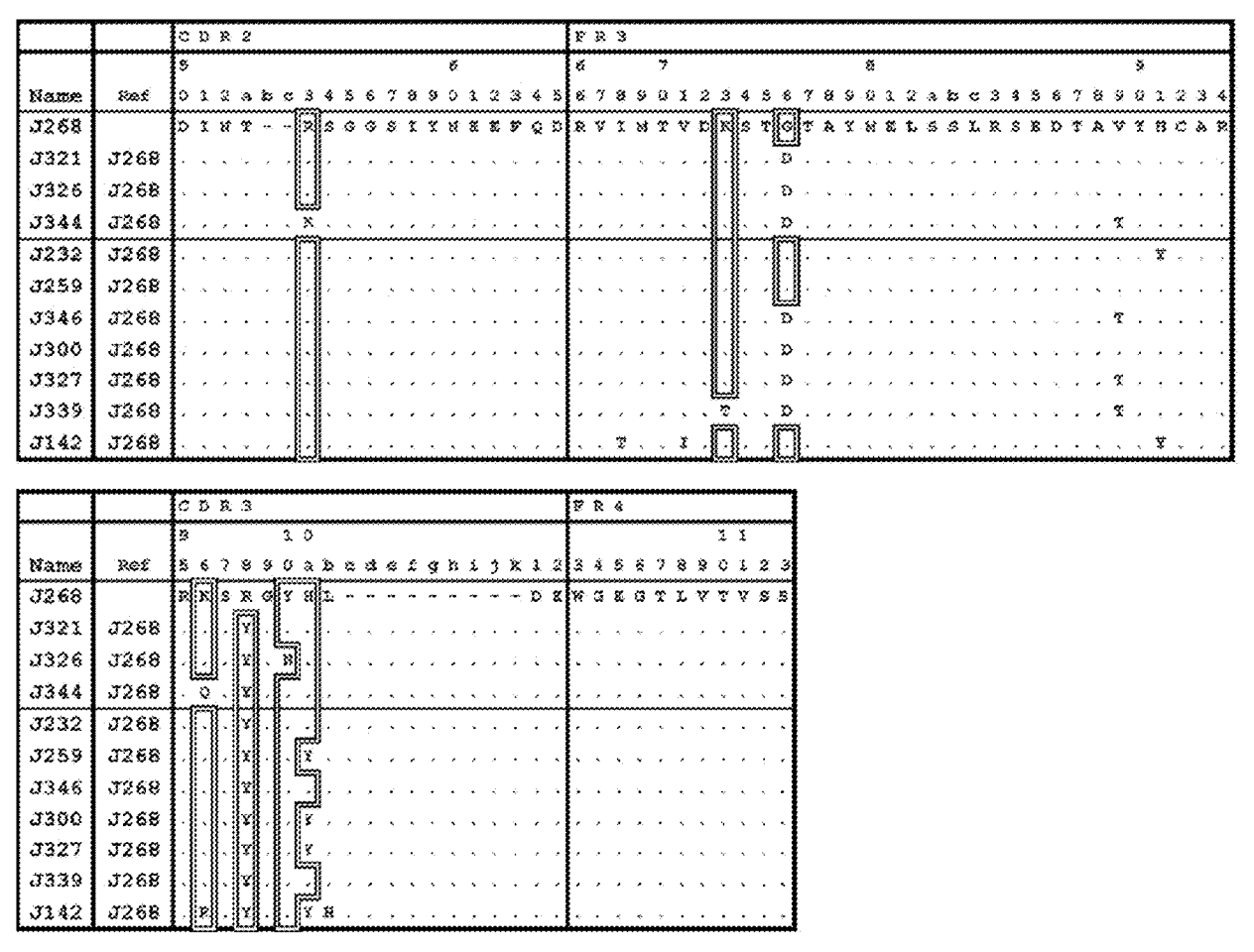
Figure 6D:
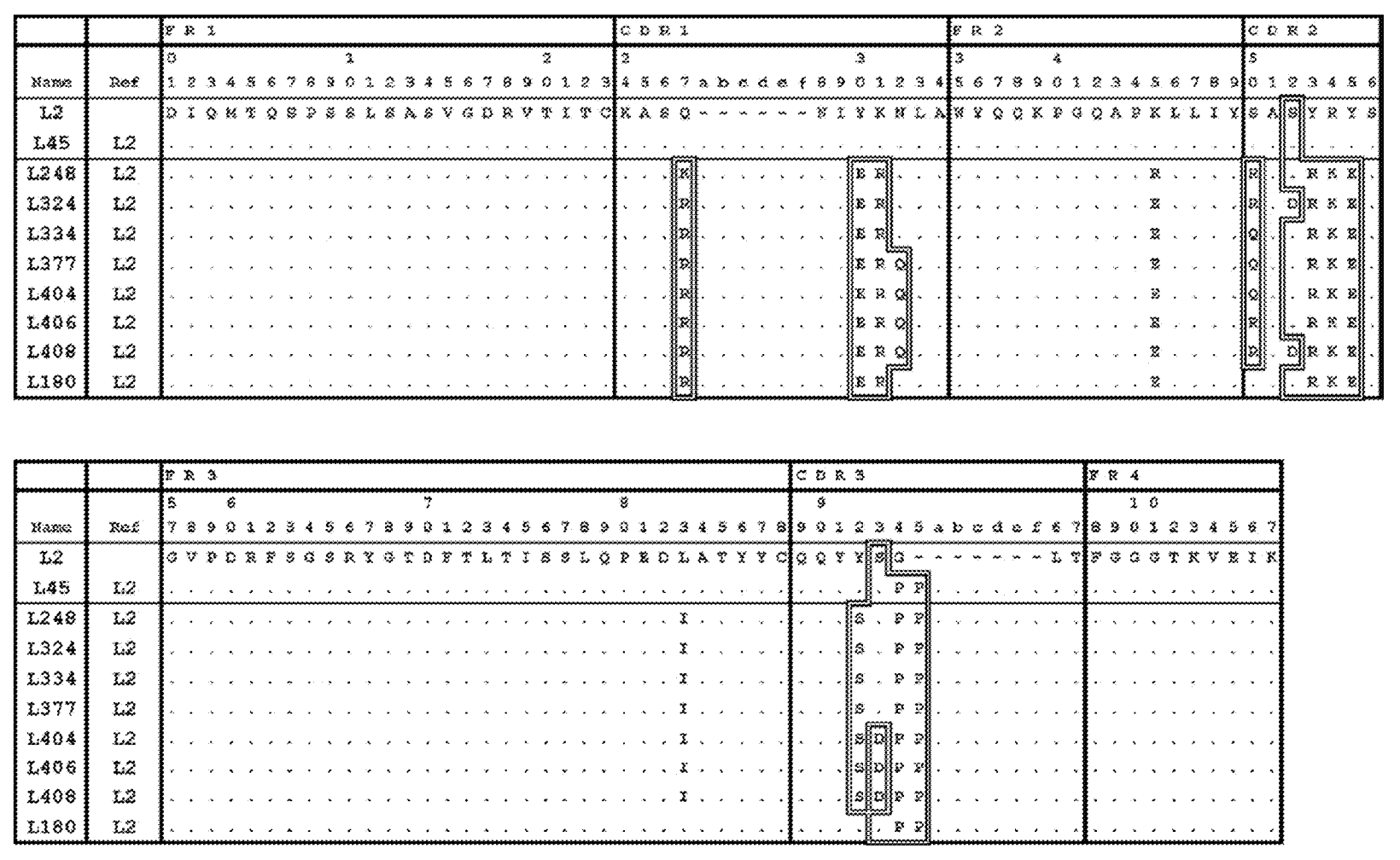

FIG. 6A shows the amino acid sequences of the prototype antibodies and the modified antibodies with amino acid substitutions. When the sequence name is not indicated in the Ref column, the variable region sequence of the Name column is mentioned. A "- (hyphen)" is shown where an amino acid is absent at the number by Kabat numbering. A ". (dot)" is shown where amino acid is the same when comparing the variable region of the Name column and the Ref column, and the amino acid of the variable region of the Name column is shown where the amino acids are different. Amino acids found to be important for improvement of F.Xa generation-promoting activity were indicated by framing them.

FIG. 6B is a continuation of FIG. 6A.

FIG. 6C is a continuation of FIG. 6B.

FIG. 6D is a continuation of FIG. 6C.

The amino acid sequences shown in FIG. 6A through 6D are Q1 (SEQ ID NO: 35), Q31 (SEQ ID NO: 36), Q64 (SEQ ID NO: 37), Q85 (SEQ ID NO: 38), Q153 (SEQ ID NO: 39), Q354 (SEQ ID NO: 40), Q360 (SEQ ID NO: 41), Q405 (SEQ ID NO: 42), Q458 (SEQ ID NO: 43), Q460 (SEQ ID NO: 44), Q499 (SEQ ID NO: 45), J268 (SEQ ID NO: 48), J321 (SEQ ID NO: 50), J326 (SEQ ID NO: 51), J344 (SEQ ID NO: 54), J232 (SEQ ID NO: 46), J259 (SEQ ID NO: 47), J346 (SEQ ID NO: 55), J300 (SEQ ID NO: 49), J327 (SEQ ID NO: 52), J339 (SEQ ID NO: 53), J142 (SEQ ID NO: 172), L2 (SEQ ID NO: 56), L45 (SEQ ID NO: 57), L248 (SEQ ID NO: 58), L324 (SEQ ID NO: 59), L334 (SEQ ID NO: 60), L377 (SEQ ID NO: 61), L404 (SEQ ID NO: 62), L406 (SEQ ID NO: 63), L408 (SEQ ID NO: 64), and L180 (SEQ ID NO: 173).

MODE FOR CARRYING OUT THE INVENTION

Multispecific antigen-binding molecules described herein comprise a first antigen-binding site and a second antigen-binding site that can specifically bind to at least two different types of antigens. While the first antigen-binding site and the second antigen-binding site are not particularly limited as long as they have an activity to bind to F.IX and/or F.IXa, and F.X, respectively, examples include sites necessary for binding with antigens, such as antibodies, scaffold molecules (antibody-like molecules) or peptides, or fragments containing such sites. Scaffold molecules are molecules that exhibit function by binding to target molecules, and any polypeptide may be used as long as they are conformationally stable polypeptides that can bind to at least one target antigen. Examples of such polypeptides include antibody variable regions, fibronectin (WO 2002/032925), protein A domain (WO 1995/001937), LDL receptor A domain (WO 2004/044011, WO 2005/040229), ankyrin (WO 2002/020565), and such, and also molecules described in documents by Nygren et al. (Current Opinion in Structural Biology, 7: 463-469 (1997); and Journal of Immunol Methods, 290: 3-28 (2004)), Binz et al. (Nature Biotech 23: 1257-1266 (2005)), and Hosse et al. (Protein Science 15: 14-27 (2006)). Furthermore, as mentioned in Curr Opin Mol Ther. 2010 August; 12(4): 487-95 and Drugs. 2008; 68(7): 901-12, peptide molecules that can bind to target antigens may be used.

Herein, multispecific antigen-binding molecules are not particularly limited as long as they are molecules that can bind to at least two different types of antigens, but examples include polypeptides containing the above-mentioned antigen-binding sites, such as antibodies and scaffold molecules as well as their fragments, and aptamers comprising nucleic acid molecules and peptides, and they may be single molecules or multimers thereof. Preferred multispecific antigen-binding molecules include multispecific antibodies that can bind specifically to at least two different antigens. Particularly preferred examples of antibodies which have an activity of functionally substituting for F.VIII of the present invention include bispecific antibodies (BsAb) that can bind specifically to two different antigens (they may also be called dual specific antibodies).

In the present invention, the term "commonly shared L chain" refers to an L chain that can link with two or more different H chains, and show binding ability to each antigen. Herein, the term "different H chain(s)" preferably refers to H chains of antibodies against different antigens, but is not limited thereto, and also refers to H chains whose amino acid sequences are different from each other. Commonly shared L chain can be obtained, for example, according to the method described in WO 2006/109592.

The multispecific antigen-binding molecules of the present invention (preferably bispecific antibodies) are antibodies having specificity to two or more different antigens, or molecules comprising fragments of such antibodies. The antibodies of the present invention are not particularly limited, but are preferably monoclonal antibodies. Monoclonal antibodies used in the present invention include not only monoclonal antibodies derived from animals such as humans, mice, rats, hamsters, rabbits, sheep, camels, and monkeys, but also include artificially modified gene recombinant antibodies such as chimeric antibodies, humanized antibodies, and bispecific antibodies.

Furthermore, the L chains of an antibody which will become a multispecific antigen-binding molecule of the present invention may be different, but preferably have commonly shared L chains.

Multispecific antigen-binding molecules of the present invention are preferably recombinant antibodies produced using genetic recombination techniques (See, for example, Borrebaeck C A K and Larrick J W, THERAPEUTIC MONOCLONAL ANTIBODIES, Published in the United Kingdom by MACMILLAN PUBLISHERS LTD, 1990). Recombinant antibodies can be obtained by cloning DNAs encoding antibodies from hybridomas or antibody-producing cells, such as sensitized lymphocytes, that produce antibodies, inserting them into suitable vectors, and then introducing them into hosts (host cells) to produce the antibodies.

Furthermore, antibodies of the present invention may include not only whole antibodies but also antibody fragments and low-molecular-weight antibodies (minibodies), and modified antibodies.

For example, antibody fragments or minibodies include diabodies (Dbs), linear antibodies, and single chain antibody (hereinafter, also denoted as scFvs) molecules. Herein, an "Fv" fragment is defined as the smallest antibody fragment that comprises a complete antigen recognition site and binding site.

An "Fv" fragment is a dimer (VH-VL dimer) in which an H chain variable region (VH) and an L chain variable region (VL) are strongly linked by non-covalent binding. The three complementarity determining regions (CDRs) of each of the variable regions interact with each other to form an antigen-binding site on the surface of the VH-VL dimer. Six CDRs confer the antigen-binding site to an antibody. However, one variable region (or half of the Fv comprising only three CDRs specific to an antigen) alone can recognize and bind to an antigen, though its affinity is lower than that of the entire binding site.

An Fab fragment (also called F(ab)) further comprises an L chain constant region and an H chain constant region (CH1). An Fab' fragment differs from an Fab fragment in that it additionally comprises several residues derived from the carboxyl terminus of the H chain CH1 region, comprising one or more cysteines from the hinge region of the antibody. Fab'-SH refers to an Fab' in which one or more cysteine residues of its constant region comprise a free thiol group. An F(ab') fragment is produced by cleavage of disulfide bonds between the cysteine residues in the hinge region of F(ab')$_2$ pepsin digest. Other chemically bound antibody fragments are also known to those skilled in the art.

Diabodies are bivalent minibodies constructed by gene fusion (Holliger, P. et al., Proc. Natl. Acad. Sci. USA 90: 6444-6448 (1993); EP 404,097; WO 93/11161). Diabodies are dimers consisting of two polypeptide chains, in which each polypeptide chain comprises an L chain variable region (VL) and an H chain variable region (VH) linked with a linker short enough to prevent association of these two domains within the same chain, for example, a linker of preferably 2 to 12 amino acids, more preferably 3 to 10 amino acids, particularly about 5 amino acids. The polypeptide chain form a dimer since the linker between the VL and VH encoded on the same polypeptide is too short to form a single chain variable region fragment. Therefore, diabodies comprise two antigen-binding sites.

A single-chain antibody or an scFv antibody fragment comprises the VH and VL regions of an antibody, and these regions exist in a single polypeptide chain. In general, an Fv polypeptide further comprises a polypeptide linker between the VH and VL regions, and this enables an scFv to form a structure necessary for antigen binding (for a review on scFvs, see Pluckthun "The Pharmacology of Monoclonal Antibodies" Vol. 113 (Rosenburg and Moore ed. (Springer Verlag, New York) pp. 269-315, 1994). In the context of the present invention, linkers are not particularly limited so long as they do not inhibit the expression of the antibody variable regions linked at their ends.

IgG-type bispecific antibodies can be secreted from hybrid hybridomas (quadromas) produced by fusing two kinds of hybridomas that produce IgG antibodies (Milstein C et al. Nature 1983, 305: 537-540). They can also be secreted by taking the L chain and H chain genes constituting the two kinds of IgGs of interest, a total of four kinds of genes, and introducing them into cells to coexpress the genes.

In this case, by introducing suitable amino acid substitutions to the CH3 regions of the H chains, IgGs having a heterogeneous combination of H chains can be preferentially secreted (Ridgway J B et al. Protein Engineering 1996, 9: 617-621; Merchant A M et al. Nature Biotechnology 1998, 16: 677-681; WO 2006/106905; Davis J H et al. Protein Eng Des Sel. 2010, 4: 195-202).

Regarding the L chains, since diversity of L chain variable regions is lower than that of H chain variable regions, commonly shared L chains that can confer binding ability to both H chains may be obtained. The antibodies of the present invention comprise commonly shared L chains. Bispecific IgGs can be efficiently expressed by introducing the genes of the commonly shared L chain and both H chains into cells.

Bispecific antibodies may be produced by chemically crosslinking Fab's. Bispecific F(ab')$_2$ can be produced, for example, by preparing Fab' from an antibody, using it to produce a maleimidized Fab' with ortho-phenylenedi-maleimide (o-PDM), and then reacting this with Fab' prepared from another antibody to crosslink Fab's derived from different antibodies (Keler T et al. Cancer Research 1997, 57: 4008-4014). The method of chemically linking an Fab'-thionitrobenzoic acid (TNB) derivative and an antibody fragment such as Fab'-thiol (SH) is also known (Brennan Metal. Science 1985, 229: 81-83).

Instead of a chemical crosslink, a leucine zipper derived from Fos and Jun may also be used. Preferential formation of heterodimers by Fos and Jun is utilized, even though they also form homodimers. Fab' to which Fos leucine zipper is added, and another Fab' to which Jun leucine zipper is added are expressed and prepared. Monomeric Fab'-Fos and Fab'-Jun reduced under mild conditions are mixed and reacted to form bispecific F(ab')$_2$ (Kostelny S A et al. J. of Immunology, 1992, 148: 1547-53). This method can be applied not only to Fab's but also to scFvs, Fvs, and such.

Furthermore, bispecific antibodies including sc(Fv)$_2$ such as IgG-scFv (Protein Eng Des Sel. 2010 April; 23(4): 221-8) and BiTE (Drug Discov Today. 2005 Sep. 15; 10(18): 1237-44.), DVD-Ig (Nat. Biotechnol. 2007 November; 25(11): 1290-7. Epub 2007 Oct. 14.; and MAbs. 2009 July; 1(4): 339-47. Epub 2009 Jul. 10.), and also others (IDrugs 2010, 13: 698-700) including two-in-one antibodies (Science. 2009 Mar. 20; 323(5921): 1610-4; and Immunotherapy. 2009 September; 1(5): 749-51.), Tri-Fab, tandem scFv, and diabodies are known (MAbs. 2009 November; 1(6): 539-547). In addition, even when using molecular forms such as scFv-Fc and scaffold-Fc, bispecific antibodies can be produced efficiently by preferentially secreting a heterologous combination of Fcs (Ridgway J B et al., Protein Engineering 1996, 9: 617-621; Merchant A M et al. Nature Biotechnology 1998, 16: 677-681; WO 2006/106905; and Davis J H et al., Protein Eng Des Sel. 2010, 4: 195-202.).

A bispecific antibody may also be produced using a diabody. A bispecific diabody is a heterodimer of two cross-over scFv fragments. More specifically, it is produced by forming a heterodimer using VH(A)-VL(B) and VH(B)-VL(A) prepared by linking VHs and VLs derived from two kinds of antibodies, A and B, using a relatively short linker of about 5 residues (Holliger P et al. Proc Natl. Acad. Sci. USA 1993, 90: 6444-6448).

The desired structure can be achieved by linking the two scFvs with a flexible and relatively long linker comprising about 15 residues (single chain diabody: Kipriyanov S M et al. J. of Molecular Biology. 1999, 293: 41-56), and conducting appropriate amino acid substitutions (knobs-into-holes:

Zhu Z et al. Protein Science. 1997, 6: 781-788; VH/VL interface engineering: Igawa T et al. Protein Eng Des Sel. 2010, 8: 667-77).

An sc(Fv)₂ that can be produced by linking two types of scFvs with a flexible and relatively long linker, comprising about 15 residues, may also be a bispecific antibody (Mallender W D et al. J. of Biological Chemistry, 1994, 269: 199-206).

Examples of modified antibodies include antibodies linked to various molecules such as polyethylene glycol (PEG). The antibodies of the present invention include such modified antibodies. In the context of the present invention, the substance to which the modified antibodies are linked is not limited. Such modified antibodies can be obtained by chemically modifying obtained antibodies. Such methods are well established in the art.

The antibodies of the present invention include human antibodies, mouse antibodies, rat antibodies, or such, and their origins are not limited. They may also be genetically modified antibodies, such as chimeric or humanized antibodies.

Methods for obtaining human antibodies are known in the art. For example, transgenic animals carrying the entire repertoire of human antibody genes can be immunized with desired antigens to obtain desired human antibodies (see International Patent Application WO 93/12227, WO 92/03918, WO 94/02602, WO 94/25585, WO 96/34096, and WO 96/33735).

Genetically modified antibodies can also be produced using known methods. Specifically, for example, chimeric antibodies may comprise H chain and L chain variable regions of an immunized animal antibody, and H chain and L chain constant regions of a human antibody. Chimeric antibodies can be obtained by linking DNAs encoding the variable regions of the antibody derived from the immunized animal, with DNAs encoding the constant regions of a human antibody, inserting this into an expression vector, and then introducing it into host cells to produce the antibodies.

Humanized antibodies are modified antibodies often referred to as "reshaped" human antibodies. A humanized antibody is constructed by transferring the CDRs of an antibody derived from an immunized animal to the complementarity determining regions of a human antibody. Conventional genetic recombination techniques for such purposes are known (see European Patent Application Publication No. EP 239400; International Publication No. WO 96/02576; Sato K et al., Cancer Research 1993, 53: 851-856; International Publication No. WO 99/51743).

The multispecific antigen-binding molecules of the present invention are those that recognize F.IX and/or F.IXa, and F.X, and functionally substitute for cofactor function of F.VIII, and characterized in that the molecules have a higher F.Xa generation-promoting activity compared to hA69-KQ/hB26-PF/hAL-AQ (described in WO 2006/109592) which is known as a bispecific antibody that functionally substitutes for F.VIII. Furthermore, antibodies of the present invention usually have a structure which comprises a variable region of an anti-F.IXa antibody and a variable region of an anti-F.X antibody.

More specifically, the present invention provides a multispecific antigen-binding molecule that functionally substitutes for F.VIII, which comprises a first antigen-binding site that recognizes F.IX and/or F.IXa and a second antigen-binding site that recognizes F.X, wherein the function that substitutes for the function of F.VIII is caused by a higher F.Xa generation-promoting activity compared to the activity of the bispecific antibody (hA69-KQ/hB26-PF/hAL-AQ) which comprises H chains consisting of SEQ ID NOs: 165 and 166, and a commonly shared L chain consisting of SEQ ID NO: 167.

A multispecific antigen-binding molecule of the present invention comprises a first polypeptide and a third polypeptide comprising an antigen-binding site that recognizes F.IX and/or F.IXa, and a second polypeptide and a fourth polypeptide comprising an antigen-binding site that recognizes F.X. The first polypeptide and the third polypeptide, and the second polypeptide and the fourth polypeptide each include the antigen-binding site of the antibody H chain and the antigen-binding site of the antibody L chain.

For example, in a multispecific antigen-binding molecule of the present invention, the first polypeptide and the third polypeptide include an antigen-binding site of an H chain and L chain of an antibody against F.IX or F.IXa, respectively; and the second polypeptide and the fourth polypeptide comprise an antigen-binding site of an H chain and L chain of an antibody against F.X, respectively.

At this time, the antigen-binding sites of the antibody L chain included in the first polypeptide and the third polypeptide, and the second polypeptide and the fourth polypeptide may be commonly shared L chains.

A polypeptide comprising an antigen-binding site of an antibody L chain in the present invention is preferably a polypeptide which comprises all or a part of the sequence of the antibody L chain which binds to F.IX, F.IXa and/or F.X.

Preferred embodiments of the antigen-binding site of the first polypeptide of an antibody of the present invention specifically include antigen-binding sites comprising the amino acid sequences of:
Q1 H chain each CDR1, 2, and 3 sequence (SEQ ID NOs: 75, 76, and 77, respectively);
Q31 H chain each CDR1, 2, and 3 sequences (SEQ ID NOs: 78, 79, and 80, respectively);
Q64 H chain each CDR1, 2, and 3 sequence (SEQ ID NOs: 81, 82, and 83, respectively);
Q85 H chain each CDR1, 2, and 3 sequence (SEQ ID NOs: 84, 85, and 86, respectively);
Q153 H chain each CDR1, 2, and 3 sequence (SEQ ID NOs: 87, 88, and 89, respectively);
Q354 H chain each CDR1, 2, and 3 sequence (SEQ ID NOs: 90, 91, and 92, respectively);
Q360 H chain each CDR1, 2, and 3 sequence (SEQ ID NOs: 93, 94, and 95, respectively);
Q405 H chain each CDR1, 2, and 3 sequence (SEQ ID NOs: 96, 97, and 98, respectively);
Q458 H chain each CDR1, 2, and 3 sequence (SEQ ID NOs: 99, 100, and 101, respectively);
Q460 H chain each CDR1, 2, and 3 sequence (SEQ ID NOs: 102, 103, and 104, respectively); and
Q499 H chain each CDR1, 2, and 3 sequence (SEQ ID NOs: 105, 106, and 107, respectively) mentioned in the later-described Examples, or antigen-binding sites that are functionally equivalent to them.

Preferred embodiments of the antigen-binding site of a second polypeptide specifically include, for example, antigen-binding sites comprising the amino acid sequences of:
J232 H chain each CDR1, 2, and 3 sequence (SEQ ID NOs: 108, 109, and 110, respectively);
J259 H chain each CDR1, 2, and 3 sequence (SEQ ID NOs: 111, 112, and 113, respectively);
J268 H chain each CDR1, 2, and 3 sequence (SEQ ID NOs: 114, 115, and 116, respectively);
J300 H chain each CDR1, 2, and 3 sequence (SEQ ID NOs: 117, 118, and 119, respectively);

J321 H chain each CDR1, 2, and 3 sequence (SEQ ID NOs: 120, 121, and 122, respectively);
J326 H chain each CDR1, 2, and 3 sequence (SEQ ID NOs: 123, 124, and 125, respectively);
J327 H chain each CDR1, 2, and 3 sequence (SEQ ID NOs: 126, 127, and 128, respectively);
J339 H chain each CDR1, 2, and 3 sequence (SEQ ID NOs: 129, 130, and 131, respectively);
J344 H chain each CDR1, 2, and 3 sequence (SEQ ID NOs: 132, 133, and 134, respectively);
J346 H chain each CDR1, 2, and 3 sequence (SEQ ID NOs: 135, 136, and 137, respectively); and
J142 H chain each CDR1, 2, and 3 sequence (SEQ ID NOs: 174, 175, and 176, respectively) mentioned in the later-described Examples, or antigen-binding sites that are functionally equivalent to them.

More specifically, the present invention provides multispecific antigen-binding molecules, wherein the antigen-binding site of the first polypeptide comprises an antigen-binding site which comprises H chain CDRs consisting of any one of the amino acid sequences selected from the following (a1) to (a11), or an antigen-binding site functionally equivalent thereto, and the antigen-binding site of the second polypeptide comprises an antigen-binding site which comprises H chain CDRs consisting of any one of the amino acid sequences selected from the following (b1) to (b11), or an antigen-binding site functionally equivalent thereto:

(a1) an antigen-binding site comprising an H chain CDR 1, 2, and 3 amino acid sequences of SEQ ID NOs: 75, 76, and 77 (H chain CDRs of Q1), respectively;
(a2) an antigen-binding site comprising an H chain CDR 1, 2, and 3 amino acid sequences of SEQ ID NOs: 78, 79, and 80 (H chain CDRs of Q31), respectively;
(a3) an antigen-binding site comprising an H chain CDR 1, 2, and 3 amino acid sequences of SEQ ID NOs: 81, 82, and 83 (H chain CDRs of Q64), respectively;
(a4) an antigen-binding site comprising an H chain CDR 1, 2, and 3 amino acid sequences of SEQ ID NOs: 84, 85, and 86 (H chain CDRs of Q85), respectively;
(a5) an antigen-binding site comprising the H chain CDR 1, 2, and 3 amino acid sequences of SEQ ID NOs: 87, 88, and 89 (H chain CDRs of Q153), respectively;
(a6) an antigen-binding site comprising an H chain CDR 1, 2, and 3 amino acid sequences of SEQ ID NOs: 90, 91, and 92 (H chain CDRs of Q354), respectively;
(a7) an antigen-binding site comprising the H chain CDR 1, 2, and 3 amino acid sequences of SEQ ID NOs: 93, 94, and 95 (H chain CDRs of Q360), respectively;
(a8) an antigen-binding site comprising the of H chain CDR 1, 2, and 3 amino acid sequences of SEQ ID NOs: 96, 97, and 98 (H chain CDRs of Q405), respectively;
(a9) an antigen-binding site comprising an H chain CDR 1, 2, and 3 amino acid sequences of SEQ ID NOs: 99, 100, and 101 (H chain CDRs of Q458), respectively;
(a10) an antigen-binding site comprising an H chain CDR 1, 2, and 3 amino acid sequences of SEQ ID NOs: 102, 103, and 104 (H chain CDRs of Q460), respectively;
(a11) an antigen-binding site comprising an H chain CDR 1, 2, and 3 amino acid sequences of SEQ ID NOs: 105, 106, and 107 (H chain CDRs of Q499), respectively;
(b1) an antigen-binding site comprising an H chain CDR 1, 2, and 3 amino acid sequences of SEQ ID NOs: 108, 109, and 110 (H chain CDRs of J232), respectively;
(b2) an antigen-binding site comprising an H chain CDR 1, 2, and 3 amino acid sequences of SEQ ID NOs: 111, 112, and 113 (H chain CDRs of J259), respectively;
(b3) an antigen-binding site comprising an H chain CDR 1, 2, and 3 amino acid sequences of SEQ ID NOs: 114, 115, and 116 (H chain CDRs of J268), respectively;
(b4) an antigen-binding site comprising an H chain CDR 1, 2, and 3 amino acid sequences of SEQ ID NOs: 117, 118, and 119 (H chain CDRs of J300), respectively;
(b5) an antigen-binding site comprising an H chain CDR 1, 2, and 3 amino acid sequences of SEQ ID NOs: 120, 121, and 122 (H chain CDRs of J321), respectively;
(b6) an antigen-binding site comprising the H chain CDR 1, 2, and 3 amino acid sequences of SEQ ID NOs: 123, 124, and 125 (H chain CDRs of J326), respectively;
(b7) an antigen-binding site comprising an H chain CDR 1, 2, and 3 amino acid sequences of SEQ ID NOs: 126, 127, and 128 (H chain CDRs of J327), respectively;
(b8) an antigen-binding site comprising an H chain CDR 1, 2, and 3 amino acid sequences of SEQ ID NOs: 129, 130, and 131 (H chain CDRs of J339), respectively;
(b9) an antigen-binding site comprising an H chain CDR 1, 2, and 3 amino acid sequences of SEQ ID NOs: 132, 133, and 134 (H chain CDRs of J344), respectively;
(b10) an antigen-binding site comprising an H chain CDR 1, 2, and 3 amino acid sequences of SEQ ID NOs: 135, 136, and 137 (H chain CDRs of J346), respectively; and
(b11) an antigen-binding site comprising an H chain CDR 1, 2, and 3 amino acid sequences of SEQ ID NOs: 174, 175, and 176 (H chain CDRs of J142), respectively.

Preferred embodiments of the antigen-binding site of the third and fourth polypeptides specifically include, for example, antigen-binding sites comprising the amino acid sequences of:
L2 L chain each CDR1, 2, and 3 sequence (SEQ ID NOs: 138, 139, and 140, respectively);
L45 L chain each CDR1, 2, and 3 sequence (SEQ ID NOs: 141, 142, and 143, respectively);
L248 L chain each CDR1, 2, and 3 sequence (SEQ ID NOs: 144, 145, and 146, respectively);
L324 L chain each CDR1, 2, and 3 sequence (SEQ ID NOs: 147, 148, and 149, respectively);
L334 L chain each CDR1, 2, and 3 sequence (SEQ ID NOs: 150, 151, and 152, respectively);
L377 L chain each CDR1, 2, and 3 sequence (SEQ ID NOs: 153, 154, and 155, respectively);
L404 L chain each CDR1, 2, and 3 sequence (SEQ ID NOs: 156, 157, and 158, respectively);
L406 L chain each CDR1, 2, and 3 sequence (SEQ ID NOs: 159, 160, and 161, respectively);
L408 L chain each CDR1, 2, and 3 sequence (SEQ ID NOs: 162, 163, and 164, respectively); and
L180 L chain each CDR1, 2, and 3 sequence (SEQ ID NOs: 177, 178, and 179, respectively) mentioned in the later-described Examples, or antigen-binding sites that are functionally equivalent to them.

More specifically, the present invention provides multispecific antigen-binding molecules, wherein the antigen-binding sites included in the third polypeptide and the fourth polypeptide comprise an antigen-binding site which comprises L chain CDRs consisting of any one of the amino acid sequences selected from the following (c1) to (c10), or an antigen-binding site functionally equivalent thereto:

(c1) an antigen-binding site comprising an L chain CDR1, 2, and 3 amino acid sequences of SEQ ID NOs: 138, 139, and 140 (L chain CDR of L2), respectively;
(c2) an antigen-binding site comprising an L chain CDR1, 2, and 3 amino acid sequences of SEQ ID NOs: 141, 142, and 143 (L chain CDR of L45), respectively;

(c3) an antigen-binding site comprising an L chain CDR1, 2, and 3 amino acid sequences of SEQ ID NOs: 144, 145, and 146 (L chain CDR of L248), respectively;
(c4) an antigen-binding site comprising an L chain CDR1, 2, and 3 amino acid sequences of SEQ ID NOs: 147, 148, and 149 (L chain CDR of L324), respectively;
(c5) an antigen-binding site comprising an L chain CDR1, 2, and 3 amino acid sequences of SEQ ID NOs: 150, 151, and 152 (L chain CDR of L334), respectively;
(c6) an antigen-binding site comprising an L chain CDR1, 2, and 3 amino acid sequences of SEQ ID NOs: 153, 154, and 155 (L chain CDR of L377), respectively;
(c7) an antigen-binding site comprising an L chain CDR1, 2, and 3 amino acid sequences of SEQ ID NOs: 156, 157, and 158 (L chain CDR of L404), respectively;
(c8) an antigen-binding site comprising an L chain CDR1, 2, and 3 amino acid sequences of SEQ ID NOs: 159, 160, and 161 (L chain CDR of L406), respectively;
(c9) an antigen-binding site comprising an L chain CDR1, 2, and 3 amino acid sequences of SEQ ID NOs: 137, 138, and 139 (L chain CDR of L408), respectively; and
(c10) an antigen-binding site comprising an L chain CDR1, 2, and 3 amino acid sequences of SEQ ID NOs: 177, 178, and 179 (L chain CDR of L180), respectively.

The amino acid sequences of the H chain variable regions of Q1, Q31, Q64, Q85, Q153, Q354, Q360, Q405, Q458, Q460, and Q499 of the present invention are indicated by the following SEQ ID NOs, respectively.

Q1: SEQ ID NO: 35
Q31: SEQ ID NO: 36
Q64: SEQ ID NO: 37
Q85: SEQ ID NO: 38
Q153: SEQ ID NO: 39
Q354: SEQ ID NO: 40
Q360: SEQ ID NO: 41
Q405: SEQ ID NO: 42
Q458: SEQ ID NO: 43
Q460: SEQ ID NO: 44
Q499: SEQ ID NO: 45

The amino acid sequences of the H chain variable regions of J232, J259, J268, J300, J321, J326, J327, J339, J344, J346, and J142 of the present invention are indicated by the following SEQ ID NOs, respectively.

J232: SEQ ID NO: 46
J259: SEQ ID NO: 47
J268: SEQ ID NO: 48
J300: SEQ ID NO: 49
J321: SEQ ID NO: 50
J326: SEQ ID NO: 51
J327: SEQ ID NO: 52
J339: SEQ ID NO: 53
J344: SEQ ID NO: 54
J346: SEQ ID NO: 55
J142: SEQ ID NO: 172

More specifically, the present invention provides multispecific antigen-binding molecules, wherein the antigen-binding site of the first polypeptide comprises an antigen-binding site which comprises an H chain variable region consisting of any one of the amino acid sequences selected from the following (a1) to (a11), or an antigen-binding site functionally equivalent thereto, and the antigen-binding site of the second polypeptide comprises an antigen-binding site which comprises an H chain variable region consisting of any one of the amino acid sequences selected from the following (b1) to (b11), or an antigen-binding site functionally equivalent thereto:

(a1) an antigen-binding site comprising an H chain variable region amino acid sequence of SEQ ID NO: 35 (H chain variable region of Q1);
(a2) an antigen-binding site comprising an H chain variable region amino acid sequence of SEQ ID NO: 36 (H chain variable region of Q31);
(a3) an antigen-binding site comprising an H chain variable region amino acid sequence of SEQ ID NO: 37 (H chain variable region of Q64);
(a4) an antigen-binding site comprising an H chain variable region amino acid sequence of SEQ ID NO: 38 (H chain variable region of Q85);
(a5) an antigen-binding site comprising an H chain variable region amino acid sequence of SEQ ID NO: 39 (H chain variable region of Q153);
(a6) an antigen-binding site comprising an H chain variable region amino acid sequence of SEQ ID NO: 40 (H chain variable region of Q354);
(a7) an antigen-binding site comprising an H chain variable region amino acid sequence of SEQ ID NO: 41 (H chain variable region of Q360);
(a8) an antigen-binding site comprising an H chain variable region amino acid sequence of SEQ ID NO: 42 (H chain variable region of Q405);
(a9) an antigen-binding site comprising an H chain variable region amino acid sequence of SEQ ID NO: 43 (H chain variable region of Q458);
(a10) an antigen-binding site comprising an H chain variable region amino acid sequence of SEQ ID NO: 44 (H chain variable region of Q460);
(a11) an antigen-binding site comprising an H chain variable region amino acid sequence of SEQ ID NO: 45 (H chain variable region of Q499);
(b1) an antigen-binding site comprising an H chain variable region amino acid sequence of SEQ ID NO: 46 (H chain variable region of J232);
(b2) an antigen-binding site comprising an H chain variable region amino acid sequence of SEQ ID NO: 47 (H chain variable region of J259);
(b3) an antigen-binding site comprising an H chain variable region amino acid sequence of SEQ ID NO: 48 (H chain variable region of J268);
(b4) an antigen-binding site comprising an H chain variable region amino acid sequence of SEQ ID NO: 49 (H chain variable region of J300);
(b5) an antigen-binding site comprising an H chain variable region amino acid sequence of SEQ ID NO: 50 (H chain variable region of J321);
(b6) an antigen-binding site comprising an H chain variable region amino acid sequence of SEQ ID NO: 51 (H chain variable region of J326);
(b7) an antigen-binding site comprising an H chain variable region amino acid sequence of SEQ ID NO: 52 (H chain variable region of J327);
(b8) an antigen-binding site comprising an H chain variable region amino acid sequence of SEQ ID NO: 53 (H chain variable region of J339);
(b9) an antigen-binding site comprising an H chain variable region amino acid sequence of SEQ ID NO: 54 (H chain variable region of J344);
(b10) an antigen-binding site comprising an H chain variable region amino acid sequence of SEQ ID NO: 55 (H chain variable region of J346); and
(b11) an antigen-binding site comprising an H chain variable region amino acid sequence of SEQ ID NO: 172 (H chain variable region of J142).

In addition, the amino acid sequences of the L chain variable regions of L2, L45, L248, L324, L334, L377, L404, L406, L408, and L180 of the present invention are indicated by the following SEQ ID NOs, respectively.

L2: SEQ ID NO: 56
L45: SEQ ID NO: 57
L248: SEQ ID NO: 58
L324: SEQ ID NO: 59
L334: SEQ ID NO: 60
L377: SEQ ID NO: 61
L404: SEQ ID NO: 62
L406: SEQ ID NO: 63
L408: SEQ ID NO: 64
L180: SEQ ID NO: 173

More specifically, the present invention provides multispecific antigen-binding molecules, wherein the antigen-binding sites included in the third polypeptide and the fourth polypeptide comprise an antigen-binding site which comprises an L chain variable region consisting of any one of the amino acid sequences selected from the following (c1) to (c10), or an antigen-binding site functionally equivalent thereto:

(c1) an antigen-binding site comprising an L chain variable region amino acid sequence of SEQ ID NO: 56 (L chain variable region of L2);
(c2) an antigen-binding site comprising an L chain variable region amino acid sequence of SEQ ID NO: 57 (L chain variable region of L45);
(c3) an antigen-binding site comprising an L chain variable region amino acid sequence of SEQ ID NO: 58 (L chain variable region of L248);
(c4) an antigen-binding site comprising an L chain variable region amino acid sequence of SEQ ID NO: 59 (L chain variable region of L324);
(c5) an antigen-binding site comprising an L chain variable region amino acid sequence of SEQ ID NO: 60 (L chain variable region of L334);
(c6) an antigen-binding site comprising an L chain variable region amino acid sequence of SEQ ID NO: 61 (L chain variable region of L377);
(c7) an antigen-binding site comprising an L chain variable region amino acid sequence of SEQ ID NO: 62 (L chain variable region of L404);
(c8) an antigen-binding site comprising an L chain variable region amino acid sequence of SEQ ID NO: 63 (L chain variable region of L406);
(c9) an antigen-binding site comprising an L chain variable region amino acid sequence of SEQ ID NO: 64 (L chain variable region of L408); and
(c10) an antigen-binding site comprising an L chain variable region amino acid sequence of SEQ ID NO: 173 (L chain variable region of L180).

The amino acid sequences of CDR1 to 3 and FR1 to 4 in each of the sequences are as described in FIGS. 3A to D When producing a full-length antibody using the variable regions disclosed in the present invention, without particular limitations, constant regions well known to those skilled in the art may be used. For example, constant regions described in "Sequences of proteins of immunological interest", (1991), U.S. Department of Health and Human Services. Public Health Service National Institutes of Health, or "An efficient route to human bispecific IgG", (1998). Nature Biotechnology vol. 16, 677-681 can be used. Preferred examples of the antibody constant regions of the present invention include the constant regions of IgG antibodies. When using the constant region of an IgG antibody, its type is not limited, and a constant region of IgG subclass such as IgG1, IgG2, IgG3, or IgG4 may be used. Furthermore, amino acid mutations may be introduced into the constant region of these IgG subclasses. Amino acid mutations to be introduced may be, for example, those that enhance or decrease binding to Fcγ receptors (Proc Natl Acad Sci USA. 2006 Mar. 14; 103(11): 4005-10; and MAbs. 2009 November; 1(6): 572-9), or enhance or decrease binding to FcRn (J Biol. Chem. 2001 Mar. 2; 276(9): 6591-604; Int Immunol. 2006 December; 18(12): 1759-69; and J Biol Chem. 2006 Aug. 18; 281(33): 23514-24), but are not limited thereto. Two types of H chains must be heterologously associated to produce a bispecific antibody. The knobs-into-holes technology (J Immunol Methods. 2001 Feb. 1; 248(1-2): 7-15; and J Biol Chem. 2010 Jul. 2; 285(27): 20850-9), the electrostatic repulsion technology (WO 2006/106905), the SEEDbody technology (Protein Eng Des Sel. 2010 April; 23(4): 195-202), and such may be used for heterologous association of two types of H chains via a CH3 domain. Furthermore, the antibodies of the present invention may be those with a modified or deficient sugar chain. Examples of antibodies having modified sugar chains include glycosylation-engineered antibodies (such as WO 99/54342), antibodies with defucosylated sugar chains (WO 00/61739, WO 02/31140, WO 2006/067847, WO 2006/067913, etc.), and antibodies having a sugar chain with bisecting GlcNAc (such as WO 02/79255). Known examples of methods for producing sugar chain-deficient IgG antibodies include the method of introducing a mutation to asparagine at position 297 in the EU numbering (J Clin Pharmacol. 2010 May; 50(5): 494-506), and the method of producing IgG using *Escherichia coli* (J Immunol Methods. 2002 May 1; 263(1-2): 133-47; and J Biol. Chem. 2010 Jul. 2; 285(27): 20850-9). Furthermore, heterogeneity accompanying deletion of C-terminal lysine in IgG, and heterogeneity accompanying mispairing of disulfide bonds in the hinge region of IgG2 can be decreased by introducing amino acid deletions/substitutions (WO 2009/041613).

The present invention provides, for example, multispecific antigen-binding molecules, wherein the first and second polypeptides comprise an antibody H chain constant region, and the third and fourth polypeptides comprise an antibody L chain constant region.

Furthermore, the present invention provides multispecific antigen-binding molecules, wherein the first polypeptide comprises an antibody H chain constant region consisting of any one of the amino acid sequences selected from the group consisting of the following (d1) to (d6) or the group consisting of the following (d7) to (d9), and the second polypeptide comprises an antibody H chain constant region consisting of any one of the amino acid sequences selected from a group different from that of the above-mentioned first polypeptide:

(d1) an H chain constant region of SEQ ID NO: 65 (G4k);
(d2) an H chain constant region of SEQ ID NO: 66 (z7);
(d3) an H chain constant region of SEQ ID NO: 67 (z55);
(d4) an H chain constant region of SEQ ID NO: 68 (z106);
(d5) an H chain constant region of SEQ ID NO: 69 (z118);
(d6) an H chain constant region of SEQ ID NO: 70 (z121);
(d7) an H chain constant region of SEQ ID NO: 71 (G4h);
(d8) an H chain constant region of SEQ ID NO: 72 (z107); and
(d9) an H chain constant region of SEQ ID NO: 73 (z119).

Furthermore, the present invention provides a multispecific antigen-binding molecule, wherein the third and fourth polypeptides comprise an antibody L chain constant region consisting of the following amino acid sequence of:

(e) an L chain constant region of SEQ ID NO: 74 (k).

In the present invention, the phrase "functionally substitute for F.VIII" means that F.IX and/or F.IXa, and F.X is recognized, and activation of F.X is promoted (F.Xa generation is promoted).

In the present invention, "F.Xa generation-promoting activity" can be confirmed by evaluating the multispecific antigen-binding molecules of the present invention using, for example, a measurement system comprising F.XIa (F.IX activating enzyme), F.IX, F.X, F synthetic substrate S-2222 (synthetic substrate of F.Xa), and phospholipids. This measurement system shows the correlation between the severity of the disease and clinical symptoms in hemophilia A cases (Rosen S, Andersson M, Blomback M et al. Clinical applications of a chromogenic substrate method for determination of FVIII activity. Thromb Haemost 1985, 54: 811-23). That is, in the present measurement system, test substances that show higher F.Xa generation-promoting activity are expected to show better hemostatic effects against bleeding episodes in hemophilia A. With these results, if a multispecific antigen-binding molecule having activity of functionally substituting for F.VIII is a molecule having a higher activity than hA69-KQ/hB26-PF/hAL-AQ, it may yield excellent blood coagulation-promoting activity, and excellent effects may be obtained as a pharmaceutical component for preventing and/or treating bleeding, a disease accompanying bleeding, or a disease caused by bleeding. To obtain excellent effects as the above-mentioned pharmaceutical component, for example, F.Xa generation-promoting activity measured under the conditions described in [Example 2] is preferably not less than that of hA69-KQ/hB26-PF/hAL-AQ, and in particular, the activity is more preferably the same as or not less than that of Q153-G4k/J142-G4h/L180-k. Herein, the "F.Xa generation-promoting activity" is the value obtained by subtracting the change in absorbance upon 20 minutes in a solvent from the change in absorbance upon 20 minutes in an antibody solution.

A preferred embodiment of the present invention is a multispecific antibody that functionally substitutes for F.VIII, which recognizes F.IX and/or F.IXa, and F.X.

The above-mentioned multispecific antibodies of the present invention are preferably antibodies which comprise H chain CDRs of anti-F.IX/F.IXa antibodies or CDRs functionally equivalent to them, and H chain CDRs of anti-F.X antibodies or CDRs functionally equivalent to them.

Furthermore, the antibodies of the present invention are preferably antibodies comprising an antigen-binding site having:
H chain CDR 1, 2, and 3 amino acid sequences of SEQ ID NOs 75, 76, and 77 (H chain CDRs of Q1), respectively;
H chain CDR 1, 2, and 3 amino acid sequences of SEQ ID NOs 78, 79, and 80 (H chain CDRs of Q31), respectively;
H chain CDR 1, 2, and 3 amino acid sequences of SEQ ID NOs 81, 82, and 83 (H chain CDRs of Q64), respectively;
H chain CDR 1, 2, and 3 amino acid sequences of SEQ ID NOs 84, 85, and 86 (H chain CDRs of Q85), respectively;
H chain CDR 1, 2, and 3 amino acid sequences of SEQ ID NOs 87, 88, and 89 (H chain CDRs of Q153), respectively;
H chain CDR 1, 2, and 3 amino acid sequences of SEQ ID NOs 90, 91, and 92 (H chain CDRs of Q354), respectively;
H chain CDR 1, 2, and 3 amino acid sequences of SEQ ID NOs 93, 94, and 95 (H chain CDRs of Q360), respectively;
H chain CDR 1, 2, and 3 amino acid sequences of SEQ ID NOs 96, 97, and 98 (H chain CDRs of Q405), respectively;
H chain CDR 1, 2, and 3 amino acid sequences of SEQ ID NOs 99, 100, and 101 (H chain CDRs of Q458), respectively;
H chain CDR 1, 2, and 3 amino acid sequences of SEQ ID NOs 102, 103, and 104 (H chain CDRs of Q460), respectively; or
H chain CDR 1, 2, and 3 amino acid sequences of SEQ ID NOs 105, 106, and 107 (H chain CDRs of Q499), respectively,
in an anti-F.IX/IXa antibody, or an antigen-binding site functionally equivalent to it, and an antigen-binding site comprising:
H chain CDR 1, 2, and 3 amino acid sequences of SEQ ID NOs 108, 109, and 110 (H chain CDRs of J232), respectively;
H chain CDR 1, 2, and 3 amino acid sequences of SEQ ID NOs 111, 112, and 113 (H chain CDRs of J259), respectively;
H chain CDR 1, 2, and 3 amino acid sequences of SEQ ID NOs 114, 115, and 116 (H chain CDRs of J268), respectively;
H chain CDR 1, 2, and 3 amino acid sequences of SEQ ID NOs 117, 118, and 119 (H chain CDRs of J300), respectively;
H chain CDR 1, 2, and 3 amino acid sequences of SEQ ID NOs 120, 121, and 122 (H chain CDRs of J321), respectively;
H chain CDR 1, 2, and 3 amino acid sequences of SEQ ID NOs 123, 124, and 125 (H chain CDRs of J326), respectively;
H chain CDR 1, 2, and 3 amino acid sequences of SEQ ID NOs 126, 127, and 128 (H chain CDRs of J327), respectively;
H chain CDR 1, 2, and 3 amino acid sequences of SEQ ID NOs 129, 130, and 131 (H chain CDRs of J339), respectively;
H chain CDR 1, 2, and 3 amino acid sequences of SEQ ID NOs 132, 133, and 134 (H chain CDRs of J334), respectively;
the amino acid sequences of H chain CDR 1, 2, and 3 amino acid sequences of SEQ ID NOs 135, 136, and 137 (H chain CDRs of J346), respectively; or
H chain CDR 1, 2, and 3 amino acid sequences of SEQ ID NOs 174, 175, and 176 (H chain CDRs of J142), respectively,
in an anti-F.X antibody, or an antigen-binding site functionally equivalent to it.

In the present invention, "antigen-binding sites are functionally equivalent" means that the activities of functionally substituting for F.VIII possessed by the multispecific antigen-binding molecules having the antigen-binding sites are equivalent.

In the present invention, the term "equivalent" does not necessarily have to mean the same degree of activity, and the activity may be enhanced, or the activity may be decreased as long as there is an activity higher than that of hA69-KQ/hB26-PF/hAL-AQ according to the measurement system described above, or preferably F.Xa generation-promoting activity measured under the conditions described in [Example 2] is equivalent to or not less than that of Q153-G4k/J142-G4h/L180-k.

The above-mentioned antibodies may have one or more amino acid substitutions, deletions, additions, and/or insertions in the variable region (CDR sequences and/or FR sequences) of the amino acid sequence as long as they have an activity higher than that of hA69-KQ/hB26-PF/hAL-AQ according to the measurement system described above at page 35, lines 11-30, or preferably F.Xa generation-promoting activity measured under the conditions described in [Example 2] is equivalent to or not less than that of Q153-G4k/J142-G4h/L180-k. A method of introducing mutations into proteins is well known to those skilled in the art as a method for introducing one or more amino acid substitutions, deletions, additions, and/or insertions into an amino acid sequence. For example, those skilled in the art can prepare a desired mutant functionally equivalent to a multispecific polypeptide multimer having the activity of functionally substituting for F.VIII by introducing appropriate mutations into the amino acid sequence using site-directed mutagenesis (Hashimoto-Gotoh, T, Mizuno, T, Ogasahara, Y, and Nakagawa, M. (1995) An oligodeoxyribonucleotide-directed dual amber method for site-directed mutagenesis. Gene 152: 271-275; Zoller, M J, and Smith, M. (1983) Oligonucleotide-directed mutagenesis of DNA fragments cloned into M13 vectors. Methods Enzymol. 100: 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154: 350-367; and Kunkel, T A (1985) Rapid and efficient site-specific mutagenesis without phenotypic selection. Proc Natl Acad Sci USA. 82: 488-492) and such.

As such, antibodies of the present invention also include antibodies with one or more amino acid mutations in the variable region, and having an activity higher than that of hA69-KQ/hB26-PF/hAL-AQ according to the measurement system described above at page 35, lines 11-30, or preferably F.Xa generation-promoting activity measured under the conditions described in [Example 2] is equivalent to or not less than that of Q153-G4k/J142-G4h/L180-k.

When an amino acid residue is altered, the amino acid is preferably mutated for a different amino acid(s) that conserves the properties of the amino acid side-chain. Examples of amino acid side chain properties are: hydrophobic amino acids (A, I, L, M, F, P, W, Y, and V), hydrophilic amino acids (R, D, N, C, E, Q, G, H, K, S, and T), amino acids containing aliphatic side chains (G, A, V, L, I, and P), amino acids containing hydroxyl group-containing side chains (S, T, and Y), amino acids containing sulfur-containing side chains (C and M), amino acids containing carboxylic acid- and amide-containing side chains (D, N, E, and Q), amino acids containing basic side chains (R, K, and H), and amino acids containing aromatic side chains (H, F, Y, and W) (amino acids are represented by one-letter codes in parentheses) Amino acid substitutions within each group are called conservative substitutions. It is already known that a polypeptide containing a modified amino acid sequence in which one or more amino acid residues in a given amino acid sequence are deleted, added, and/or substituted with other amino acids can retain the original biological activity (Mark, D. F. et al., Proc. Natl. Acad. Sci. USA; (1984) 81: 5662-6; Zoller, M. J. and Smith, M., Nucleic Acids Res. (1982) 10: 6487-500; Wang, A. et al., Science (1984) 224: 1431-3; Dalbadie-McFarland, G. et al., Proc. Natl. Acad. Sci. USA (1982) 79: 6409-13). Such mutants have an amino acid identity of at least 70%, more preferably at least 75%, even more preferably at least 80%, still more preferably at least 85%, yet more preferably at least 90%, and most preferably at least 95%, with the variable regions (for example, CDR sequences, FR sequences, or whole variable regions) of the present invention. Herein, sequence identity is defined as the percentage of residues identical to those in the original amino acid sequence of the heavy chain variable region or light chain variable region, determined after the sequences are aligned and gaps are appropriately introduced to maximize the sequence identity as necessary. The identity of amino acid sequences can be determined by the method described below.

Alternatively, the amino acid sequences of variable regions that have a substitution, deletion, addition, and/or insertion of one or more amino acids in the amino acid sequence of the variable regions (CDR sequences and/or FR sequences) and have an activity higher than that of hA69-KQ/hB26-PF/hAL-AQ according to the measurement system described above at page 35, lines 11-30, or preferably F.Xa generation-promoting activity measured under the conditions described in [Example 2] is equivalent to or not less than that of Q153-G4k/J142-G4h/L180-k can be obtained from nucleic acids that hybridize under stringent conditions to nucleic acid composed of the nucleotide sequence encoding the amino acid sequence of the variable regions. Stringent hybridization conditions to isolate a nucleic acid that hybridizes under stringent conditions to a nucleic acid that includes the nucleotide sequence encoding the amino acid sequence of the variable regions include, for example, the conditions of 6 M urea, 0.4% SDS, 0.5×SSC, and 37° C., or hybridization conditions with stringencies equivalent thereto. With more stringent conditions, for example, the conditions of 6 M urea, 0.4% SDS, 0.1×SSC, and 42° C., isolation of nucleic acids with a much higher homology can be expected. The sequences of the isolated nucleic acids can be determined by the known methods described below. The overall nucleotide sequence homology of the isolated nucleic acid is at least 50% or higher sequence identity, preferably 70% or higher, more preferably 90% or higher (for example, 95%, 96%, 97%, 98%, 99%, or higher).

Nucleic acids that hybridize under stringent conditions to a nucleic acid composed of the nucleotide sequence encoding the amino acid sequence of the variable regions can also be isolated using, instead of the above-described methods using hybridization techniques, gene amplification methods such as polymerase chain reaction (PCR) using primers synthesized based on the information of nucleotide sequence encoding the amino acid sequence of the variable regions.

The identity of one nucleotide sequence or amino acid sequence to another can be determined using the algorithm BLAST, by Karlin and Altschul (Proc. Natl. Acad. Sci. USA (1993) 90: 5873-7). Programs such as BLASTN and BLASTX were developed based on this algorithm (Altschul et al., J. Mol. Biol. (1990) 215: 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov).

The present invention also provides antibodies that bind to an epitope overlapping with an epitope bound by the antibodies described above.

Whether an antibody recognizes an epitope overlapping with an epitope that is recognized by another antibody can be confirmed by the competition between the two antibodies against the epitope. Competition between the antibodies can be evaluated by competitive binding assays using means such as enzyme-linked immunosorbent assay (ELISA), fluorescence energy transfer method (FRET), and fluorometric microvolume assay technology (FMAT (Registered trademark)). The amount of antibodies bound to an antigen indirectly correlate with the binding ability of candidate competitor antibodies (test antibodies) that competitively bind to the overlapping epitope. In other words, as the amount of or the affinity of test antibodies against the overlapping epitope increases, the amount of antibodies bound to the antigen decreases, and the amount of test antibodies bound to the antigen increases. Specifically, appropriately labeled antibodies and antibodies to be evaluated are simultaneously added to the antigens, and the thus bound antibodies are detected using the label. The amount of antibodies bound to the antigen can be easily determined by labeling the antibodies beforehand. This label is not particularly limited, and the labeling method is selected according to the assay technique used. The labeling method includes fluorescent labeling, radiolabeling, enzymatic labeling, and such.

For example, fluorescently labeled antibodies and unlabeled antibodies or test antibodies are simultaneously added to beads immobilized with F.IX, F.IXa or F.X, and the labeled antibodies are detected by fluorometric microvolume assay technology.

Herein, the "antibody that binds to the overlapping epitope" refers to an antibody that can reduce the binding of the labeled antibody by at least 50% at a concentration that is usually 100 times higher, preferably 80 times higher, more preferably 50 times higher, even more preferably 30 times higher, and still more preferably 10 times higher than a concentration at which the non-labeled antibody reduces the binding of the labeled antibody by 50% ($IC_{50}$).

Multispecific antigen-binding molecules, which have antigen-binding sites of antibodies that bind to epitopes overlapping with epitopes bound by the above-mentioned antibodies, may yield an excellent activity of functionally substituting for F.VIII. Furthermore, in antigen-binding sites of antibodies that bind to epitopes overlapping with epitopes bound by the above-mentioned antibodies, one or more amino acids may be altered to obtain a better activity of functionally substituting for F.VIII. Multispecific antigen-binding molecules having a better activity of functionally substituting for F.VIII can be obtained by altering the amino acids of the antigen-binding sites and selecting multispecific antigen-binding molecules having an activity higher than that of hA69-KQ/hB26-PF/hAL-AQ according to the measurement system described above, or preferably having an F.Xa generation-promoting activity measured under the conditions described in [Example 2] that is equivalent to or not less than that of Q153-G4k/J142-G4h/L180-k. To obtain an excellent activity of functionally substituting for F.VIII of the present invention, the following amino acid alterations are particularly preferred.

(1) At least one amino acid residue selected from the amino acid residues at positions 34, 35, 49, 61, 62, 96, 98, 100, 100b, and 102 by Kabat numbering in the H chain of the antibody that recognizes F.IX and/or F.IXa is substituted with a different amino acid.

(2) At least one amino acid residue selected from the amino acid residues at positions 35, 53, 73, 76, 96, 98, 100, and 100a by Kabat numbering in the H chain of the antibody that recognizes F.X is substituted with a different amino acid.

(3) At least one amino acid residue selected from the amino acid residues at positions 27, 30, 31, 32, 50, 52, 53, 54, 55, 92, 93, 94, and 95 by Kabat numbering in the antibody L chain is substituted with a different amino acid.

Furthermore, in the present invention, preferred antibody amino acids for obtaining a better activity of functionally substituting for F.VIII include those mentioned in (4) to (6) below. Regarding these amino acids, the antibody H chain may originally have such amino acids, or antibody H chain amino acids may be modified to have such a sequence.

(4) An antibody H chain which recognizes F.IX and/or F.IXa, wherein, by Kabat numbering, the amino acid residue at position 34 is isoleucine, the amino acid residue at position 35 is asparagine, glutamine, or serine, the amino acid residue at position 49 is serine, the amino acid residue at position 61 is arginine, the amino acid residue at position 62 is glutamic acid, the amino acid residue at position 96 is serine or threonine, the amino acid residue at position 98 is lysine or arginine, the amino acid residue at position 100 is phenylalanine or tyrosine, the amino acid residue at position 100b is glycine, or the amino acid residue at position 102 is tyrosine.

(5) An antibody H chain which recognizes F.X, wherein, by Kabat numbering, the amino acid residue at position 35 is aspartic acid, the amino acid residue at position 53 is arginine, the amino acid residue at position 73 is lysine, the amino acid residue at position 76 is glycine, the amino acid residue at position 96 is lysine or arginine, the amino acid residue at position 98 is tyrosine, the amino acid residue at position 100 is tyrosine, or the amino acid residue at position 100a is histidine.

(6) An antibody L chain, wherein, by Kabat numbering, the amino acid residue at position 27 is lysine or arginine, the amino acid residue at position 30 is glutamic acid, the amino acid residue at position 31 is arginine, the amino acid residue at position 32 is glutamine, the amino acid residue at position 50 is arginine or glutamine, the amino acid residue at position 52 is serine, the amino acid residue at position 53 is arginine, the amino acid residue at position 54 is lysine, the amino acid residue at position 55 is glutamic acid, the amino acid residue at position 92 is serine, the amino acid residue at position 93 is serine, the amino acid residue at position 94 is proline, or the amino acid residue at position 95 is proline.

Among the above-mentioned antibody amino acid residues of (1) to (6), favorable positions of amino acid residues for obtaining a particularly excellent F.VIII-like activity are shown in the following (1) to (3).

(1) Amino acid residues at positions 34, 35, 61, 98, 100, and 100b, particularly amino acid residues at positions 61 and 100, by Kabat numbering in the H chain of the antibody that recognizes F.IX and/or F.IXa.

(2) Amino acid residues at positions 35, 53, 73, 96, 98, 100, and 100a by Kabat numbering in the H chain of the antibody that recognizes F.X.

(3) Amino acid residues at positions 27, 30, 31, 32, 50, 52, 53, 93, 94, and 95, and particularly amino acid residues at positions 27, 30, 31, 50, 53, 94, and 95, by Kabat numbering in the antibody L chain.

Specifically, the present invention provides multispecific antigen-binding molecules, wherein a first polypeptide comprises any of the antibody H chains selected from the following (a1) to (a14) and any of the antibody L chains selected from the following (c1) to (c10), and the second polypeptide comprises any of the antibody H chains selected from the following (b1) to (b12) and any of the antibody L chains selected from the following (c1) to (c10):

(a1) an antibody H chain consisting of the amino acid sequence of SEQ ID NO: 1 (Q1-G4k);
(a2) an antibody H chain consisting of the amino acid sequence of SEQ ID NO: 2 (Q31-z7);
(a3) an antibody H chain consisting of the amino acid sequence of SEQ ID NO: 3 (Q64-z55);
(a4) an antibody H chain consisting of the amino acid sequence of SEQ ID NO: 10 (Q64-z7);
(a5) an antibody H chain consisting of the amino acid sequence of SEQ ID NO: 11 (Q85-G4k);
(a6) an antibody H chain consisting of the amino acid sequence of SEQ ID NO: 12 (Q153-G4k);
(a7) an antibody H chain consisting of the amino acid sequence of SEQ ID NO: 13 (Q354-z106);
(a8) an antibody H chain consisting of the amino acid sequence of SEQ ID NO: 14 (Q360-G4k);
(a9) an antibody H chain consisting of the amino acid sequence of SEQ ID NO: 15 (Q360-z118);
(a10) an antibody H chain consisting of the amino acid sequence of SEQ ID NO: 16 (Q405-G4k);

(a11) an antibody H chain consisting of the amino acid sequence of SEQ ID NO: 17 (Q458-z106);
(a12) an antibody H chain consisting of the amino acid sequence of SEQ ID NO: 18 (Q460-z121);
(a13) an antibody H chain consisting of the amino acid sequence of SEQ ID NO: 19 (Q499-z118);
(a14) an antibody H chain consisting of the amino acid sequence of SEQ ID NO: 20 (Q499-z121);
(b1) an antibody H chain consisting of the amino acid sequence of SEQ ID NO: 4 (J268-G4h);
(b2) an antibody H chain consisting of the amino acid sequence of SEQ ID NO: 5 (J321-G4h);
(b3) an antibody H chain consisting of the amino acid sequence of SEQ ID NO: 6 (J326-z107);
(b4) an antibody H chain consisting of the amino acid sequence of SEQ ID NO: 7 (J344-z107);
(b5) an antibody H chain consisting of the amino acid sequence of SEQ ID NO: 21 (J232-G4h);
(b6) an antibody H chain consisting of the amino acid sequence of SEQ ID NO: 22 (J259-z107);
(b7) an antibody H chain consisting of the amino acid sequence of SEQ ID NO: 23 (J300-z107);
(b8) an antibody H chain consisting of the amino acid sequence of SEQ ID NO: 24 (J327-z107);
(b9) an antibody H chain consisting of the amino acid sequence of SEQ ID NO: 25 (J327-z119);
(b10) an antibody H chain consisting of the amino acid sequence of SEQ ID NO: 26 (J339-z119);
(b11) an antibody H chain consisting of the amino acid sequence of SEQ ID NO: 27 (J346-z107);
(b12) an antibody H chain consisting of the amino acid sequence of SEQ ID NO: 170 (J142-G4h);
(c1) an antibody L chain consisting of the amino acid sequence of SEQ ID NO: 8 (L2-k);
(c2) an antibody L chain consisting of the amino acid sequence of SEQ ID NO: 9 (L45-k);
(c3) an antibody L chain consisting of the amino acid sequence of SEQ ID NO: 28 (L248-k);
(c4) an antibody L chain consisting of the amino acid sequence of SEQ ID NO: 29 (L324-k);
(c5) an antibody L chain consisting of the amino acid sequence of SEQ ID NO: 30 (L334-k);
(c6) an antibody L chain consisting of the amino acid sequence of SEQ ID NO: 31 (L377-k);
(c7) an antibody L chain consisting of the amino acid sequence of SEQ ID NO: 32 (L404-k);
(c8) an antibody L chain consisting of the amino acid sequence of SEQ ID NO: 33 (L406-k);
(c9) an antibody L chain consisting of the amino acid sequence of SEQ ID NO: 34 (L408-k); and
(c10) an antibody L chain consisting of the amino acid sequence of SEQ ID NO: 171 (L180-k).

The present invention also provides multispecific antigen-binding molecules, wherein the first polypeptide comprises an antigen-binding site which binds to an epitope overlapping with an epitope that binds to an antibody consisting of the antibody H chain of any one of (a1) to (a14) and the antibody L chain of any one of (c1) to (c10) described above, and the second polypeptide comprises an antigen-binding site which binds to an epitope overlapping with an epitope that binds to an antibody consisting of the antibody H chain of any one of (b1) to (b12) and the antibody L chain of any one of (c1) to (c10) described above.

Furthermore, the present invention provides multispecific antigen-binding molecules, wherein the first polypeptide comprises any one antibody H chain selected from the following (e1) to (e3), the second polypeptide comprises any one antibody H chain selected from the following (f1) to (f3), and the third polypeptide and the fourth polypeptide comprise any one antibody L chain selected from the following (g1) to (g4):

(e1) an H chain of an antibody which binds to an epitope overlapping with an epitope bound by an antibody consisting of an antibody H chain of any one of (a1) to (a14) and an antibody L chain of any one of (c1) to (c10) described above;
(e2) an antibody H chain, wherein at least one amino acid residue selected from the amino acid residues at positions 34, 35, 49, 61, 62, 96, 98, 100, 100b, and 102 by Kabat numbering in any one antibody H chain selected from (e1) described above is substituted with another amino acid;
(e3) an antibody H chain, wherein by Kabat numbering, the amino acid residue at position 34 is isoleucine, the amino acid residue at position 35 is asparagine, glutamine, or serine, the amino acid residue at position 49 is serine, the amino acid residue at position 61 is arginine, the amino acid residue at position 62 is glutamic acid, the amino acid residue at position 96 is serine or threonine, the amino acid residue at position 98 is lysine or arginine, the amino acid residue at position 100 is phenylalanine or tyrosine, the amino acid residue at position 100b is glycine, or the amino acid residue at position 102 is tyrosine in any antibody H chain selected from (e1) described above;
(f1) an H chain of an antibody which binds to an epitope overlapping with an epitope bound by an antibody consisting of an antibody H chain of any of (b1) to (b12) described above and an antibody L chain of any of (c1) to (c10) described above;
(f2) an antibody H chain, wherein at least one amino acid residue selected from the amino acid residues at positions 35, 53, 73, 76, 96, 98, 100, and 100a by Kabat numbering in any antibody H chain of (f1) described above is substituted with another amino acid;
(f3) an antibody H chain, wherein by Kabat numbering, the amino acid residue at position 35 is aspartic acid, the amino acid residue at position 53 is arginine, the amino acid residue at position 73 is lysine, the amino acid residue at position 76 is glycine, the amino acid residue at position 96 is lysine or arginine, the amino acid residue at position 98 is tyrosine, the amino acid residue at position 100 is tyrosine, or the amino acid residue at position 100a is histidine in any one antibody H chain selected from (f1) described above;
(g1) an L chain of an antibody which binds to an epitope overlapping with an epitope bound by an antibody which consists of an antibody H chain of any one of (a1) to (a14) and an antibody L chain of any one of (c1) to (c10) described above;
(g2) an L chain of an antibody which binds to an epitope overlapping with an epitope bound by an antibody which consists of an antibody H chain of any one of (b1) to (b12) and an antibody L chain of any one of (c1) to (c10) described above;
(g3) an antibody L chain, wherein at least one amino acid residue selected from the amino acid residues at positions 27, 30, 31, 32, 50, 52, 53, 54, 55, 92, 93, 94, and 95 by Kabat numbering in the antibody L chain of either (g1) or (g2) described above is substituted with another amino acid; and
(g4) an antibody L chain, wherein by Kabat numbering, the amino acid residue at position 27 is lysine or arginine, the amino acid residue at position 30 is glutamic acid, the amino acid residue at position 31 is arginine, the amino acid residue at position 32 is glutamine, the amino acid residue at position 50 is arginine or glutamine, the amino acid residue at position 52 is serine, the amino acid residue at position 53 is arginine, the amino acid residue at position 54 is lysine, the amino acid residue at position 55 is glutamic acid, the amino acid residue at position 92 is serine, the amino acid residue at position 93 is serine, the amino acid residue at position 94 is proline, or the amino acid residue at position 95 is proline in the antibody L chain of either (g1) or (g2) described above.

Amino acid substitutions can be performed on the antibodies (clones) of the present invention to avoid deamidation, methionine oxidation, and such, or to structurally stabilize the antibodies.

The method for obtaining multispecific antigen-binding molecules of the present invention is not particularly limited, and may be any method. Bispecific antibodies can be generated according to the methods described in WO 2006/109592, WO 2005/035756, WO 2006/106905, or WO 2007/114325, which are known as examples of the method for producing the bispecific antibodies; and then desired antibodies having a cofactor function-substituting activity can be selected and obtained.

For example, the bispecific antibody described in any of the following (a) to (u) is provided by the present invention:

(a) a bispecific antibody (Q1-G4k/J268-G4h/L45-k), wherein the first polypeptide is an H chain consisting of the amino acid sequence of SEQ ID NO: 1, the second polypeptide is an H chain consisting of the amino acid sequence of SEQ ID NO: 4, and the third polypeptide and the fourth polypeptide are a commonly shared L chain of SEQ ID NO: 9;

(b) a bispecific antibody (Q1-G4k/J321-G4h/L45-k), wherein the first polypeptide is an H chain consisting of the amino acid sequence of SEQ ID NO: 1, the second polypeptide is an H chain consisting of the amino acid sequence of SEQ ID NO: 5, and the third polypeptide and the fourth polypeptide are a commonly shared L chain of SEQ ID NO: 9;

(c) a bispecific antibody (Q31-z7/J326-z107/L2-k), wherein the first polypeptide is an H chain consisting of the amino acid sequence of SEQ ID NO: 2, the second polypeptide is an H chain consisting of the amino acid sequence of SEQ ID NO: 6, and the third polypeptide and the fourth polypeptide are a commonly shared L chain of SEQ ID NO: 8;

(d) a bispecific antibody (Q64-z55/J344-z107/L45-k), wherein the first polypeptide is an H chain consisting of the amino acid sequence of SEQ ID NO: 3, the second polypeptide is an H chain consisting of the amino acid sequence of SEQ ID NO: 7, and the third polypeptide and the fourth polypeptide are a commonly shared L chain of SEQ ID NO: 9;

(e) a bispecific antibody (Q64-z7/J326-z107/L334-k), wherein the first polypeptide is an H chain consisting of the amino acid sequence of SEQ ID NO: 10, the second polypeptide is an H chain consisting of the amino acid sequence of SEQ ID NO: 6, and the third polypeptide and the fourth polypeptide are a commonly shared L chain of SEQ ID NO: 30;

(f) a bispecific antibody (Q64-z7/J344-z107/L406-k), wherein the first polypeptide is an H chain consisting of the amino acid sequence of SEQ ID NO: 10, the second polypeptide is an H chain consisting of the amino acid sequence of SEQ ID NO: 7, and the third polypeptide and the fourth polypeptide are a commonly shared L chain of SEQ ID NO: 33;

(g) a bispecific antibody (Q85-G4k/J268-G4h/L406-k), wherein the first polypeptide is an H chain consisting of the amino acid sequence of SEQ ID NO: 11, the second polypeptide is an H chain consisting of the amino acid sequence of SEQ ID NO: 4, and the third polypeptide and the fourth polypeptide are a commonly shared L chain of SEQ ID NO: 33;

(h) a bispecific antibody (Q85-G4k/J321-G4h/L334-k), wherein the first polypeptide is an H chain consisting of the amino acid sequence of SEQ ID NO: 11, the second polypeptide is an H chain consisting of the amino acid sequence of SEQ ID NO: 5, and the third polypeptide and the fourth polypeptide are a commonly shared L chain of SEQ ID NO: 30;

(i) a bispecific antibody (Q153-G4k/J232-G4h/L406-k), wherein the first polypeptide is an H chain consisting of the amino acid sequence of SEQ ID NO: 12, the second polypeptide is an H chain consisting of the amino acid sequence of SEQ ID NO: 21, and the third polypeptide and the fourth polypeptide are a commonly shared L chain of SEQ ID NO: 33;

(j) a bispecific antibody (Q354-z106/J259-z107/L324-k), wherein the first polypeptide is an H chain consisting of the amino acid sequence of SEQ ID NO: 13, the second polypeptide is an H chain consisting of the amino acid sequence of SEQ ID NO: 22, and the third polypeptide and the fourth polypeptide are a commonly shared L chain of SEQ ID NO: 29;

(k) a bispecific antibody (Q360-G4k/J232-G4h/L406-k), wherein the first polypeptide is an H chain consisting of the amino acid sequence of SEQ ID NO: 14, the second polypeptide is an H chain consisting of the amino acid sequence of SEQ ID NO: 21, and the third polypeptide and the fourth polypeptide are a commonly shared L chain of SEQ ID NO: 33;

(l) a bispecific antibody (Q360-z118/J300-z107/L334-k), wherein the first polypeptide is an H chain consisting of the amino acid sequence of SEQ ID NO: 15, the second polypeptide is an H chain consisting of the amino acid sequence of SEQ ID NO: 23, and the third polypeptide and the fourth polypeptide are a commonly shared L chain of SEQ ID NO: 30;

(m) a bispecific antibody (Q405-G4k/J232-G4h/L248-k), wherein the first polypeptide is an H chain consisting of the amino acid sequence of SEQ ID NO: 16, the second polypeptide is an H chain consisting of the amino acid sequence of SEQ ID NO: 21, and the third polypeptide and the fourth polypeptide are a commonly shared L chain of SEQ ID NO: 28;

(n) a bispecific antibody (Q458-z106/J346-z107/L408-k), wherein the first polypeptide is an H chain consisting of the amino acid sequence of SEQ ID NO: 17, the second polypeptide is an H chain consisting of the amino acid sequence of SEQ ID NO: 27, and the third polypeptide and the fourth polypeptide are a commonly shared L chain of SEQ ID NO: 34;

(o) a bispecific antibody (Q460-z121/J327-z119/L334-k), wherein the first polypeptide is an H chain consisting of the amino acid sequence of SEQ ID NO: 18, the second polypeptide is an H chain consisting of the amino acid sequence of SEQ ID NO: 25, and the third polypeptide and the fourth polypeptide are a commonly shared L chain of SEQ ID NO: 30;

(p) a bispecific antibody (Q499-z118/J327-z107/L334-k), wherein the first polypeptide is an H chain consisting of the amino acid sequence of SEQ ID NO: 19, the second polypeptide is an H chain consisting of the amino acid sequence of SEQ ID NO: 24, and the third polypeptide and the fourth polypeptide are a commonly shared L chain of SEQ ID NO: 30;

(q) a bispecific antibody (Q499-z118/J327-z107/L377-k), wherein the first polypeptide is an H chain consisting of the amino acid sequence of SEQ ID NO: 19, the second polypeptide is an H chain consisting of the amino acid sequence of SEQ ID NO: 24, and the third polypeptide and the fourth polypeptide are a commonly shared L chain of SEQ ID NO: 31;

(r) a bispecific antibody (Q499-z118/J346-z107/L248-k), wherein the first polypeptide is an H chain consisting of the amino acid sequence of SEQ ID NO: 19, the second polypeptide is an H chain consisting of the amino acid sequence of SEQ ID NO: 27, and the third polypeptide and the fourth polypeptide are a commonly shared L chain of SEQ ID NO: 28;

(s) a bispecific antibody (Q499-z121/J327-z119/L404-k), wherein the first polypeptide is an H chain consisting of the amino acid sequence of SEQ ID NO: 20, the second polypeptide is an H chain consisting of the amino acid sequence of SEQ ID NO: 25, and the third polypeptide and the fourth polypeptide are a commonly shared L chain of SEQ ID NO: 32;

(t) a bispecific antibody (Q499-z121/J339-z119/L377-k), wherein the first polypeptide is an H chain consisting of the amino acid sequence of SEQ ID NO: 20, the second polypeptide is an H chain consisting of the amino acid sequence of SEQ ID NO: 26, and the third polypeptide and the fourth polypeptide are a commonly shared L chain of SEQ ID NO: 31; and (u) a bispecific antibody (Q153-G4k/J142-G4h/L180-k), wherein the first polypeptide is an H chain consisting of the amino acid sequence of SEQ ID NO: 12, the second polypeptide is an H chain consisting of the amino acid sequence of SEQ ID NO: 170, and the third polypeptide and the fourth polypeptide are a commonly shared L chain of SEQ ID NO: 171.

Amino acid sequences, molecular weights, isoelectric points, or presence or absence and form of sugar chains of the antibodies of the present invention vary depending on cells or hosts that produce the antibodies or purification methods described later. However, as long as the obtained antibodies have functions equivalent to the antibodies of the present invention, they are included in the present invention. For example, when an antibody of the present invention is expressed in prokaryotic cells such as *E. coli*, a methionine residue will be added to the N terminus of the original antibody amino acid sequence. Antibodies of the present invention also comprise such antibodies.

Bispecific antibodies of the present invention can be produced by methods known to those skilled in the art.

Based on the obtained sequence of the anti-F.IX/F.IXa antibody or anti-F.X antibody, the anti-F.IX/F.IXa antibody or anti-F.X antibody can be prepared, for example, by genetic recombination techniques known to those skilled in the art. Specifically, a polynucleotide encoding an antibody can be constructed based on the sequence of the anti-F.IX/F.IXa antibody or anti-F.X antibody, inserted into an expression vector, and then expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in *E. coli* such as JM109, DH5α, HB101, and XL1-Blue, the expression vectors not only have the characteristics that allow vector amplification in *E. coli*, but must also carry a promoter that allows efficient expression in *E. coli*, for example, lacZ promoter (Ward et al., Nature (1989) 341: 544-546; FASEB J. (1992) δ: 2422-2427), araB promoter (Better et al., Science (1988) 240: 1041-1043), T7 promoter or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The expression plasmid vectors may contain signal sequences for antibody secretion. As a signal sequence for antibody secretion, a pelB signal sequence (Lei, S. P. et al J. Bacteriol. (1987) 169: 4379) may be used when a protein is secreted into the *E. coli* periplasm. The vector can be introduced into host cells by calcium chloride or electroporation methods, for example.

In addition to vectors for *E. coli*, the vectors for producing the antibodies of the present invention include mammalian expression vectors (for example, pcDNA3 (Invitrogen), pEF-BOS (Nucleic Acids. Res. 1990, 18(17): p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdex-Lcw), retroviral expression vectors (for example, pZIPneo), yeast expression vectors (for example, "*Pichia* Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the expression plasmid vectors must have a promoter essential for expression in cells, for example, SV40 promoter (Mulligan et al., Nature (1979) 277: 108), MMLV-LTR promoter, EF1α promoter (Mizushima et al., Nucleic Acids Res. (1990) 18: 5322), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP13, for example.

In addition, the following method can be used for stable gene expression and gene amplification in cells: CHO cells deficient in a nucleic acid synthesis pathway are introduced with a vector that carries a DHFR gene which compensates for the deficiency (for example, pSV2-dhfr (Molecular Cloning $2^{nd}$ edition, Cold Spring Harbor Laboratory Press, 1989)), and the vector is amplified using methotrexate (MTX). Alternatively, the following method can be used for transient gene expression: COS cells with a gene expressing SV40 T antigen on their chromosome are transformed with a vector with an SV40 replication origin (pcD and such). Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

The antibodies of the present invention obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The obtained antibodies can be purified to homogeneity. Separation and purification of the antibodies can be performed using conventional separation and purification methods used for ordinary proteins. For example, the antibodies can be separated and purified by appropriately selecting and combining column chromatography such as affinity chromatography, filtration, ultrafiltration, salting-out, dialysis, SDS polyacrylamide gel electrophoresis, isoelectric focusing, and such, without limitation (Antibodies: A Laboratory Manual. Ed Harlow and David Lane, Cold Spring Harbor Laboratory, 1988). Columns used for affinity chromatography include, for example, protein A columns and protein G columns.

In one embodiment of antibodies of the present invention, since the antibodies of the present invention functionally substitute for cofactor F.VIII, they are expected to become effective pharmaceutical agents against diseases resulting from decrease in activity (function) of this cofactor. Examples of the above-mentioned diseases include bleeding, diseases accompanying bleeding, or a disease caused by bleeding. In particular, there may have excellent therapeutic effects on hemophilias, in which bleeding disorders are caused by a deficiency or decrease of F.VIII/F.VIIIa function. Among the hemophilias, they are expected to become excellent therapeutic agents for hemophilia A, in which bleeding disorders are caused by a hereditary deficiency or decrease of F.VIII/F.VIIIa function.

The present invention provides (pharmaceutical) compositions comprising the antibodies of the present invention and pharmaceutically acceptable carriers. For example, the antibodies of the present invention that recognize both F.IX or F.IXa and F.X, and functionally substitute for F.VIII are expected to become pharmaceuticals (pharmaceutical compositions) or pharmaceutical agents for preventing and/or treating bleeding, diseases accompanying bleeding, diseases caused by bleeding, and the like.

In the context of the present invention, bleeding, diseases accompanying bleeding, and/or diseases caused by bleeding preferably refer to diseases that develop and/or progress due to reduction or deficiency in activity of F.VIII and/or activated coagulation factor VIII (F.VIIIa). Such diseases include the above-described hemophilia A, diseases in which an inhibitor against F.VIII/F.VIIIa appear, acquired hemophilia, von Willebrand's disease, and such, but are not particularly limited thereto.

Pharmaceutical compositions used for therapeutic or preventive purposes, which comprise antibodies of the present invention as active ingredients, can be formulated by mixing, if necessary, with suitable pharmaceutically acceptable carriers, vehicles, and such that are inactive against the antibodies. For example, sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders may be used. They may also comprise other low-molecular-weight polypeptides, proteins such as serum albumin, gelatin, and immunoglobulins, amino acids such as glycine, glutamine, asparagine, glutamic acid, asparagic acid, methionine, arginine, and lysine, sugars and carbohydrates such as polysaccharides and monosaccharides, and sugar alcohols such as mannitol and sorbitol. When preparing an aqueous solution for injection, physiological saline and isotonic solutions comprising glucose and other adjuvants such as D-sorbitol, D-mannose, D-mannitol, and sodium chloride may be used, and if necessary, in combination with appropriate solubilizers such as alcohol (for example, ethanol), polyalcohols (such as propylene glycol and PEG), and nonionic surfactants (such as polysorbate 80, polysorbate 20, poloxamer 188, and HCO-50). By mixing hyaluronidase into the formulation, a larger fluid volume can be administered subcutaneously (Expert Opin Drug Deliv. 2007 July; 4(4): 427-40).

If necessary, antibodies of the present invention may be encapsulated in microcapsules (e.g., those made of hydroxymethylcellulose, gelatin, and poly(methylmethacrylate)), or incorporated as components of colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as controlled-release pharmaceutical agents are also well known, and such methods may be applied to the antibodies of the present invention (Langer et al., J. Biomed. Mater. Res. 15: 267-277 (1981); Langer, Chemtech. 12: 98-105 (1982); U.S. Pat. No. 3,773,919; European Patent Application Publication No. EP 58,481; Sidman et al., Biopolymers 22: 547-556 (1983); EP 133,988).

The dose of a pharmaceutical composition of the present invention may be appropriately determined by considering the dosage form, method of administration, patient age and body weight, symptoms of the patient, type of the disease, and degree of progress of the disease, and is ultimately decided by physicians. Generally, the daily dose for an adult is 0.1 mg to 2,000 mg at once or in several portions. The dose is more preferably 0.2 to 1,000 mg/day, even more preferably 0.5 to 500 mg/day, still more preferably 1 to 300 mg/day, yet more preferably 3 to 100 mg/day, and most preferably 5 to 50 mg/day. These doses may vary, depending on the patient body weight and age, and the method of administration; however, selection of suitable dosage is well within the purview of those skilled in the art. Similarly, the dosing period may be appropriately determined depending on the therapeutic progress.

Furthermore, the present invention provides genes or nucleic acids encoding the antibodies of the present invention. In addition, gene therapy may be performed by incorporating genes or nucleic acids encoding the antibodies of the present invention into vectors for gene therapy. In addition to direct administration using naked plasmids, methods of administration include administration after packaging into liposomes and such, forming a variety of virus vectors such as retrovirus vectors, adenovirus vectors, vaccinia virus vectors, poxvirus vectors, adeno-associated virus vectors, and HVJ vectors (see Adolph "Viral Genome Methods" CRC Press, Florida (1996)), or coating with carrier beads such as colloidal gold particles (WO 93/17706, and such). However, so long as the antibodies are expressed in vivo and their activities are exercised, any method can be used for administration. Preferably, a sufficient dose can be administered by a suitable parenteral route (such as injecting or infusing intravenously, intraperitoneally, subcutaneously, intradermally, intramuscularly, into adipose tissues or mammary glands; inhalation; gas-driven particle bombardment (using electron gun and such); or mucosal route such as nasal drops). Alternatively, the genes encoding the antibodies of the present invention may be administered into blood cells, bone marrow cells, and such ex vivo using liposome transfection, particle bombardment (U.S. Pat. No. 4,945,050), or viral infection, and the cells may be reintroduced into patients. Any gene encoding an antibody of the present invention may be used in gene therapy, and its examples include genes comprising nucleotide sequences encoding the CDRs of Q1, Q31, Q64, Q85, Q153, Q354, Q360, Q405, Q458, Q460, Q499, J232, J259, J268, J300, J321, J326, J327, J339, J344, J346, J142, L2, L45, L248, L324, L334, L377, L404, L406, L408, and L180 described above.

The present invention also provides methods for preventing and/or treating bleeding, diseases accompanying bleeding, and/or diseases caused by bleeding, such methods comprising the step of administering the antibodies or compositions of the present invention. The antibodies or compositions can be administered, for example, by the above-mentioned methods.

Furthermore, the present invention provides kits to be used for the above-mentioned methods, such kits comprising at least an antibody or composition of the present invention. In addition, the kits may include, packaged therewith, a syringe, injection needle, pharmaceutically acceptable medium, alcohol-soaked cotton, adhesive bandage, instructions describing the method of use, and the like.

The present invention also relates to use of a multispecific antigen-binding molecule, a bispecific antibody, or a composition of the present invention in the manufacture of an agent for preventing and/or treating bleeding, a disease accompanying bleeding, or a disease caused by bleeding.

Furthermore, the present invention relates to a multispecific antigen-binding molecule, a bispecific antibody, or a composition of the present invention for preventing and/or treating bleeding, a disease accompanying bleeding, or a disease caused by bleeding.

All prior art references cited herein are incorporated by reference into this description.

EXAMPLES

Herein below, the present invention will be specifically described with reference to the Examples, but it is not to be construed as being limited thereto.

Example 1

Production of Bispecific Antibodies Having F.Xa Generation-Promoting Activity

In WO 2006/109592, hA69-KQ/hB26-PF/hAL-AQ was obtained as a bispecific antibody having an activity of functionally substituting for F.VIII. However, there was the possibility that this antibody has an inhibiting action on the reaction in which F.IXa activates F.X using F.VIIIa as a cofactor.

As shown in FIG. 1, antibodies that bind to F.IX/F.IXa or F.X may inhibit the formation of the F.IXa-F.VIIIa complex (Factor Xase (F.Xase)), or inhibit F.Xase activity (activation of F.X). Hereafter, inhibition of F.Xase formation and/or action of inhibiting F.Xase activity will be mentioned as F.Xase inhibitory action. F.Xase inhibitory action is the inhibition of a coagulation reaction in which F.VIIIa serves as the cofactor, which may suppress the remaining F.VIII function in a patient or the function of the administered F.VIII formulation. Therefore, it is desirable that F.Xa generation-promoting activity, which is the objective of the bispecific antibody, is high, while F.Xase inhibitory action is low. In particular, for patients maintaining F.VIII function and patients receiving treatment with a F.VIII formulation, it is more desirable that F.Xa generation-promoting activity and F.Xase inhibitory action are separated as much as possible.

However, F.Xase inhibitory action is due to the binding to the antigen (F.IXa and/or F.X), which is fundamental property of the antibody. On the other hand, a bispecific antibody having F.Xa generation-promoting action (functionally substituting for F.VIII) also needs to bind to the antigens (F.IXa and F.X). Therefore, it is predicted that it is extremely difficult to obtain bispecific antibodies that do not have an F.Xase inhibitory action but have an F.Xa generation-promoting activity (functionally substituting for F.VIII). Similarly, it is predicted that it is extremely difficult to decrease an F.Xase inhibitory action while increasing the target F.Xa generation-promoting activity by introducing amino acid substitutions in a bispecific antibody.

The present inventors prepared genes for approximately 200 types of antibodies against human F.IXa and human F.X, respectively, using a method known to those skilled in the art, which is the method of obtaining antibody genes from antibody-producing cells of animals immunized with an antigen (human F.IXa or human F.X), and introducing amino acid substitutions, when necessary. Each antibody gene was incorporated into an animal cell expression vector.

40,000 or more bispecific antibodies as anti-F.IXa antibody and anti-F.X antibody combinations were transiently expressed by simultaneously transfecting the anti-human F.IXa antibody H chain expression vector, the anti-human F.X antibody H chain expression vector, and the commonly shared antibody L chain expression vector into mammalian cells such as HEK293H cells. As a comparative control, bispecific antibody hA69-KQ/hB26-PF/hAL-AQ (SEQ ID NOs: 165/166/167) described in WO 2006/109592 was prepared.

Since the mutations mentioned in WO 2006/106905 or WO 1996/027011 were introduced into the CH3 domain of each H chain, it was thought that bispecific antibodies were mainly expressed. Antibodies in the cell culture supernatant were purified by a method known to those skilled in the art using Protein A.

The present inventors measured the F.Xa generation-promoting activity of these antibodies by the method described below. All reactions were performed at room temperature.

Five μL of antibody solution diluted with Tris-buffered saline containing 0.1% bovine serum albumin (hereafter referred to as TBSB) was mixed with 2.5 μL of 27 ng/mL Human Factor IXa beta (Enzyme Research Laboratories) and 2.5 μL of 6 IU/mL of human blood coagulation factor IX (Novact (registered trademark) M (Kaketsuken)), and then incubated in a 384-well plate at room temperature for 30 minutes.

The enzyme reaction in this mixed solution was initiated by adding 5 μL of 24.7 μg/mL of Human Factor X (Enzyme Research Laboratories), and ten minutes later, 5 μL of 0.5 M EDTA was added to stop the reaction. The coloring reaction was initiated by adding 5 μL of coloring substrate solution. After a 50-minute coloring reaction, the change in absorbance at 405 nm was measured using the SpectraMax 340PC$^{384}$ (Molecular Devices). F.Xa generation-promoting activity was indicated as the value obtained by subtracting the absorbance of the antibody-free reaction solution from the absorbance of the antibody-supplemented reaction solution.

TBCP (TBSB containing 93.75 μM synthetic phospholipid solution (SYSMEX CO.), 7.5 mM $CaCl_2$, and 1.5 mM $MgCl_2$) was used as the solvent for Human Factor IXa, Novact (registered trademark) M, and Human Factor X. A coloring substrate solution (N-benzoyl-L-isoleucyl-L-glutamyl-glycyl-L-arginine-p-nitroaniline hydrochloride (S-2222™; (CHROMOGENIX)) was dissolved in purified water at 1.47 mg/mL, and then used in this assay.

To evaluate the F.Xase inhibitory action of the antibodies, the present inventors measured the effects on F.X activation by F.IXa in the presence of F.VIIIa using the following method. All reactions were performed at room temperature.

Five μL of antibody solution diluted with Tris-buffered saline containing 0.1% bovine serum albumin (hereafter referred to as TBSB) was mixed with 2.5 μL of 80.9 ng/mL Human Factor IXa beta (Enzyme Research Laboratories), and then incubated in a 384-well plate at room temperature for 30 minutes.

2.5 μL of 1.8 IU/mL of F.VIIIa (production method will be descried later) was further added, and 30 seconds later, the enzyme reaction in this mixed solution was initiated by adding 5 μL of 24.7 μg/mL of Human Factor X (Enzyme Research Laboratories). Six minutes later, 5 μL of 0.5 M EDTA was added to stop the reaction. The coloring reaction was initiated by adding 5 μL of coloring substrate solution. After a 14-minute coloring reaction, the change in absorbance at 405 nm was measured using the SpectraMax 340PC$^{384}$ (Molecular Devices). F.Xase inhibitory action of an antibody was indicated as the value obtained by subtracting the absorbance of the antibody-free reaction solution from the absorbance of the antibody-supplemented reaction solution.

F.VIIIa was prepared by mixing 5.4 IU/mL of Kogenate (registered trademark) FS (Bayer HealthCare) and 1.11 μg/mL of Human alpha Thrombin (Enzyme Research Laboratories) at a volume ratio of 1:1, incubating at room temperature for one minute, and then adding 7.5 U/mL of Hirudin (Merck KgaA) at a quantity that is half the volume of the mixture solution. The prepared solution was defined as 1.8 IU/mL of FVIIIa, and one minute after addition of Hirudin, this was used for assays.

TBCP (TBSB containing 93.75 μM phospholipid solution (SYSMEX CO.), 7.5 mM $CaCl_2$, and 1.5 mM $MgCl_2$) was used for the solvent for Human Factor IXa, Human Factor X, Kogenate (registered trademark) FS, Human alpha Thrombin, and Hirudin. A coloring substrate solution S-2222™ (CHROMOGENIX) was dissolved in purified water at 1.47 mg/mL, and then used in this assay.

Figure 3:
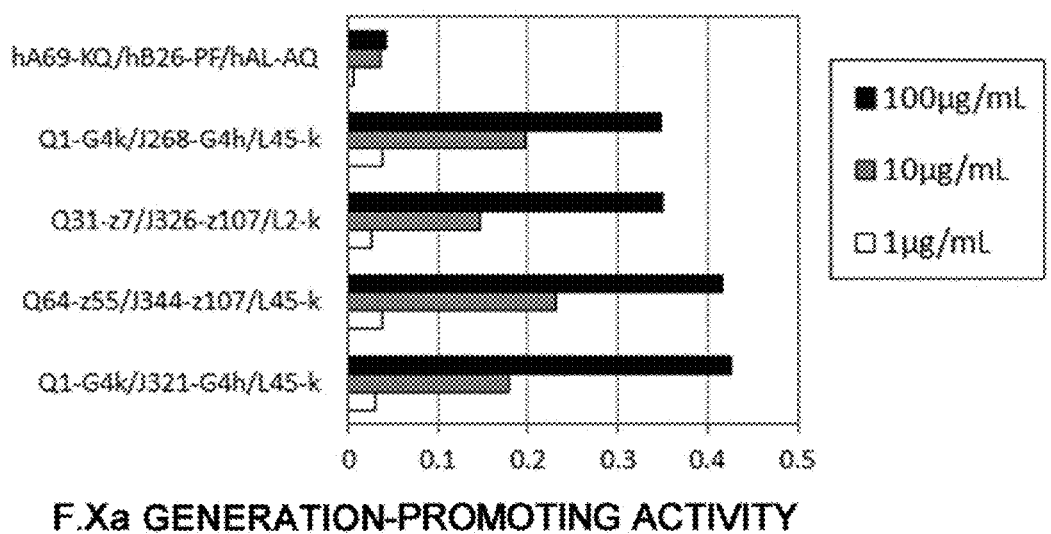
FIG. 3 shows the F.Xa generation-promoting activities of hA69-KQ/hB26-PF/hAL-AQ, Q1-G4k/J268-G4h/L45-k, Q1-G4k/J321-G4h/L45-k, Q31-z7/J326-z107/L2-k, and Q64-z55/J344-z107/L45-k. The concentrations of the antibody solutions were 300, 30, and 3 µg/mL (the concentrations after mixing Human Factor IXa, Novact (registered trademark) M, Human Factor X, and the antibody solution were 100, 10, and 1 µg/mL), the enzyme reaction and color development were performed for ten minutes and 50 minutes, respectively. As a result, these antibodies showed a higher F.Xa generation-promoting activity compared to hA69-KQ/hB26-PF/hAL-AQ described in WO 2006/109592.
Figure 4:
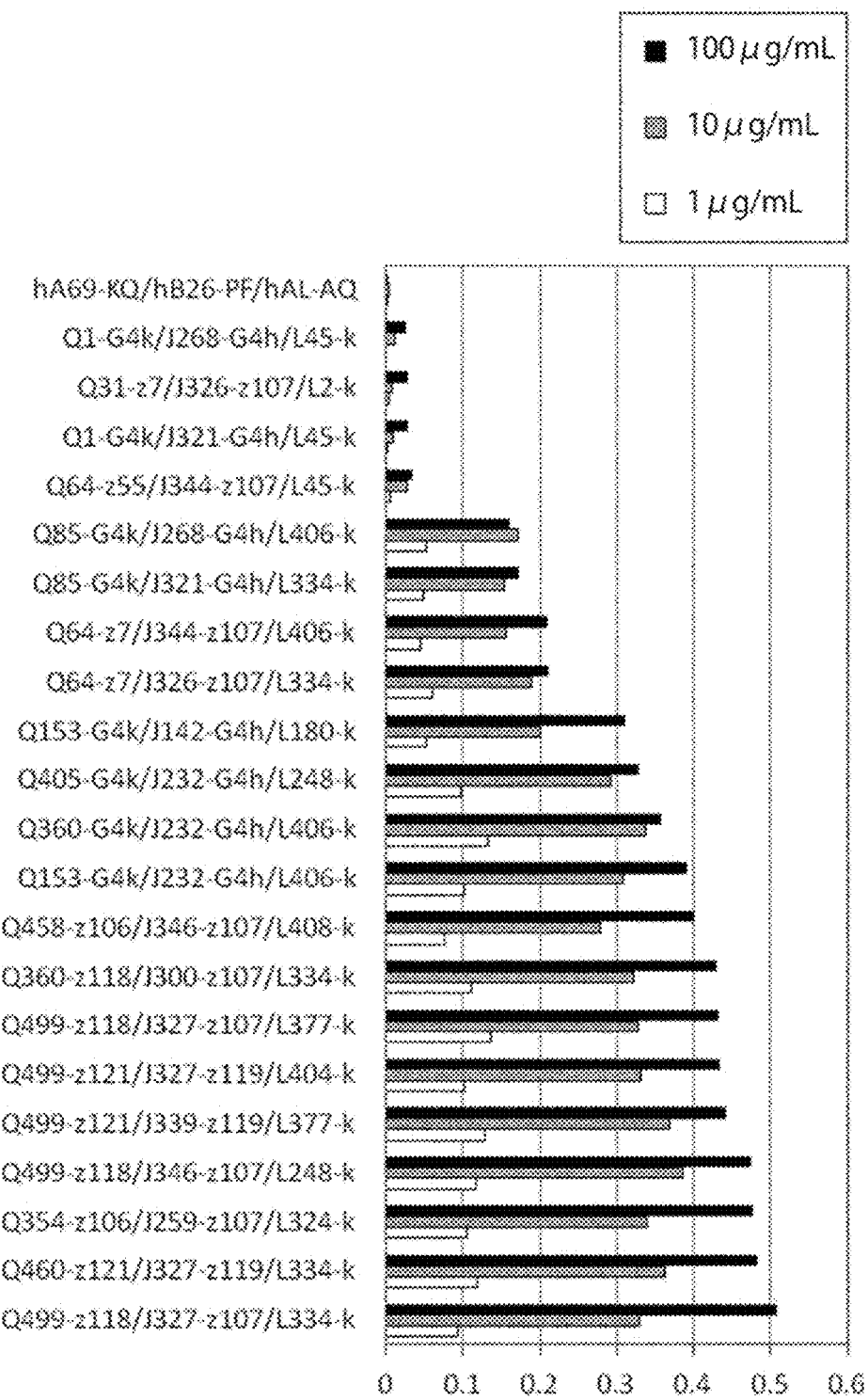
FIG. 4 shows the F.Xa generation-promoting activity of hA69-KQ/hB26-PF/hAL-AQ, prototype antibodies, and modified antibodies with amino acid substitutions. The concentrations of the antibody solutions were 300, 30, and 3 µg/mL (the concentrations after mixing Human Factor IXa, Novact (registered trademark) M, Human Factor X, and the antibody solution were 100, 10, and 1 µg/mL), the enzyme reaction and color development were performed for two minutes and 20 minutes, respectively. As a result, these modified antibodies showed a higher F.Xa generation-promoting activity compared to the prototype antibodies.
Figure 5:
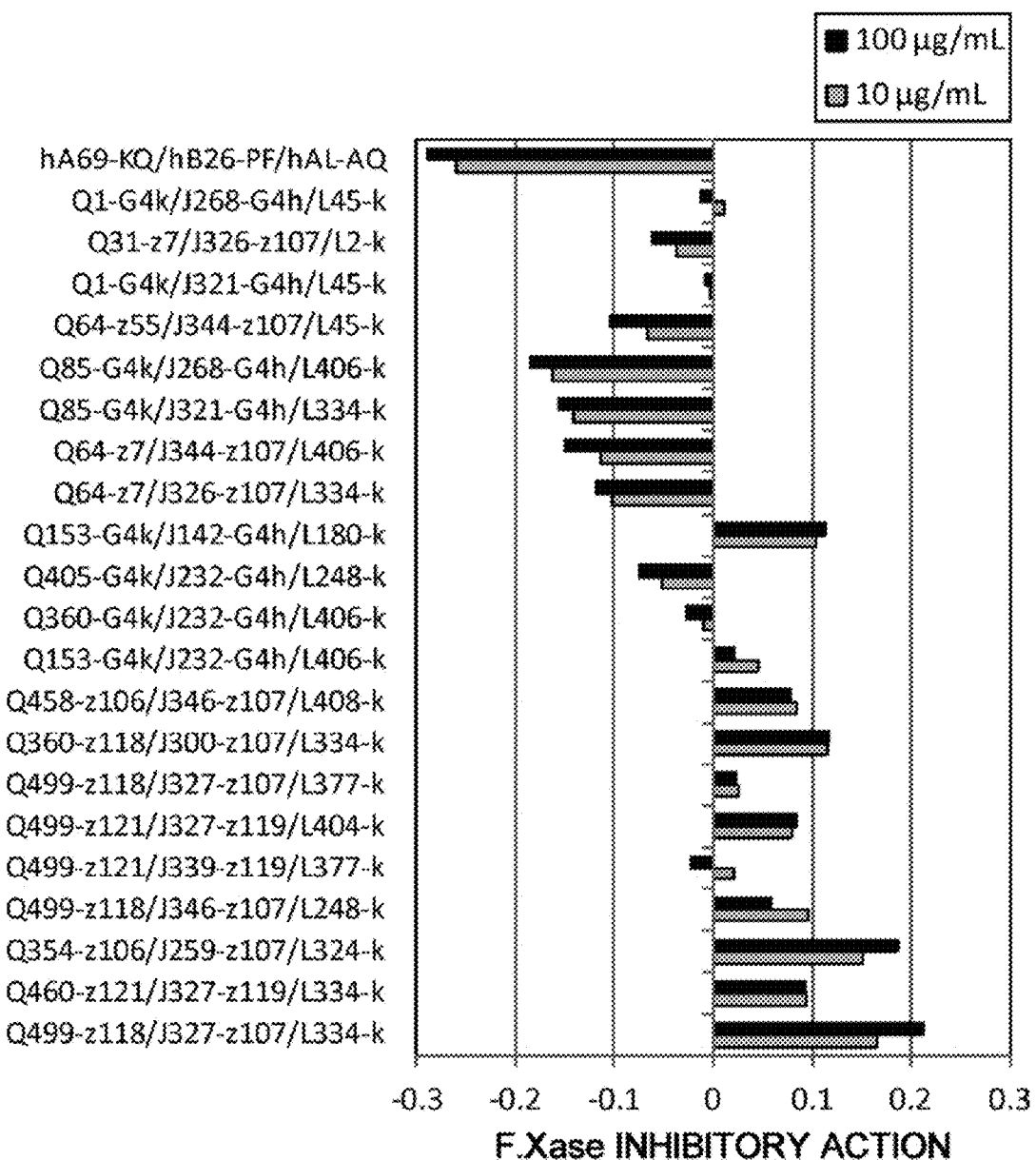
FIG. 5 shows the F.Xase inhibitory action of hA69-KQ/hB26-PF/hAL-AQ, prototype antibodies, and modified antibodies with amino acid substitutions.

The F.Xa generation-promoting activities of each of the bispecific antibodies are indicated in FIGS. 3 and 4, and the F.Xase inhibitory actions of each of the bispecific antibodies are indicated in FIG. 5. Various amino acid substitutions that increase the F.Xa generation-promoting activity have been found, but as expected, most of the amino acid substitutions that increase the F.Xa generation-promoting activity increased F.Xase inhibitory action as well, and suppressing F.Xase inhibitory action while increasing F.Xa generation-promoting activity was very difficult.

Under such circumstances, the inventors of the present application obtained Q1-G4k/J268-G4h/L45-k, Q1-G4k/J321-G4h/L45-k, Q31-z7/J326-z107/L2-k, Q64-z55/J344-z107/L45-k as bispecific antibodies with a high F.Xa generation-promoting activity and a low F.Xase inhibitory action. In addition, Q1-G4k (SEQ ID NO: 1), Q31-z7 (SEQ ID NO: 2), and Q64-z55 (SEQ ID NO: 3) were obtained as anti-human F.IXa antibody H chains, J268-G4h (SEQ ID NO: 4), J321-G4h (SEQ ID NO: 5), J326-z107 (SEQ ID NO: 6), and J344-z107 (SEQ ID NO: 7) were obtained as prototype anti-human F.X antibody H chains, and L2-k (SEQ ID NO: 8) and L45-k (SEQ ID NO: 9) were obtained as prototype commonly shared antibody L chains. The character before the hyphen in the sequence name indicates the variable region and the character after the hyphen indicates the constant region. Each bispecific antibody name is indicated by listing the sequence names of each chain to be transfected.

Figure 2:
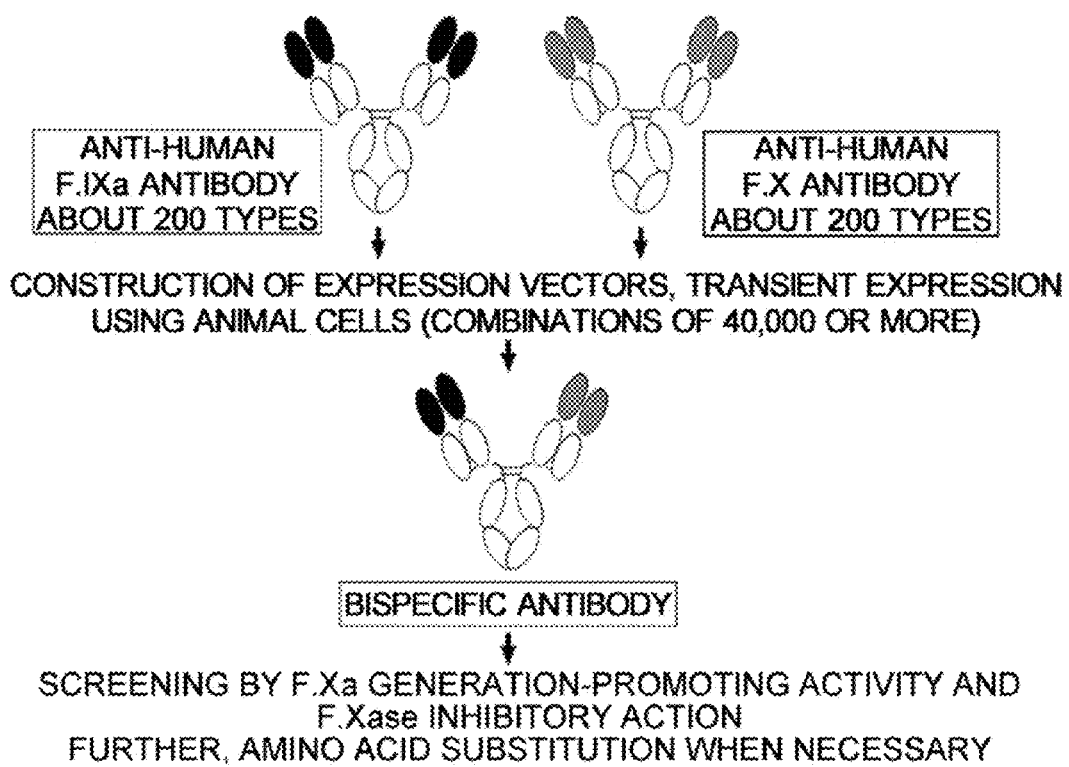
FIG. 2 describes the screening. Approximately 200 types each of genes for antibodies against human F.IXa and human F.X were produced, and they were incorporated into animal cell expression vectors. 40,000 or more bispecific antibodies as a combination of an anti-F.IXa antibody and anti-F.X antibody were transiently expressed. F.Xa generation-promoting activity and F.Xase inhibitory action were evaluated to screen for bispecific antibodies having a high F.Xa generation-promoting activity and a low F.Xase inhibitory action. Furthermore, by substituting amino acids when necessary, prototype antibodies were produced.

Most of the bispecific antibodies having F.Xa generation-promoting activity close to that of hA69-KQ/hB26-PF/hAL-AQ had high F.Xase inhibitory action as expected, but these bispecific antibodies (Q1-G4k/J268-G4h/L45-k, Q1-G4k/J321-G4h/L45-k, Q31-z7/J326-z107/L2-k, Q64-z55/J344-z107/L45-k) were found to have higher F.Xa generation-promoting activity and lower F.Xase inhibitory action than hA69-KQ/hB26-PF/hAL-AQ described in WO 2006/109592. The present inventors conducted examinations to further increase the F.Xa generation-promoting activity and reduce the F.Xase inhibitory action using these four antibodies as prototype antibodies. Screening of bispecific antibodies that increase F.Xa generation-promoting activity and reduce F.Xase inhibitory action is indicated in FIG. 2.

Example 2

Production of Modified Antibodies

The present inventors introduced various combinations of amino acid mutations that affect the F.Xa generation-promoting activities and F.Xase inhibitory actions found in Example 1 to each of the chains of the prototype antibodies by a method known to those skilled in the art such as PCR for introducing mutations and evaluated the combinations of modified chains on a large scale to screen for amino acid substitutions that will further increase the F.Xa generation-promoting activities and reduce the F.Xase inhibitory actions of the four prototype antibodies.

Each of the modified bispecific antibodies with amino acid substitutions were expressed transiently and purified by methods similar to those for the prototype antibodies. The F.Xa generation-promoting activities of the antibodies were measured using the following method. All reactions were performed at room temperature.

Five μL of antibody solution diluted with Tris-buffered saline containing 0.1% bovine serum albumin (hereafter referred to as TBSB) was mixed with 2.5 μL of 27 ng/mL Human Factor IXa beta (Enzyme Research Laboratories) and 2.5 μL of 6 IU/mL of Novact (registered trademark) M (Kaketsuken), and then incubated in a 384-well plate at room temperature for 30 minutes.

The enzyme reaction in this mixed solution was initiated by adding 5 μL of 24.7 μg/mL of Human Factor X (Enzyme Research Laboratories), and two minutes later, 5 μL of 0.5 M EDTA was added to stop the reaction. The coloring reaction was initiated by adding 5 μL of coloring substrate solution. After a 20-minute coloring reaction, the change in absorbance at 405 nm was measured using the SpectraMax 340PC$^{384}$ (Molecular Devices). F.Xa generation-promoting activity was indicated as the value obtained by subtracting the absorbance of the antibody-free reaction solution from the absorbance of the antibody-supplemented reaction solution.

TBCP (TBSB containing 93.75 μM phospholipid solution (SYSMEX CO.), 7.5 mM CaCl$_2$, and 1.5 mM MgCl$_2$) was used as the solvent for Human Factor IXa, Novact (registered trademark) M, and Human Factor X. A coloring substrate solution S-2222™ (CHROMOGENIX) was dissolved in purified water at 1.47 mg/mL, and then used in this assay.

F.Xase inhibitory actions of the antibodies were also evaluated by previously described methods.

The F.Xa generation-promoting activities of each of the modified bispecific antibodies are indicated in FIG. 4, and the F.Xase inhibitory actions of each of the bispecific antibodies are indicated in FIG. 5.

The inventors of the present application obtained Q85-G4k/J268-G4h/L406-k, Q85-G4k/J321-G4h/L334-k, Q64-z7/J344-z107/L406-k, and Q64-z7/J326-z107/L334-k as bispecific antibodies with a high F.Xa generation-promoting activity and a low F.Xase inhibitory action. In addition, they discovered Q64-z7 (SEQ ID NO: 10) and Q85-G4k (SEQ ID NO: 11) as the anti-human F.IXa antibody H chain, and L334-k (SEQ ID NO: 30) and L406-k (SEQ ID NO: 33) as the commonly shared antibody L chains with increased F.Xa generation-promoting activity. Though F.Xase inhibitory actions increased slightly, F.Xa generation-promoting activity increased greatly in Q85-G4k/J268-G4h/L406-k, Q85-G4k/J321-G4h/L334-k, Q64-z7/J344-z107/L406-k, and Q64-z7/J326-z107/L334-k. Since these modified antibodies have very large F.Xa generation-promoting activities compared to increase in F.Xase inhibitory actions, the F.Xa generation-promoting activity and the F.Xase inhibitory action could further be separated compared to the prototype antibodies. This way, combinations that suppress the F.Xase inhibitory action and increase the F.Xa generation-promoting activity were discovered.

While a higher F.Xa generation-promoting activity is preferred for the discovered prototype antibodies to functionally substitute for F.VIII by bispecific antibodies, lower F.Xase inhibitory action was considered favorable to clinically use for patients maintaining F.VIII functions or patients receiving treatment with F.VIII formulations. Therefore, further modifications were performed to produce bispecific antibodies in which F.Xase inhibitory action is not increased while F.Xa generation-promoting activity is further increased.

As a result, Q153-G4k/J232-G4h/L406-k, Q354-z106/J259-z107/L324-k, Q360-G4k/J232-G4h/L406-k, Q360-z118/J300-z107/L334-k, Q405-G4k/J232-G4h/L248-k, Q458-z106/J346-z107/L408-k, Q460-z121/J327-z119/L334-k, Q499-z118/J327-z107/L334-k, Q499-z118/J327-z107/L377-k, Q499-z118/J346-z107/L248-k, Q499-z121/J327-z119/L404-k, Q499-z121/J339-z119/L377-k, and Q153-G4k/J142-G4h/L180-k were obtained as bispecific antibodies with a high F.Xa generation-promoting activity and a low F.Xase inhibitory action. In addition, the Inventors discovered Q153-G4k (SEQ ID NO: 12), Q354-z106 (SEQ ID NO: 13), Q360-G4k (SEQ ID NO: 14), Q360-z118 (SEQ ID NO: 15), Q405-G4k (SEQ ID NO: 16), Q458-z106 (SEQ ID NO: 17), Q460-z121 (SEQ ID NO: 18), Q499-z118 (SEQ ID NO: 19), and Q499-z121 (SEQ ID NO: 20) as the anti-human F.IXa antibody H chain, J232-G4h (SEQ ID NO: 21), J259-z107 (SEQ ID NO: 22), J300-z107 (SEQ ID NO: 23), J327-z107 (SEQ ID NO: 24), J327-z119 (SEQ ID NO: 25), J339-z119 (SEQ ID NO: 26), J346-z107 (SEQ ID NO: 27), J142-G4h (SEQ ID NO: 170) as the anti-human F.X antibody H chains with increased F.Xa generation-promoting activity, and L248-k (SEQ ID NO: 28), L324-k (SEQ ID NO: 29), L377-k (SEQ ID NO: 31), L404-k (SEQ ID NO: 32), L408-k (SEQ ID NO: 34), and L180-k (SEQ ID NO: 171) as the commonly shared antibody L chains.

Since these antibodies have very high F.Xa generation-promoting activities while having suppressed F.Xase inhibitory actions, they may have very useful properties for patients maintaining an F.VIII function and patients receiving treatment with F.VIII formulations. Since antibodies generally have long half-lives, and can be administered subcutaneously, these bispecific antibodies may be of great value to hemophilia A patients, when compared to existing replacement therapy by intravenous administration of existing F.VIII formulations for hemophilia A.

Sequence comparisons of the variable regions of each of the chains used in Example 1 and Example 2 are shown in FIGS. 6A to D. For example, to enhance the F.Xa generation-promoting activity of a bispecific antibody, the following amino acids were found to be important: in the anti-human F.IXa antibody H chain, isoleucine at position 34, asparagine, glutamine, or serine at position 35, serine at position 49, arginine at position 61, glutamic acid at position 62, serine or threonine at position 96, lysine or arginine at position 98, serine or glutamic acid at position 99, phenylalanine or tyrosine at position 100, glycine at position 100b, tyrosine at position 102, and such; in the anti-human F.X antibody H chain, aspartic acid at position 35, arginine at position 53, lysine at position 73, glycine at position 76, lysine or arginine at position 96, tyrosine at position 98, tyrosine at position 100, histidine at position 100a, and such; in the commonly shared antibody L chain, lysine or arginine at position 27, glutamic acid at position 30, arginine at position 31, glutamine at position 32, arginine or glutamine at position 50, serine at position 52, arginine at position 53, lysine at position 54, glutamic acid at position 55, serine at position 92, serine at position 93, proline at position 94, proline at position 95, and such (the variable region amino acids are numbered by Kabat numbering (Kabat E A et al. 1991. Sequences of Proteins of Immunological Interest. NIH)).

INDUSTRIAL APPLICABILITY

The present invention provides multispecific antigen-binding molecules having a high activity of functionally substituting for F.VIII, which are antibodies that recognize both an enzyme and its substrate. Furthermore, the present invention provides multispecific antigen-binding molecules with a high activity of functionally substituting for F.VIII and a low F.Xase inhibitory action, which are antibodies that recognize both an enzyme and its substrate.

Since humanized antibodies may generally have high stability in blood and low immunogenicity, multispecific antibodies of the present invention may be very promising as pharmaceuticals.

The invention claimed is:

1. A bispecific antibody that specifically binds to blood coagulation factor IX and/or activated blood coagulation factor IX, and specifically binds to blood coagulation factor X, wherein the bispecific antibody comprises:
 a first antibody H chain comprising a variable region comprising complementarity determining regions (CDRs) 1, 2, and 3 that comprise SEQ ID NOs: 105-107, respectively;
 a second antibody H chain comprising a variable region comprising CDRs 1, 2, and 3 that comprise SEQ ID NOs: 126-128, respectively; and
 identical first and second antibody L chains, each L chain comprising a variable region comprising CDRs 1, 2, and 3 that comprise SEQ ID NOs: 156-158, respectively.

2. A pharmaceutical composition comprising the bispecific antibody of claim 1 and a pharmaceutically acceptable carrier.

3. A kit comprising the bispecific antibody of claim 1, packaged with instructions for use.

4. A bispecific antibody produced by a method comprising culturing a host cell or host cells comprising nucleic acid or nucleic acids encoding a bispecific antibody, wherein the bispecific antibody comprises:
 a first antibody H chain comprising a variable region comprising CDRs 1, 2, and 3 that comprise SEQ ID NOs: 105-107, respectively;
 a second antibody H chain comprising a variable region comprising CDRs 1, 2, and 3 that comprise SEQ ID NOs: 126-128, respectively; and
 identical first and second antibody L chains, each L chain comprising a variable region comprising CDRs 1, 2, and 3 that comprise SEQ ID NOs: 156-158, respectively.

5. The bispecific antibody of claim 4, wherein the method further comprises obtaining the bispecific antibody produced by the cultured host cell or host cells.

6. A pharmaceutical composition comprising the bispecific antibody of claim 5 and a pharmaceutically acceptable carrier.

7. A kit comprising the bispecific antibody of claim 5, packaged with instructions for use.

8. The bispecific antibody of claim 1, wherein:
 CDRs 1, 2, and 3 of the first antibody H chain consist of SEQ ID NOs: 105-107, respectively;

CDRs 1, 2, and 3 of the second antibody H chain consist of SEQ ID NOs: 126-128, respectively; and CDRs 1, 2, and 3 of each identical L chain consist of SEQ ID NOs: 156-158, respectively.

9. The bispecific antibody of claim 1, wherein the first antibody H chain variable region comprises SEQ ID NO: 45.

10. The bispecific antibody of claim 1, wherein the second antibody H chain variable region comprises SEQ ID NO: 52.

11. The bispecific antibody of claim 1, wherein the identical first and second antibody L chain variable regions each comprise SEQ ID NO: 62.

12. The bispecific antibody of claim 1, wherein the first antibody H chain consists of SEQ ID NO: 20.

13. The bispecific antibody of claim 1, wherein the second antibody H chain consists of SEQ ID NO: 25.

14. The bispecific antibody of claim 1, wherein the identical first and second antibody L chains each consist of SEQ ID NO: 32.

15. A bispecific antibody produced by a method comprising culturing a host cell or host cells comprising nucleic acid or nucleic acids encoding a bispecific antibody, wherein the bispecific antibody comprises:

a first antibody H chain comprising a variable region comprising CDRs 1, 2, and 3 that consist of SEQ ID NOs: 105-107, respectively;

a second antibody H chain comprising a variable region comprising CDRs 1, 2, and 3 that consist of SEQ ID NOs: 126-128, respectively; and identical first and second antibody L chains, each L chain comprising a variable region comprising CDRs 1, 2, and 3 that consist of SEQ ID NOs: 156-158, respectively.

16. The bispecific antibody of claim 15, wherein the method further comprises obtaining the bispecific antibody produced by the cultured host cell or host cells.

17. A pharmaceutical composition comprising the bispecific antibody of claim 16 and a pharmaceutically acceptable carrier.

18. A kit comprising the bispecific antibody of claim 16, packaged with instructions for use.

19. A bispecific antibody that specifically binds to blood coagulation factor IX and/or activated blood coagulation factor IX, and specifically binds to blood coagulation factor X, wherein the bispecific antibody comprises:

a first antibody H chain comprising a variable region comprising SEQ ID NO: 45;

a second antibody H chain comprising a variable region comprising SEQ ID NO: 52; and identical first and second antibody L chains, each comprising a variable region comprising SEQ ID NO: 62.

20. A bispecific antibody produced by a method comprising culturing a host cell or host cells comprising a nucleic acid or nucleic acids encoding a bispecific antibody, wherein the bispecific antibody comprises:

a first antibody H chain comprising a variable region comprising SEQ ID NO: 45;

a second antibody H chain comprising a variable region comprising SEQ ID NO: 52; and identical first and second antibody L chains, each comprising a variable region comprising SEQ ID NO: 62.

21. The bispecific antibody of claim 20, wherein the method further comprises obtaining the bispecific antibody produced by the cultured host cell or host cells.

22. A pharmaceutical composition comprising the bispecific antibody of claim 21 and a pharmaceutically acceptable carrier.

23. A kit comprising the bispecific antibody of claim 21, packaged with instructions for use.

24. The bispecific antibody of claim 19, wherein:

the variable region of the first antibody H chain consists of SEQ ID NO: 45;

the variable region of the second antibody H chain consists of SEQ ID NO: 52; and the variable regions of the identical first and second antibody L chains each consist of SEQ ID NO: 62.

25. A bispecific antibody that specifically binds to blood coagulation factor IX and/or activated blood coagulation factor IX, and specifically binds to blood coagulation factor X, wherein the bispecific antibody comprises:

a first antibody H chain comprising SEQ ID NO: 20;

a second antibody H chain comprising SEQ ID NO: 25; and identical first and second antibody L chains, each comprising SEQ ID NO: 32.

26. The bispecific antibody of claim 25, wherein:

the first antibody H chain consists of SEQ ID NO: 20;

the second antibody H chain consists of SEQ ID NO: 25; and each of the identical first and second antibody L chains consists of SEQ ID NO: 32.

27. A bispecific antibody produced by a method comprising culturing a host cell or host cells comprising nucleic acid or nucleic acids encoding a bispecific antibody comprising:

a first antibody H chain comprising SEQ ID NO: 20;

a second antibody H chain comprising SEQ ID NO: 25; and identical first and second antibody L chains, each comprising SEQ ID NO: 32.

28. The bispecific antibody of claim 27, wherein the method further comprises obtaining the bispecific antibody produced by the cultured host cell or host cells.

29. A pharmaceutical composition comprising the bispecific antibody of claim 28 and a pharmaceutically acceptable carrier.

30. A kit comprising the bispecific antibody of claim 28, packaged with instructions for use.

31. The bispecific antibody of claim 1, wherein the bispecific antibody:

(a) has increased activated blood coagulation factor X generation-promoting activity as compared to a reference antibody that consists of: (i) an antibody H chain consisting of SEQ ID NO: 165, (ii) an antibody H chain consisting of SEQ ID NO: 166, and (iii) two antibody L chains, each consisting of SEQ ID NO: 167; or (b) exhibits less inhibition of F.Xase activity as compared to the reference antibody; or (c) both (a) and (b).

32. The bispecific antibody of claim 1, wherein, when activated blood coagulation factor X generation-promoting activity of a test sample comprising the bispecific antibody is determined in an assay in which the readout is absorbance at 405 nm, the test sample produces an absorbance readout that is more than 0.4 greater than the absorbance at 405 nm produced from an identically-assayed control sample, wherein the control sample is identical to the test sample except lacking any antigen-binding molecule, and wherein the assay comprises steps (a)-(e):

(a) incubating for 30 minutes at room temperature a first reaction mixture comprising: either (i) 5 μL of the test sample in which 300 μg/mL of the bispecific antibody is diluted in Tris-buffered saline containing 0.1% bovine serum albumin, or (ii) 5 μL of the control sample; 2.5 μL of 27 ng/mL human factor IXa beta in Tris-buffered saline containing 0.1% bovine serum albumin, 93.75 μM synthetic phospholipid solution, 7.5 mM $CaCl_2$, and 1.5 mM $MgCl_2$; and 2.5 μL of 6 IU/mL human blood coagulation factor IX in Tris-buffered saline containing 0.1% bovine serum albumin, 93.75 μM synthetic phospholipid solution, 7.5 mM CaCl$_2$, and 1.5 mM MgCl$_2$;
(b) immediately after the incubation of (a), adding to the first reaction mixture 5 μL of 24.7 μg/mL human factor X in Tris-buffered saline containing 0.1% bovine serum albumin, 93.75 μM synthetic phospholipid solution, 7.5 mM CaCl$_2$, and 1.5 mM MgCl$_2$, to generate a second reaction mixture, and incubating the second reaction mixture for 10 minutes at room temperature;
(c) immediately after the incubation of (b), adding to the second reaction mixture 5 μL of 0.5 M ethylenediaminetetraacetic acid (EDTA) in water, to generate a third reaction mixture;
(d) immediately after (c), adding to the third reaction mixture 5 μL of 1.47 mg/mL N-benzoyl-L-isoleucyl-L-glutamyl-glycyl-L-arginine-p-nitroaniline hydrochloride in purified water, to generate a fourth reaction mixture, and incubating the fourth reaction mixture for 50 minutes at room temperature; and
(e) immediately after the incubation of (d), determining the absorbance of the fourth reaction mixture at 405 nm.

33. The bispecific antibody of claim 1, wherein, when inhibition of F.Xase activity of a test sample comprising the bispecific antibody is determined in an assay in which the readout is absorbance at 405 nm, the test sample produces an absorbance readout that is greater than the absorbance at 405 nm produced from an identically-assayed control sample, wherein the control sample is identical to the test sample except lacking any antigen-binding molecule, and wherein the assay comprises steps (a)-(f):
(a) incubating for 30 minutes at room temperature a first reaction mixture comprising: either (i) 5 μL of the test sample in which 300 μg/mL of the bispecific antibody is diluted in Tris-buffered saline containing 0.1% bovine serum albumin, or (ii) 5 μL of the control sample; and 2.5 μL of 80.9 ng/mL human factor IXa beta in Tris-buffered saline containing 0.1% bovine serum albumin, 93.75 μM synthetic phospholipid solution, 7.5 mM CaCl$_2$, and 1.5 mM MgCl$_2$;
(b) immediately after the incubation of (a), adding to the first reaction mixture 2.5 μL of 1.8 IU/mL F.VIIIa in Tris-buffered saline containing 0.1% bovine serum albumin, 93.75 μM synthetic phospholipid solution, 7.5 mM CaCl$_2$, and 1.5 mM MgCl$_2$, to generate a second reaction mixture, and incubating the second reaction mixture for 30 seconds at room temperature;
(c) immediately after the incubation of (b), adding to the second reaction mixture 5 μL of 24.7 μg/mL human factor X in Tris-buffered saline containing 0.1% bovine serum albumin, 93.75 μM synthetic phospholipid solution, 7.5 mM CaCl$_2$, and 1.5 mM MgCl$_2$, to generate a third reaction mixture, and incubating the third reaction mixture for six minutes at room temperature;
(d) immediately after the incubation of (c), adding to the third reaction mixture 5 μL of 0.5 M EDTA, to generate a fourth reaction mixture;
(e) immediately after (d), adding to the fourth reaction mixture 5 μL of 1.47 mg/mL N-benzoyl-L-isoleucyl-L-glutamyl-glycyl-L-arginine-p-nitroaniline hydrochloride in purified water, to generate a fifth reaction mixture, and incubating the fifth reaction mixture at room temperature for 14 minutes; and
(f) immediately after the incubation of (e), determining the absorbance of the fifth reaction mixture at 405 nm.

\* \* \* \* \*